(12) United States Patent
Nakashima et al.

(10) Patent No.: US 7,977,055 B2
(45) Date of Patent: Jul. 12, 2011

(54) METHOD FOR AMPLIFICATION OF NUCLEOTIDE SEQUENCE

(75) Inventors: Katsunori Nakashima, Hiroshima (JP); Isao Ohiso, Hiroshima (JP)

(73) Assignee: Nishikawa Rubber Co., Ltd., Hiroshima-shi (JP)

( * ) Notice: Subject to any disclaimer, the term of this patent is extended or adjusted under 35 U.S.C. 154(b) by 0 days.

(21) Appl. No.: 12/375,205

(22) PCT Filed: Jun. 20, 2007

(86) PCT No.: PCT/JP2007/062416
§ 371 (c)(1), (2), (4) Date: Jan. 26, 2009

(87) PCT Pub. No.: WO2008/013010
PCT Pub. Date: Jan. 31, 2008

(65) Prior Publication Data
US 2010/0055742 A1 Mar. 4, 2010

(30) Foreign Application Priority Data

Jul. 26, 2006 (JP) ................................ 2006-203414
May 23, 2007 (JP) ................................ 2007-136392

(51) Int. Cl.
*C12Q 1/68* (2006.01)
*C12P 19/34* (2006.01)
*C07H 21/04* (2006.01)
(52) U.S. Cl. .................. 435/6; 435/91.2; 536/24.33
(58) Field of Classification Search ............. 435/6, 91.2; 536/23.44
See application file for complete search history.

(56) References Cited

U.S. PATENT DOCUMENTS

| 6,410,278 | B1 * | 6/2002 | Notomi et al. ............... 435/91.2 |
| 2003/0073081 | A1 | 4/2003 | Mukai et al. |
| 2003/0148283 | A1 | 8/2003 | Barany et al. |
| 2004/0067559 | A1 * | 4/2004 | McCarthy et al. ............ 435/91.2 |
| 2007/0020639 | A1 | 1/2007 | Shapero |
| 2007/0099216 | A1 | 5/2007 | Nakashima et al. |

FOREIGN PATENT DOCUMENTS

| WO | WO 9942595 A1 * | 8/1999 |
| WO | WO 03/008623 A2 | 1/2003 |
| WO | WO 2006125267 A1 * | 11/2006 |

OTHER PUBLICATIONS

Turner, D. J. et al. Harnessing asymmetrical substrate recognition by thermostable EndoV to achieve balanced linear amplification in multiplexed SNP typing. Biochem.Cell Biol., vol. 84, pp. 232-242, Apr. 2006.*

Ehses, S., et al., "Optimization and design of oligonucleotide setup for strand displacement amplification", Journal of biochemical and biophysical methods, 2005, pp. 170-186, XP 004963640.

European Official Communication, dated Apr. 8, 2011, issued in Application No. 07 767 254.1.

* cited by examiner

Primary Examiner — Suryaprabha Chunduru
(74) Attorney, Agent, or Firm — Sughrue Mion, PLLC

(57) ABSTRACT

To provide a method for selectively amplifying a target nucleic acid and a method for detecting a nucleic acid by the method, which are useful as a method for synthesizing the nucleic acid. A method for amplifying a nucleic acid sequence (EVA (Endonuclease V-dependent Amplification) method) which selectively amplifies a target nucleic acid in a sample, by the use of an oligonucleotide primer containing a base which can be recognized by an endonuclease V, the endonuclease V and a DNA polymerase having a strand displacement activity, and a method for detecting a nucleic acid by the method.

3 Claims, 18 Drawing Sheets

METHOD FOR AMPLIFICATION OF NUCLEOTIDE SEQUENCE

TECHNICAL FIELD

The present invention relates to a method for selectively amplifying a target nucleic acid, which is useful as a method for synthesizing a nucleic acid, and a method for detecting a nucleic acid by said method.

BACKGROUND OF THE INVENTION

The technique for amplifying a target nucleic acid is one of the exceedingly important techniques in the biotechnology of recent years and is broadly used for the fundamental studies and applications in all manner of fields including biology, medical science, agriculture, forensic medicine, archeology and the like.

1. PCR

Polymerase Chain Reaction (PCR) method is well known as the most typical technique of nucleic acid amplification (e.g., Patent References 1 to 3, Non-patent Reference 1). This method synthesizes a target sequence in vitro, by the action of DNA polymerase activity using two oligonucleotide primers which respectively hybridize with separate DNA chains at both termini of the double-stranded DNA region to be used as the target. Additionally, reverse transcription PCR(RT-PCR) method in which the PCR is combined with reverse transcriptase for the purpose of amplifying a target sequence in RNA is also known (e.g., Non-patent Reference 2). This is a method in which PCR is carried out on a cDNA formed from RNA by the reverse transcription reaction.

In these PCR methods, a specific DNA fragment specified by 5'-ends of the two primers is exponentially accumulated as the amplification product by repeating a reaction consisting of three steps of dissociation (denaturation) of the double-stranded DNA to be used as the template into single-stranded DNA, hybridization (annealing) of the primers to the single-stranded nucleic acid and synthesis (elongation) of template-dependent complementary chain from the primers. Thus, repetition of a total of three steps for adjusting the reaction solution at temperatures which are respectively suited for the above-mentioned three steps (thermal cycle) is required for the PCR method.

One of the useful points of the PCR method is that all parts of the sequence of the target nucleic acid are not necessarily already known, since the amplification reaction proceeds when amplification range of the target nucleic acid is specified by the sequences of two primers (each has a length of about 20 bases or so in general). The fact enables to obtain an unknown nucleic acid sequence by the PCR method from already known limited sequence information. Namely, this is one of the aspects of the reasons why the PCR method has been used for various applications in the broad fields which includes cloning of an unknown gene and preparation of a mutant gene, its use as a preparation method of a nucleic acid with the aim of analyzing an unknown sequence in the subsequent step, and the like.

In the earliest stage of the PCR method, Klenow fragment of *Escherichia coli* DNA polymerase I was used for the elongation of the annealed primers. Since the denaturation step as a step of the thermal cycle of PCR requires a high temperature which is close to 100° C. and the Klenow fragment is inactivated at said temperature, it was necessary to add fresh enzyme in each cycle. Thus, extremely complex operations were necessary in carrying out the original PCR method. Since the problem was solved by the use of a heat-resistant DNA polymerase in the elongation (e.g., Patent References 4 and 5, Non-patent Reference 3) and the reactions were automated by a temperature cycling device (e.g., Patent Reference 6), the PCR became an easily usable general method.

While complicatedness of the operations of the PCR method was improved in this manner, it left a problem in that the temperature cycling device which controls the reaction temperature and time repeatedly and accurately becomes expensive. Additionally, it is necessary to rise/drop temperature of the reaction liquid over a large number of times during the thermal cycle, and the repetition of time required for the changes in temperature was the cause of prolonging the necessary time until completion of the whole reaction steps. A temperature cycling device which enables high speed temperature changes by minimizing the reaction liquid volume by the use of a glass capillary as the reaction vessel has been developed (e.g., Non-patent Reference 4). Although the use of this device sharply shortened the time required for PCR, the device became further expensive in exchange thereof.

2. SDA

For the purpose of solving such problems, several target nucleic acid amplification methods which can be carried out under an isothermal condition have been developed. As one of them, Strand Displacement Amplification (SDA) is known (e.g., Patent References 7 and 8, Non-patent References 5 and 6). In the method, a 5→3' exonuclease activity-deficient DNA polymerase (or a strand displacement DNA polymerase) is used as the enzyme which is necessary for the reaction, and a restriction enzyme is also used. During the SDA reaction, the restriction enzyme provides a 3' end which becomes the starting point of elongation reaction by cutting (nicking) one strand of DNA forming double strand, and the strand displacement DNA polymerase displaces its downstream DNA strand by elongating said 3' end.

In order to enable the nicking with a restriction enzyme by the SDA method, it is necessary to design the reaction in such a manner that a restriction enzyme recognition sequence to be used is present in a primer-annealed sequence. Furthermore, since a general restriction enzyme digests two strands, in order to allow said enzyme to digest single strand alone, it is necessary that the recognition site is provided as a half-modified (hemi-modified) region where one of the strands has resistance to enzyme digestion. For this purpose, it is necessary to use a large amount of modified dNTP, such as α-S-dNTP in which oxygen atom of the α-position phosphate group is replaced by sulfur atom, as the substrate for DNA synthesis. The necessity of modified dNTP results in the increase in cost of the SDA reaction composition. Additionally, there is a case in which efficiency of the modified dNTP to be incorporated by the DNA polymerase is different from usual dNTP. Since the amplified product of the target formed by the SDA method contains modified nucleotide, use of the amplified product in the subsequent step (e.g., analysis of the presence or absence of digestion and fragment length by digesting the product with a restriction enzyme, gene cloning using the product and the like) is limited.

In the early stage of SDA method, although the reaction proceeded at a constant temperature of from about 37 to 42° C., there is a problem that a background reaction is apt to occur. In order to improve such a problem, a so-called thermophilic SDA method, in which the reaction properly proceeded at a constant temperature of from about 50 to 70° C. by the use of a thermostable enzyme, has been developed (e.g., Patent References 9 and 10). On the other hand, the result narrowed the choices of usable restriction enzymes. One of the advantages of the SDA method is that necessity for an expensive temperature cycling device can be avoided since it proceeds at a single temperature. However, the SDA method is unsuitable for the amplification of long target sequence. Also, when the sequence of a target nucleic acid contains a recognition sequence of the restriction enzyme to be used in SDA in its inner region, amplification of such a target sequence undergoes interference due to the property of principle of SDA. Although the problem can be avoided by changing kind of the restriction enzyme to be used, choices of the usable restriction enzymes are limited. Additionally, when the target nucleic acid contains an unknown sequence, it is difficult to predict generation of this problem.

Some methods have been disclosed for improving disadvantages of the SDA method. For example, the use of restriction enzyme which produces 5' protruding end (e.g., Patent Reference 11) such as TspRI or the like or the use of nicking endonuclease (e.g., Patent Reference 12) such as N. BstNBI or the like liberates SDA from the limitations which are concerned in the use of modified nucleotide. However, even by such an improved SDA method, all of the above-mentioned problems cannot be avoided as a whole.

3. RCA

As another isothermal target nucleic acid amplification method, a Rolling Circle Amplification (RCA) method which uses a reaction which resembles to the rolling circle type DNA replication found in bacteriophage and the like is conventionally known (e.g., Non-patent Reference 7). In the method, a strand displacement type DNA polymerase elongates a primer on a cyclic template nucleic acid and produces a copy in which complementary chains of the template are continuously ligated. Additionally, high degree amplification is possible by further annealing the primer for said product to elongate its complementary chain. However, it is necessary to provide the RCA method with a cyclic template nucleic acid for the continuous complementary chain synthesis reaction. For the purpose, an additional step, such as ligation using a ligase, is necessary. Additionally, the amplification product of the RCA method becomes a mixture of nucleic acid fragments having different lengths in which a region consisting of the same sequence is repeatedly continued. Accordingly, in order to use the amplification product obtained by the RCA method in the subsequent step, an additional step, such as digestion of the amplification product with a restriction enzyme, becomes necessary in some cases. The necessity for such an additional step is limiting flexibility and convenience of the RCA method.

4. LAMP

As still another isothermal target nucleic acid amplification method, a Loop-mediated Isothermal Amplification (LAMP) method is known (e.g., Patent Reference 13, Non-patent References 8 and 9). In the method, a loop structure is formed by introducing a region, in which the sequence becomes self-complementary, into a terminal region of a target nucleic acid. The 3' end which becomes the starting point of the elongation reaction is provided by the self-complementary hybridization at the time of the formation of the loop structure or by annealing of a primer to a single-stranded loop region formed by the formation of the loop structure. Said 3' end is elongated by the action of a strand displacement type DNA polymerase and its downstream DNA chain is displaced.

In order to make the loop structure-mediated DNA synthesis chain reaction possible, it is necessary to provide a template which can form a so-called dumbbell type structure having loop structures on both termini as the starting point structures. To effect this, it is necessary to use appropriately designed four primers which can recognize six regions in the target nucleic acid sequence. Designing of such a primer set sharply increases complexity in comparison with the designing of the primer set for PCR use (a pair of primers which recognize two regions). Primer designing for the LAMP method without the aid of a primer designing support software is an extremely complex operation and easily causes mistakes. The complexity of primer designing of LAMP method is inextricably linked to the high specificity of said amplification reaction for the target.

Another main advantage of the LAMP method is a point that it is a reaction which proceeds at a single temperature without requiring an expensive temperature cycling device and has a markedly high amplification efficiency. However, the LAMP method has a limitation in terms of the amplification of a long target sequence. In general, the length of a template which can become a suitable target of the LAMP method is approximately from about 130 to 300 bp as the region defined by the two inner primers. However, approximately about 80 bases among said template region must have a known sequence in order to design the inner primers. Additionally, in the case of a method which jointly uses a loop primer for the purpose of improving the reaction efficiency (e.g., Non-patent Reference 9), the sequence of approximately about 120 bases among said template region must be already known in order to design the inner primer and loop primer. Accordingly, applications of the LAMP method for amplifying target nucleic acids containing unknown sequences are greatly limited. Additionally, the LAMP method also has a limitation to the amplification of short target sequences. This is because it becomes difficult to form a dumbbell structure suitable for the chain reaction when the length of a sequence to be used as the target is shorter than about 120 bp.

Amplification product of the target nucleic acid obtained by the LAMP method becomes a mixture of nucleic acid fragments having different lengths consisting of a repeating structure having mutually complementary sequences on the same chain. Accordingly, in order to use the amplification product obtained by the LAMP method in the subsequent step, an additional step, such as digestion of the amplification product with a restriction enzyme, is necessary. The necessity for such an additional step is limiting flexibility and convenience of the LAMP method.

5. ICAN

As a further isothermal target nucleic acid amplification method, an Isothermal and Chimeric Primer-initiated Amplification of Nucleic Acids (ICAN) method is known (e.g., Patent Reference 14, Non-patent Reference 10). In the method, a chimeric primer comprising both of a region constituted by a DNA and a region constituted by an RNA is used, and the reaction proceeds by the action of ribonuclease H and a strand displacement type DNA polymerase. In said reaction, the ribonuclease H provides a 3' end which becomes the starting point of the elongation reaction, by forming a nick through digestion of the RNA chain of the DNA/RNA hybrid part of a double-stranded nucleic acid formed by the annealing of the chimeric primer. On the other hand, the strand displacement type DNA polymerase elongates the thus provided 3' end and displaces its downstream DNA chain. The ICAN method is also an excellent nucleic acid amplification method from the viewpoint that necessity for an expensive temperature cycling device is excluded. Additionally, as another nucleic acid amplification method which uses a chimeric primer, for example, the methods of Patent References 15 and 16 and the like have also been disclosed.

The amplification method which uses a chimeric primer is confronted by a difficulty that RNA is markedly unstable and apt to be degraded in comparison with DNA. The enzymes which degrade RNA are universally present in organism-derived samples, human perspiration, saliva and skin and various places in the laboratory environments and field environments, and also have such a high heat stability that the activity remains even when they are treated for example at 121° C. using an autoclave. In carrying out its handling and preservation, RNA molecules must be carefully protected from the pollution with the aforementioned degrading enzymes. Additionally, there is a problem that a cost higher than the case of the synthesis of general DNA primers is required for the synthesis of chimeric primers.

6. HDA and RPA

As a still further isothermal target nucleic acid amplification method, a Helicase-dependent Amplification (HAD) method is known (e.g., Patent Reference 17, Non-patent References 11 and 12). In the method, a mechanism of DNA replication in the living body, which is proceeded by a DNA polymerase, a DNA helicase and other accessory protein, is imitated in a test tube. In the HDA method, in order to make annealing of a primer to a template DNA and subsequent elongation by a DNA polymerase possible, a DNA helicase (e.g., UvrD) produces a single-stranded template by separating a double-stranded DNA.

Also, as another isothermal target nucleic acid amplification method, a Recombinase Polymerase Amplification (RPA) method is known (e.g., Patent Reference 18, Non-patent Reference 13). In the method, a recombinase (e.g., uvsX) is allowed to be bound with a primer to form a complex. Said complex (nucleo-protein primer) penetrates into the template double-stranded DNA and enables annealing of the primer to the template. A strand displacement type DNA polymerase elongates said primer and displaces its downstream DNA chain.

The HDA method and RPA method are also excellent nucleic acid amplification methods in terms that an expensive temperature cycling device is not required. However, in the HDA method, it is necessary that cofactors such as ATP, dATP and the like are provided in large amounts during the reaction as energy supplying substances for the helicase activity. Further more, in order to proceed the reaction efficiently in the HDA method, it is necessary in some cases to provide single-stranded DNA binding protein (SSB) such as gp32 and accessory protein such as MutL to the reaction composition for the purpose of supporting the helicase activity (e.g., Non-patent Reference 11). On the other hand, also in the RPA method, a large amount of ATP is required in the reaction liquid as the energy source for the functioning of the recombinase. In addition to this, the presence of SSB such as gp32, a recombinant loading protein such as uvsY and a crowding agent such as polyethylene glycol is essential for the realization of the amplification reaction. Additionally, in the RPA method, it is necessary to allow an ATP regeneration system (e.g., creatine kinase and phosphocreatine) to coexist during the reaction for realizing sufficient amplification efficiency (e.g., Non-patent Reference 13). The necessity for such additional reagents and proteins complicates the reaction composition. It becomes the cause of resulting in a difficulty for optimizing the reaction and of increasing cost of the reaction.

As described in the above, several target nucleic acid amplification methods which can be carried out under an isothermal condition have been devised, and all of them do not require a temperature cycling device and have advantageous points in comparison with the PCR method. Additionally, several methods for amplifying a target nucleic acid under isothermal state have been disclosed other than those exemplified in the above. However, these methods also have respective merits and demerits. Additionally, in some of the nucleic acid amplification methods, due to characteristics of the principle, there are further larger limitations in designing primers in comparison with the designing of the primers for PCR use. When a certain kind of nucleic acid sequence is used as the target, there is a case in which designing of primers for suitably amplifying said sequence is impossible or difficult to attain. Based on such backgrounds, concern has been directed toward the development of a new isothermal target nucleic acid amplification method.

Patent Reference 1: Japanese Patent No. 2093730
Patent Reference 2: Japanese Patent No. 2093731
Patent Reference 3: Japanese Patent No. 2622327
Patent Reference 4: Japanese Patent No. 1814713
Patent Reference 5: Japanese Patent No. 2502041
Patent Reference 6: Japanese Patent No. 2613877
Patent Reference 7: U.S. Pat. No. 5,455,166
Patent Reference 8: U.S. Pat. No. 5,712,124
Patent Reference 9: U.S. Pat. No. 5,648,211
Patent Reference 10: U.S. Pat. No. 5,744,311
Patent Reference 11: International Publication WO99/09211
Patent Reference 12: International Publication WO01/94544
Patent Reference 13: International Publication WO00/28082
Patent Reference 14: International Publication WO00/56877
Patent Reference 15: U.S. Pat. No. 5,916,777
Patent Reference 16: International Publication WO97/04126
Patent Reference 17: International Publication WO04/027025
Patent Reference 18: International Publication WO05/118853
Non-patent Reference 1: Saiki R K, Scharf S, Faloona F, Mullis K B, Horn G T, Erlich H A, Arnheim N: Enzymatic amplification of β-globin genomic sequences and restriction site analysis for diagnosis of sickle cell anemia. *Science*, 230, p. 1350-1354 (1985)
Non-patent Reference 2: Tomohiro Kinoshita, Kunitada Shimotohno: PCR-ho Ni Yoru RNA No Kaiseki, *Tanpakushitsu Kakusan Kohso*, 35, p. 2992-3002 (1990)
Non-patent Reference 3: Saiki R K, Gelfand D H, Stoffel S, Scharf S J, Higuchi R, Horn G T, Mullis K B, Erlich H A: Primer-directed enzymatic amplification of DNA with a thermostable DNA polymerase. *Science*, 29, p. 487-491 (1989)
Non-patent Reference 4: Wittwer C T, Ririe K M, Andrew R V, David D A, Gundry R A, Balis U J: The LightCycler, a microvolume multisample fluorimeter with rapid temperature control. *Biotechniques*, 22, p. 176-181 (1997)
Non-patent Reference 5: Walker G T, Little M C, Nadeau J G, Shank D D: Isothermal in vitro amplification of DNA by a restriction enzyme/DNA polymerase system. *Proc Natl Acad Sci USA*, 89, p. 392-396 (1992)
Non-patent Reference 6: Walker G T, Fraiser M S, Schram J L, Little M C, Nadeau J G, Malinowski D P: Strand displacement amplification—an isothermal, in vitro DNA amplification technique. *Nucleic Acids Res*, 20, p. 1691-1696 (1992)
Non-patent Reference 7: Lizardi P M, Huang X, Zhu Z, Bray-Ward P, Thomas D C, Ward D C: Mutation detection and single-molecule counting using isothermal rolling-circle amplification. *Nat Genet*, 19, p. 225-232 (1998)
Non-patent Reference 8: Notomi T, Okayama H, Masubuchi H, Yonekawa T, Watanabe K, Amino N, Hase T: Loop-mediated isothermal amplification of DNA. *Nucleic Acids Res*, 28, E63 (2000)
Non-patent Reference 9: Nagamine K, Hase T, Notomi T: Accelerated reaction by loop-mediated isothermal amplification using loop primers. *Mol Cell Probes*, 16, p. 223-229 (2002)

Non-patent Reference 10: Masamithsu Shimada, Fumitsugu Hino, Hiroaki Sagawa, Hiroyuki Mukai, Kiyozo Asada, Ikunoshin Kato: To-on idenshi zoshoku-ho (ICAN) ni yoru kekkaku kin kenshutsu shiyaku no kaihatsu, *Rinsho Byori*, 50, p. 528-532 (2002)

Non-patent Reference 11: Vincent M, Xu Y, Kong H: Helicase-dependent isothermal DNA amplification. *EMBO Rep*, 5, p. 795-800 (2004)

Non-patent Reference 12: An L, Tang W, Ranalli T A, Kim H J, Wytiaz J, Kong H: Characterization of a thermostable UvrD helicase and its participation in helicase-dependent amplification. *J Biol Chem*, 280, p. 28952-28958 (2005)

Non-patent Reference 13: Piepenburg O, Williams C H, Stemple D L, Armes N A: DNA detection using recombination proteins. *PLoS Biol*, 4, e204 (2006)

DISCLOSURE OF THE INVENTION

Problems to be Solved by the Invention

The problem of the present invention is to provide a method for selectively amplifying a target nucleic acid, which is useful as a nucleic acid synthesis method, and a method for detecting a nucleic acid by said method.

Means for Solving the Problems

As a result of intensive studies, the inventors of the present invention have constructed a nucleic acid amplification system by finding a method for synthesizing a DNA of a nucleic acid sequence region to be used as the target in the presence of an oligonucleotide primer containing a base which can be recognized by endonuclease V, endonuclease V and a DNA polymerase having a strand displacement activity, to accomplish the present invention. In this connection, the method of the present invention is a nucleic acid amplification method which depends on the nucleic acid cleavage activity of endonuclease V, and may be called sometimes in this description as EVA (Endonuclease V-dependent Amplification) method.

Namely, the present application provides the following invention:

[1] A method for amplifying a nucleic acid sequence, which comprises the following steps (I) and (II);

(I) a step for preparing a reaction mixture comprising at least the following:
(i) a template nucleic acid
(ii) deoxyribonucleotide 3-phosphate
(iii) a DNA polymerase having a strand displacement activity
(iv) endonuclease V
(v) at least one kinds of primer wherein said primer is an oligonucleotide primer which has a nucleotide sequence substantially complementary with the nucleotide sequence of the template nucleic acid and also contains at least one base X which can be recognized by endonuclease V;

(II) a step for incubating the reaction mixture prepared in the step (I) for a period of time sufficient for forming an amplification product under such a temperature condition wherein the following reactions can be carried out:
(i) specific annealing of the primer to the template nucleic acid;
(ii) elongation chain synthesis reaction and strand displacement reaction by the DNA polymerase; and
(iii) recognition of a base X in a nucleic acid chain containing the base X and a cleavage reaction of a phosphodiester bond positioned at a downstream side (3' side) of said base X by endonuclease V;

[2] The method for amplifying a nucleic acid sequence according to the above [1], wherein at least two kinds of primers are contained in the reaction mixture;

[3] The method for amplifying a nucleic acid sequence according to the above [1] or [2], which comprises the following steps (a) to (f) wherein the steps (c) to (f) are continuously repeated:

(a) a step for allowing at least one kinds of primer to cause annealing to the template nucleic acid wherein said primer is an oligonucleotide primer which has a nucleotide sequence substantially complementary with the nucleotide sequence of the template nucleic acid and also contains at least one base X which can be recognized by endonuclease V;

(b) a step for forming a double-stranded nucleic acid from the primer annealed to the template nucleic acid in the step (a), by synthesizing a primer elongation chain complementary with the template nucleic acid by a DNA polymerase;

(c) a step for providing the primer elongation chain with a new 3' end, through the recognition of a base X in the primer elongation chain of the double-stranded nucleic acid formed in the step (b) and cleavage of a phosphodiester bond positioned at a downstream side (3' side) of said base X, by endonuclease V;

(d) a step for forming a double-stranded nucleic acid and carrying out strand displacement, by synthesizing a primer elongation chain complementary with the template nucleic acid from the 3' end of primer elongation chain which is newly provided in the step (c), with a DNA polymerase having a strand displacement activity;

(e) a step for providing the primer elongation chain with a new 3' end, through the recognition of the base X in the primer elongation chain of the double-stranded nucleic acid formed in the step (d) and cleavage of a phosphodiester bond positioned at a downstream side (3' side) of said base X, by endonuclease V; and (f) a step for forming a double-stranded nucleic acid and carrying out strand displacement, by synthesizing a primer elongation chain complementary with the template nucleic acid from the 3' end of primer elongation chain which is newly provided in the step (e), with the DNA polymerase having a strand displacement activity;

[4] The method for amplifying a nucleic acid sequence according to any one of the above [1] to [3], which comprises the following steps (a) to (l) wherein the steps (c) to (f) and steps (i) to (l) are continuously repeated:

(a) a step for allowing at least one kinds of a first primer to cause annealing to the template nucleic acid wherein said primer is an oligonucleotide primer which has the nucleotide sequence substantially complementary with the nucleotide sequence of the template nucleic acid and also contains at least one base X which can be recognized by endonuclease V;

(b) a step for forming a double-stranded nucleic acid from the first primer annealed to the template nucleic acid in the step (a), by synthesizing a primer elongation chain complementary with the template nucleic acid by a DNA polymerase;

(c) a step for providing the primer elongation chain with a new 3' end, through the recognition of the base X in the first primer elongation chain of the double-stranded nucleic acid formed in the step (b) and cleavage of a phosphodiester bond positioned at a downstream side (3' side) of said base X, by endonuclease V;

(d) a step for forming a double-stranded nucleic acid and carrying out strand displacement, by synthesizing a primer elongation chain complementary with the template nucleic acid from the 3' end of the primer elongation chain which is newly provided in the step (c), with a DNA polymerase having a strand displacement activity;

(e) a step for providing the primer elongation chain with a new 3' end, through the recognition of the base X in the first primer elongation chain of the double-stranded nucleic acid formed in the step (d) and cleavage of a phosphodiester bond positioned at a downstream side (3' side) of said base X, by endonuclease V;

(f) a step for forming a double-stranded nucleic acid and carrying out strand displacement, by synthesizing a primer elongation chain complementary with the template nucleic acid from the 3' end of the first primer elongation chain which is newly provided in the step (e), with the DNA polymerase having a strand displacement activity;

(g) a step for using the nucleic acid released by the strand displacement in the step (d) or (f) as the template nucleic acid and allowing at least one kinds of a second primer to cause annealing to said template nucleic acid wherein said primer is an oligonucleotide primer which has a nucleotide sequence substantially complementary with the nucleotide sequence of a template nucleic acid and also contains at least one base X which can be recognized by endonuclease V;

(h) a step for forming a double-stranded nucleic acid from the second primer chain annealed to the template nucleic acid in the step (g), by synthesizing a primer elongation chain complementary with the template nucleic acid by a DNA polymerase;

(i) a step for providing the primer elongation chain with a new 3' end, through the recognition of a base X in the second primer elongation chain of the double-stranded nucleic acid formed in the step (f) and cleavage of a phosphodiester bond positioned at a downstream side (3' side) of said base X, by endonuclease V;

(j) a step for forming a double-stranded nucleic acid and carrying out strand displacement, by synthesizing a primer elongation chain complementary with the template nucleic acid from the 3' end of the second primer elongation chain newly provided in the step (i), with a DNA polymerase having a strand displacement activity;

(k) a step for providing the primer elongation chain with a new 3' end, through the recognition of the base X in the second primer elongation chain of the double-stranded nucleic acid formed in the step (j) and cleavage of a phosphodiester bond positioned at a downstream side (3' side) of said base X, by endonuclease V; and (l) a step for forming a double-stranded nucleic acid and carrying out strand displacement, by synthesizing a primer elongation chain complementary with the template nucleic acid from the 3' end which is newly provided to the primer elongation chain in the step (k), with the DNA polymerase having a strand displacement activity;

[5] The method for amplifying a nucleic acid sequence according to the above [4], which further comprises the following steps (m) to (y) wherein the steps (m) to (y) are continuously repeated:

(m) a step for using the nucleic acid released by the strand displacement in the step (j) or (l) as the template nucleic acid and allowing the first primer described in the step (a) to anneal to said template nucleic acid;

(n) a step for forming a double-stranded nucleic acid from the first primer annealed to the template nucleic acid in the step (m), by synthesizing an elongation chain complementary with the template nucleic acid by a DNA polymerase;

(o) a step for providing the primer elongation chain with a new 3' end, through the recognition of the base X in the first primer elongation chain of the double-stranded nucleic acid formed in the step (n) and cleavage of a phosphodiester bond positioned at a downstream side (3' side) of said base X, by endonuclease V;

(p) a step for forming a double-stranded nucleic acid and carrying out strand displacement, by synthesizing a primer elongation chain complementary with the template nucleic acid from the 3' end which is newly provided to the first primer elongation chain in the step (o), with a DNA polymerase having a strand displacement activity;

(q) a step for providing the primer elongation chain with a new 3' end, through the recognition of the base X in the first primer elongation chain of the double-stranded nucleic acid formed in the step (p) and cleavage of a phosphodiester bond positioned at a downstream side (3' side) of said base X, by endonuclease V;

(r) a step for forming a double-stranded nucleic acid and carrying out strand displacement, by synthesizing a primer elongation chain complementary with the template nucleic acid from the 3' end which is newly provided to the first primer elongation chain in the step (q), with the DNA polymerase having a strand displacement activity;

(s) a step for using the nucleic acid released by the strand displacement in the step (p) or (r) as the template nucleic acid and allowing the second primer described in the step (g) to anneal to said template nucleic acid;

(t) a step for forming a double-stranded nucleic acid from the second primer annealed to the template nucleic acid in the step (s), by synthesizing an elongation chain complementary with the template nucleic acid by a DNA polymerase;

(u) a step for providing the primer elongation chain with a new 3' end, through the recognition of the base X in the primer elongation chain of the double-stranded nucleic acid formed in the step (t) and cleavage of a phosphodiester bond positioned at a downstream side (3' side) of said base X, by endonuclease V;

(v) a step for forming a double-stranded nucleic acid and carrying out strand displacement, by synthesizing a primer elongation chain complementary with the template nucleic acid from the 3' end which is newly provided to the primer elongation chain in the step (u), by a DNA polymerase having a strand displacement activity;

(w) a step for providing the primer elongation chain with a new 3' end, through the recognition of the base X in the primer elongation chain of the double-stranded nucleic acid formed in the step (v) and cleavage of a phosphodiester bond positioned at a downstream side (3' side) of said base X, by endonuclease V;

(x) a step for forming a double-stranded nucleic acid and carrying out strand displacement, by synthesizing a primer elongation chain complementary with the template nucleic acid from the 3' end of the primer elongation chain which is newly provided in the step (w), by the DNA polymerase having a strand displacement activity;

(y) a step for using the nucleic acid released by the strand displacement in the step (v) or (x) as the template nucleic acid in the step (m);

[6] The method for amplifying a nucleic acid sequence according to in any one of the above [1] to [5], wherein optional 2 or 3 of the following (i) to (iii) are carried out on the same template nucleic acid molecule:

(i) specific annealing of the primer to the template nucleic acid (ii) elongation chain synthesis reaction and strand displacement reaction by the DNA polymerase (iii) recognition of the base X in a nucleic acid chain containing the base X and a cleavage reaction of a phosphodiester bond positioned at a downstream side (3' side) of said base X by endonuclease V;

[7] The method for amplifying a nucleic acid sequence according to the above [4] or [5], wherein synthesis of the primer elongation chain complementary with the template nucleic acid from the 3' end of the first primer chain and synthesis of a primer elongation chain complementary with the template nucleic acid from the 3' end of the second primer chain, by a DNA polymerase having a strand displacement activity, are carried out on the same template nucleic acid molecule in mutually facing directions;

[8] The method for amplifying a nucleic acid sequence according to the above [7], wherein the synthesis of a primer elongation chain complementary with the template nucleic acid accompanies a template switching reaction;

[9] The method for amplifying a nucleic acid sequence according to any one of the above [1] to [8], wherein each step is carried out under isothermal condition;

[10] The method for amplifying a nucleic acid sequence according to any one of the above [1] to [9], wherein the template nucleic acid is a single-stranded DNA, a double-stranded DNA or a double-stranded DNA partially having a single-stranded region;

[11] The method for amplifying a nucleic acid sequence according to the above [10], wherein the template nucleic acid is a double-stranded DNA, and which is carried out after a step of converting the double-stranded DNA into a single-stranded DNA;

[12] The method for amplifying a nucleic acid sequence according to the above [11], wherein the step of converting the double-stranded DNA into a single-stranded DNA is carried out by thermal denaturation;

[13] The method for amplifying a nucleic acid sequence according to any one of the above [10] to [12], wherein the template nucleic acid is a cDNA obtained by a reverse transcription reaction which uses RNA as the template;

[14] The method for amplifying a nucleic acid sequence according to the above [13], which is carried out after a step of synthesizing the cDNA by a reverse transcription reaction which uses RNA as the template;

[15] The method for amplifying a nucleic acid sequence according to the above [13] or [14], wherein a DNA polymerase having reverse transcriptase activity is used as a reverse transcriptase in the reverse transcription reaction;

[16] A method for amplifying an unknown nucleic acid sequence by the method described in any one of the above [1] to [15], wherein an unknown nucleic acid sequence region comprising one base or more is contained in an amplifying region, which is also a region to which the primer does not anneal, in the template nucleic acid;

[17] The method for amplifying a nucleic acid sequence according to any one of the above [1] to [16], wherein a melting temperature adjusting agent is contained in the reaction mixture;

[18] The method for amplifying a nucleic acid sequence according to the above [17], wherein the melting temperature adjusting agent is betaine;

[19] The method for amplifying a nucleic acid sequence according to any one of the above [1] to [18], wherein an agent for stabilizing a single-stranded nucleic acid is contained in the reaction mixture;

[20] The method for amplifying a nucleic acid sequence according to any one of the above [1] to [19], wherein an outer primer which anneals to a region of upstream side (5' side) from the region to which the primer containing the base X anneals is further contained in the reaction mixture;

[21] The method for amplifying a nucleic acid sequence according to any one of the above [1] to [20], wherein the base X is selected from the group consisting of hypoxanthine, xanthine, uracil, oxanine and AP site (apurinic/apyrimidinic site or abasic site);

[22] The method for amplifying a nucleic acid sequence according to the above [21], wherein the base X is hypoxanthine or uracil;

[23] The method for amplifying a nucleic acid sequence according to any one of the above [1] to [22], wherein the base which is adjacent to the 5' side of the base X is adenine or thymine;

[24] The method for amplifying a nucleic acid sequence according to any one of the above [1] to [22], wherein the base which is adjacent to the 3' side of the base X is adenine or thymine;

[25] The method for amplifying a nucleic acid sequence according to any one of the above [1] to [24], wherein a base is not present in the downstream side (3' side) than the base X in the primer, or the number of bases of the downstream side (3' side) than the base X of the primer is from 1 to 50 bases;

[26] The method for amplifying a nucleic acid sequence according to any one of the above [1] to [25], wherein the number of bases of the upstream side (5' side) than the base X of the primer is from 10 to 100 bases;

[27] The method for amplifying a nucleic acid sequence according to any one of the above [1] to [26], wherein at least one modified nucleotide showing nuclease resistance is contained in the primer;

[28] The method for amplifying a nucleic acid sequence according to the above [27], wherein containing amount of the modified nucleotide showing nuclease resistance among all nucleotides in the upstream side (5' side) of the base X of the primer is 60% or less;

[29] The method for amplifying a nucleic acid sequence according to the above [27] or [28], wherein the modified nucleotide is an ($\alpha$-S) nucleotide in which the oxygen atom binding to the $\alpha$-position phosphorus atom of the nucleotide is replaced by sulfur atom;

[30] The method for amplifying a nucleic acid sequence according to any one of the above [1] to [29], wherein the DNA polymerase having strand displacement activity is any one of Klenow fragment of DNA polymerase I derived from *Escherichia coli*, Phi29 DNA polymerase derived from bacteriophage $\phi$29, 5'→3' exonuclease-deficient Bst DNA polymerase derived from *Bacillus stearothermophilus*, and 5'→3' exonuclease-deficient Bca DNA polymerase derived from *Bacillus caldotenax*;

[31] The method for amplifying a nucleic acid sequence according to any one of the above [1] to [30], wherein the endonuclease V is a mutation type specific endonuclease V which does not show nonspecific nucleic acid cleavage activities but shows a specific nucleic acid cleavage activity;

32. The method for amplifying a nucleic acid sequence according to the above [31], wherein the specific nucleic acid cleavage activity is a nucleic acid cleavage activity which is specific to deoxyinosine;

33. The method for amplifying a nucleic acid sequence according to the above [31] or [32], wherein the mutation type endonuclease V is, of the amino acid sequence of a wild type endonuclease V, (a) the 80-position amino acid or an amino acid of a position equivalent to the 80-position of *Thermotoga maritima* endonuclease V is mutated to an other amino acid $Z_1$, and (b) the 105-position amino acid or an amino acid of a position equivalent the 105-position of *Thermotoga maritima* endonuclease V is mutated to an other amino acid $Z_2$;

[34] The method for amplifying a nucleic acid sequence according to the above [33], wherein the amino acid $Z_1$ is any one of alanine, glycine, leucine, isoleucine, valine, phenylalanine and methionine;

[35] The method for amplifying a nucleic acid sequence according to the above [33] or [34], wherein the amino acid $Z_2$ is any one of alanine, glutamic acid, asparagine, glutamine, arginine, glycine, serine, threonine and histidine;

[36] The method for amplifying a nucleic acid sequence according to any one of [33] to [35], wherein both of the amino acids $Z_1$ and $Z_2$ are alanine;

[37] The method for amplifying a nucleic acid sequence according to any one of [33] to [36], wherein the wild type endonuclease V is derived from a thermophilic bacterium or thermophilic archaebacterium.

[38] The method for amplifying a nucleic acid sequence according to any one of [33] to [37], wherein the wild type endonuclease V is derived from *Thermotoga maritima;*

[39] The method for amplifying a nucleic acid sequence according to any one of the above [33] to [38], wherein the wild type endonuclease V has the amino acid sequence shown by SEQ ID NO:1;

[40] The method for amplifying a nucleic acid sequence according to any one of the above [31] to [39], wherein the endonuclease V has heat resistance;

[41] The method for amplifying a nucleic acid sequence according to any one of the above [31] to [36], wherein the mutation type specific endonuclease V has the amino acid sequence shown by SEQ ID NO:2;

[42] A method for detecting a target nucleic acid in a sample, which comprises a step of amplifying a target nucleic acid by the method for amplifying a nucleic acid sequence described in any one of the above [1] to [41] and a step of detecting whether or not an amplification product was formed by said step;

[43] The method for detecting a target nucleic acid according to the above [42], which comprises a step of amplifying a target nucleic acid in the presence of a nucleic acid detecting agent by the method for amplifying a nucleic acid sequence described in any one of the above [1] to [41] and a step of detecting whether or not the amplification product was formed by said step based on a change in the signal derived from the detecting agent;

[44] A nucleic acid amplification reagent kit to be used in the method for amplifying a nucleic acid sequence described in any one of the above [1] to [41], which comprises a medium which records instructions instructing the use of an endonuclease V and a DNA polymerase having strand displacement activity;

[45] The nucleic acid amplification kit according to the above [44], which comprises at least an endonuclease V or at least the endonuclease V and a DNA polymerase having strand displacement activity;

[46] A nucleic acid detection reagent kit to be used in the method for detecting a target nucleic acid described in the above [42] or [43], which comprises a medium which records instructions instructing the use of an endonuclease V and a DNA polymerase having strand displacement activity;

[47] The nucleic acid detection reagent kit according to the above [46], which comprises at least an endonuclease V or at least the endonuclease V and a DNA polymerase having strand displacement activity;

[48] The nucleic acid amplification reagent kit according to any one of the above [44] to [47], wherein the endonuclease V is a mutation type endonuclease V.

Effect of the Invention

According to the nucleic acid amplification method of the present invention, synthesis and amplification of a nucleic acid can be achieved under an isothermal reaction condition, in which an expensive temperature cycling device is not necessary. Also, the primer to be used in the nucleic acid amplification method of the present invention has advantage of having fewer limitations regarding its designing.

Also, according to the nucleic acid amplification method of the present invention, it is not necessary to use a modified dNTP (e.g., α-S-dNTP or the like) which results in the increase of cost, in a large amount as the substrate for DNA synthesis. Also, there is an advantage in that it does not provide an amplification product which has a limitation to its use in the subsequent step, such as a mixture of nucleic acid fragments containing a large amount of modified nucleotide and nucleic acid fragment having different lengths in which the target sequence is repeated many times. Also, according to the nucleic acid amplification method of the present invention, an optional sequence region can be used as the target independent of the presence or absence of a specific restriction enzyme recognition region in the target sequence.

Additionally, in the nucleic acid amplification method of the present invention, an additional pre-step for preparing a cyclic template nucleic acid is not essential, and it is not necessary to design complex and restrictive primer sequences for a large number of regions for the purpose of achieving amplification of a certain single target sequence. Also, according to the nucleic acid amplification method of the present invention, it is not necessary to contain an unstable and degradation-susceptible RNA component in the primer molecule. Also, according to the nucleic acid amplification method of the present invention, it is not necessary to allow cofactors such as ATP, dATP and the like as energy supplying substances for the enzyme activity to be present in the reaction in large amounts during the reaction, and it is not necessary to allow an ATP regeneration system to coexist during the reaction.

BEST MODE FOR CARRYING OUT THE INVENTION

Figure 1:
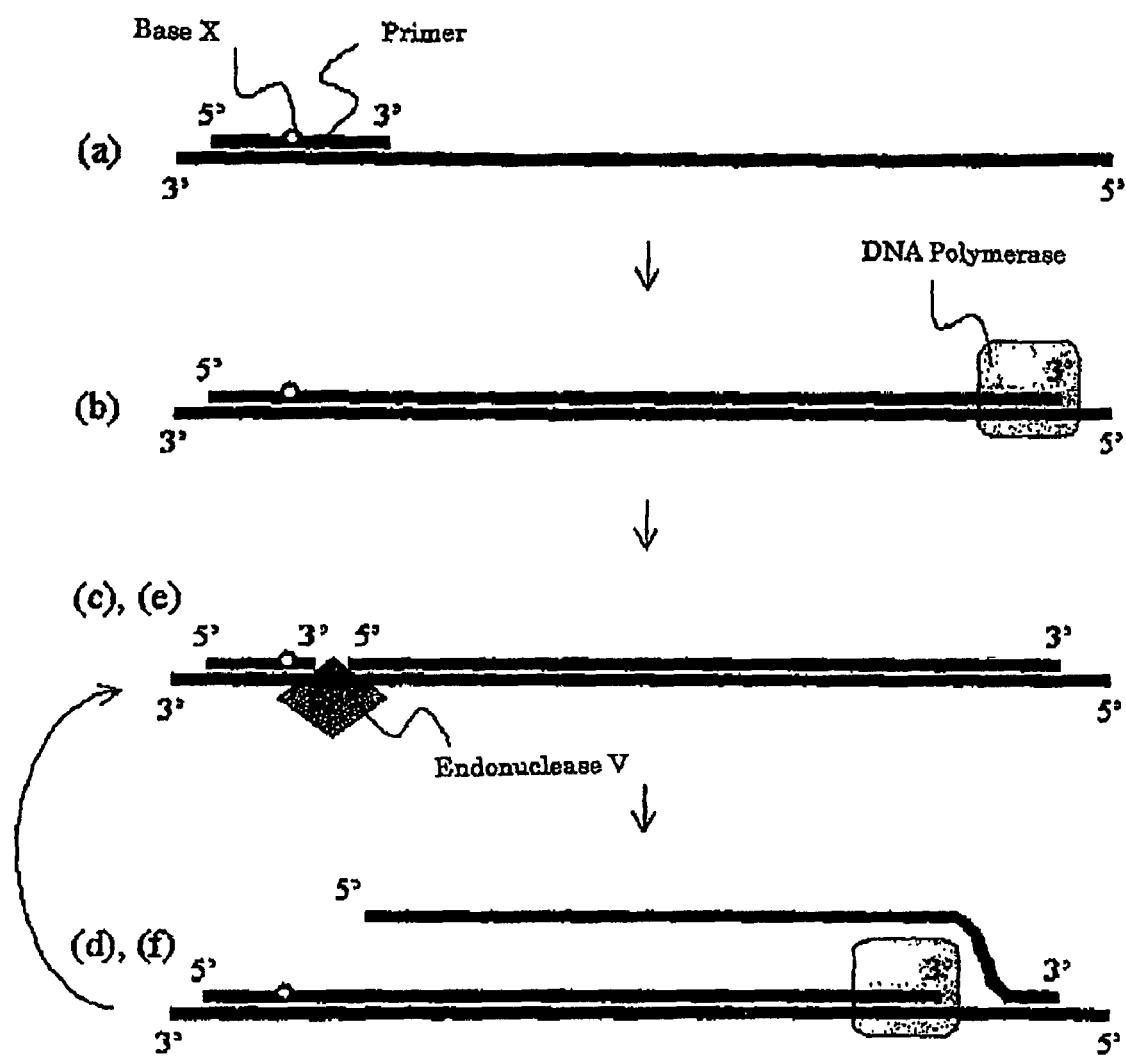
FIG. 1 shows a schematic illustration to be used for the description of a nucleic acid amplification method which uses at least one primer as an embodiment of the present invention.

The following describes the present invention in detail.

The present invention describes on a new amplification method called "endonuclease V-dependent amplification" (EVA; Endonuclease V-dependent Amplification). In the EVA of the present invention, the reaction proceeds based on the activities of two enzymes endonuclease V and a DNA polymerase having a strand displacement activity. Additionally, the reaction of EVA is carried out in the presence of an oligonucleotide primer containing at least one base which can be recognized by the endonuclease V.

The "endonuclease V" as used in this description means an enzyme classified as an enzyme number EC 3.1.21.7 by the enzyme nomenclature of International Union of Biochemistry and Molecular Biology (IUBMB). The enzyme is also called deoxyinosine 3'-endonuclease in some cases. Additionally, in the past classification, the enzyme was also described as EC 3.1.22.3 or EC 3.1.-.-. In this connection, although a bacteriophage T4-derived DNA modification enzyme, T4 endonuclease V, is called by resembling name, it is an enzyme classified into EC 3.1.25.1 which is an enzyme having an activity different from that of the endonuclease V described in the present invention.

The "strand displacement activity" according to this description means that, when synthesis of a new complementary chain is carried out in accordance with the nucleotide sequence of a nucleic acid to be used as the template, the old complementary chain which is present in the synthesis proceeding direction and is already formed a double strand with the template chain is released while it proceeds by replacing the old complementary chain with a newly formed complementary chain, namely the activity capable of carrying out the "strand displacement". The reaction by said activity is called "strand displacement reaction", and the DNA polymerase having said activity is also called "strand displacement type" DNA polymerase.

The "nucleic acid" according to this description represents a double-stranded or single-stranded DNA or RNA molecule, and further represents a DNA/RNA hybrid. The "double strand" means a nucleic acid molecule which is entirely or partially double-stranded. The double-stranded nucleic acid molecule may be either nicked or not nicked (intact). The double strand may have a blunt end or a single-stranded tail part. The single-stranded nucleic acid molecule may have a hairpin-, loop- or stem-shaped secondary structure.

The nucleic acid to be used in the present invention may be prepared or separated from any supply source, and for example, it may be isolated from a supply source such as an environmental resource, food, agricultural product, fermented product, body fluid or tissue of the living body, cell or virus and the like. The body fluid or tissue of the living body includes, for example, blood, milk, cerebrospinal fluid, phlegm, saliva, feces, lung suction liquid, swab of a mucous membrane or tissue sample and the like. The nucleic acid sample includes any one of chromosomal DNA, extrachromosomal DNA including plasmid DNA, recombinant DNA, a DNA fragment, messenger RNA, transfer RNA, ribosomal RNA, double-stranded RNA or other RNA which can be found in a cell or virus.

Additionally, the nucleic acid to be used in the present invention may be an isolated substance, a cloned substance or a substance synthesized by a chemical means. It may be a substance in which any one of the above-mentioned nucleic acid underwent a modification such as a chemical change (e.g., methylation) on individual nucleotide in the nucleic acid. Said modification may be a naturally occurred matter or a matter caused by in vitro synthesis.

The "substantially complementary" nucleotide sequence as used in this description means a nucleotide sequence which can perform annealing to a DNA which becomes the template, under the reaction conditions to be employed. Namely, the substantially complementary nucleotide sequence means that it may have a small number of non-complementary parts based on the whole nucleotide sequence region which becomes the object, and preferably, it may be completely complementary or have one or a few non-complementary bases.

The "3' end side" and "3' side" as used in this description mean a side or direction close to the 3' end of a nucleic acid chain when it is looked in the 5'→3' direction from a region or position in said nucleic acid chain. Also, when it is looked from the whole nucleic acid chain, it means a part or direction from the center to 3' end of said nucleic acid chain. As a term having the same meaning, "downstream side" is also used.

The "5'end side" and "5' side" as used in this description mean a side or direction close to the 5' end of a nucleic acid chain when it is looked in the 5'→3' direction from a region or position in said nucleic acid chain. Also, when it is looked from the whole nucleic acid chain, it means a part or direction from the center to 5' end of said nucleic acid chain. As a term having the same meaning, "upstream side" is also used.

The case that an enzyme "shows activity" according to this description includes a case where the enzyme can act under specific or specified range of reaction composition and reaction condition, and also includes a case that the enzyme can act only under said specific reaction composition and reaction condition. It also includes a case that the enzyme can act under optimum reaction composition and reaction condition.

The case that an enzyme "does not shows activity" according to this description is not limited to a case where there is absolutely no activity in the enzyme, and a case where the activity is not detected under the employed condition or a case where the activity is so small that it can be substantially neglected can also be included.

1. Nucleic Acid Sequence Amplification Method of the Present Invention

The present invention provides an amplification method of the present invention called "endonuclease V-dependent amplification" (EVA). In the EVA, the reaction proceeds based on the activities of two enzymes, endonuclease V and a DNA polymerase having a strand displacement activity. Additionally, the reaction of EVA is carried out in the presence of an oligonucleotide primer containing at least one base which can be recognized by the endonuclease V.

The endonuclease V "EC 3.1.21.7" is also called deoxyinosine 3'-endonuclease, which is an enzyme which recognizes the base (hypoxanthine) of deoxyinosine in a DNA chain and hydrolyzes a phosphodiester bond of its vicinity (mainly the second phosphodiester bond of the 3' side of the recognition base).

Also, in addition to this deoxyinosine-specific cleavage activity, the endonuclease V has the activity to cleave a DNA chain by recognizing the base of deoxyuridine (uracil), the base of deoxyxanthosine (xanthine), the base of deoxyoxanosine (oxanine), an AP site (apurinic/apyrimidinic site or abasic site) and the like in the DNA chain.

Additionally, the endonuclease V also has the activity to cleave a DNA chain by recognizing various DNA structures including mismatch of bases, insertion/deletion of a base, flap structure, pseudo-Y structure and the like. The endonuclease V or a gene coding for the same has been found in or isolated from various organism species, and particularly regarding those which were derived from *Escherichia coli* and *Thermotoga maritima*, their properties have been examined relatively thoroughly.

The above-mentioned properties of endonuclease V are described in detail, for example, in the following references [1] to [11].

[1] Yao M, Hatahet Z, Melamede R J, Kow Y W: Purification and characterization of a novel deoxyinosine-specific enzyme, deoxyinosine 3' endonuclease, from *Escherichia coli*. *J Biol Chem,* 269, p. 16260-8 (1994).

[2] Yao M. Kow Y W: Strand-specific cleavage of mismatch-containing DNA by deoxyinosine 3'-endonuclease from *Escherichia coli. J Biol Chem,* 269, p. 31390-6 (1994).

[3] Yao M. Kow Y W: Interaction of deoxyinosine 3'-endonuclease from *Escherichia coli* with DNA containing deoxyinosine. *J Biol Chem,* 270, p. 28609-16 (1995).

[4] Yao M. Kow Y W: Cleavage of insertion/deletion mismatches, flap and pseudo-Y DNA structures by deoxyinosine 3'-endonuclease from *Escherichia coli. J Biol Chem,* 271, p. 30672-6 (1996).

[5] Yao M. Kow Y W: Further characterization of *Escherichia coli* endonuclease V. Mechanism of recognition for deoxyinosine, deoxyuridine, and base mismatches in DNA. *J Biol Chem,* 272, p. 30774-9 (1997).

[6] Zvonimir Siljkovic: Crystal structure of the DNA repair enzyme endonuclease V from *Thermotoga maritima.* Master's Thesis, Purdue University, Thesis p. 46615 MS (2000).

[7] Huang J, Barany F, Cao W: Multiple cleavage activities of endonuclease V from *Thermotoga maritima*: recognition and strand nicking mechanism. *Biochemistry,* 40, p. 8738-48 (2001).

[8] Huang J, Lu J, Barany F, Cao W: Mutational analysis of endonuclease V from *Thermotoga maritima. Biochemistry,* 41, p. 8342-50 (2002).

[9] Liu J, He B, Qing H, Kow Y W: A deoxyinosine specific endonuclease from hyperthermophile, *Archaeoglobus fulgidus*: a homolog of *Escherichia coli* endonuclease V. *Mutat Res,* 461, p. 169-77 (2000).

[10] Hitchcock T M, Gao H, Cao W: Cleavage of deoxyoxanosine-containing oligodeoxyribonucleotides by bacterial endonuclease V. *Nucleic Acids Res,* 32, p. 4071-80 (2004).

[11] Feng H, Klutz A M, Cao W: Active Site Plasticity of Endonuclease V from *Salmonella typhimurium. Biochemistry,* 44, p. 675-83 (2005).

In order to properly carry out the nucleic acid amplification method of the present invention, a step for preparing a reaction mixture containing substances which is necessary for the reaction and a step for incubating said reaction mixture for a period of time which is sufficient for forming the amplification product may be carried out. Namely, a preferable embodiment of the present invention is a method for amplifying a nucleic acid sequence, which comprises the following two steps of (I) and (II):

(I) a step for preparing a reaction mixture containing at least the following (i) a template nucleic acid (ii) deoxyribonucleotide 3-phosphate (iii) a DNA polymerase having a strand displacement activity (iv) endonuclease V (v) at least one kind of a primer (wherein said primer is an oligonucleotide primer which has a nucleotide sequence which is substantially complementary with the nucleotide sequence of the template nucleic acid and also contains at least one base X which can be recognized by endonuclease V;

(II) a step for incubating the reaction mixture prepared in the step (I) for a period of time which is sufficient for forming the amplification product under such a temperature condition that the following reactions can be carried out (i) specific annealing of the primer to the template nucleic acid (ii) elongation chain synthesis reaction and strand displacement reaction by the DNA polymerase (iii) recognition of a base X in a nucleic acid chain containing the base X by endonuclease V and a cleavage reaction of a phosphodiester bond positioned at a downstream side (3' side) of said base X.

Additionally, another preferable embodiment of the present invention is the method wherein the aforementioned primer in the reaction mixture is at least two species of primers.

The following describes an example of the reaction modes by which a nucleic acid is amplified by the nucleic acid amplification method of the present invention, based on the schematic graphs for helping understanding. In this connection, the present invention is not limited by the modes.

(1) Embodiment 1

A Case of Using at Least One Primer

A preferable embodiment of the present invention is a nucleic acid amplification method which comprises the following steps (a) to (f) "wherein the steps (c) to (f) are continuously repeated":

(a) a step for allowing at least one kind of a primer to cause annealing to a template nucleic acid (wherein said primer is an oligonucleotide primer which has a nucleotide sequence which is substantially complementary with the nucleotide sequence of a template nucleic acid and also contains at least one base X which can be recognized by endonuclease V);

(b) a step for forming a double-stranded nucleic acid from the primer annealed to the template nucleic acid in the step (a), by synthesizing a primer elongation chain complementary with the template nucleic acid by a DNA polymerase;

(c) a step for providing the primer elongation chain with a new 3' end, through the recognition of a base X in the primer elongation chain of the double-stranded nucleic acid formed in the step (b) and cleavage of a phosphodiester bond positioned at a downstream side (3' side) of said base X, by endonuclease V;

(d) a step for forming a double-stranded nucleic acid and carrying out strand displacement, by synthesizing a primer elongation chain complementary with the template nucleic acid from the 3' end of primer elongation chain which is newly provided in the step (c), by a DNA polymerase having a strand displacement activity;

(e) a step for providing the primer elongation chain with a new 3' end, through the recognition of the base X in the primer elongation chain of the double-stranded nucleic acid formed in the step (d) and cleavage of a phosphodiester bond positioned at a downstream side (3' side) of said base X, by endonuclease V;

(f) a step for forming a double-stranded nucleic acid and carrying out strand displacement, by synthesizing a primer elongation chain complementary with the template nucleic acid from the 3' end of primer elongation chain which is newly provided in the step (e), with the DNA polymerase having a strand displacement activity.

An example of the schematic illustration for describing the reaction mode of present embodiment is shown in FIG. 1. As shown in FIG. 1, according to progression of the nucleic acid amplification reaction of present embodiment, synthesis of the nucleic acid chain from the primer as the starting point is repeatedly carried out and amplification of the target nucleic acid sequence is attained. According to the reaction, when cleavage of a primer chain is effected by the activity of endonuclease V, a vicinity position of downstream side of the base X (mainly the second phosphodiester bond of the 3' side of the base X) is cleaved so that the base X is not eliminated from the primer chain by said cleavage.

According to the nucleic acid amplification method of the present invention, it is preferable that the endonuclease V does not cleave a phosphodiester bond which is present in a complementary chain in the vicinity of the base X. Because of the ability of said endonuclease V, it becomes possible to repeatedly provide the 3' end which becomes the starting point of elongation by the DNA polymerase during the nucleic acid amplification reaction. Based on this, the amplification product is accumulated with the lapse of the reaction time, theoretically from at least one molecule of the nucleic acid as the template via at least one molecule of the primer. The reaction continues without stopping in theory but eventually stops in reality due to concentration lowering or depletion of various components (e.g., a DNA synthesis substrate and the like) or decrease or inactivation of enzymes during the nucleic acid amplification reaction.

Depletion of primer which can occur in the PCR and other several amplification methods does not occur theoretically in the nucleic acid amplification method of the present invention. According to the preferred embodiment of the present invention, it is not always necessary to continue the nucleic acid amplification reaction until it stops, and the reaction may be carried out for a period of time sufficient for attaining the desired amplification. From FIG. 1, it can be understood that the amplification product is linear functionary accumulated in present embodiment. In this connection, although a case in which the template nucleic acid is single-stranded is shown in FIG. 1, the template nucleic acid may be double-stranded actually.

(2) Embodiment 2

A Case of Using a First Primer and a Second Primer

A preferable embodiment of the present invention is a nucleic acid amplification method which comprises the following steps (a) to (l) wherein the steps (c) to (f) and steps (i) to (l) are continuously repeated:

(a) a step for allowing at least one kind of a first primer to cause annealing to a template nucleic acid (wherein said primer is an oligonucleotide primer which has a nucleotide sequence substantially complementary with the nucleotide sequence of a template nucleic acid and also contains at least one base X which can be recognized by endonuclease V);

(b) a step for forming a double-stranded nucleic acid from the first primer annealed to the template nucleic acid in the step (a), by synthesizing a primer elongation chain complementary with the template nucleic acid by a DNA polymerase;

(c) a step for providing the primer elongation chain with a new 3' end, through the recognition of a base X in the first primer elongation chain of the double-stranded nucleic acid formed in the step (b) and cleavage of a phosphodiester bond positioned at a downstream side (3' side) of said base X, by endonuclease V;

(d) a step for forming a double-stranded nucleic acid and carrying out strand displacement, by synthesizing a primer elongation chain complementary with the template nucleic acid from the 3' end of primer elongation chain which is newly provided in the step (c), with a DNA polymerase having a strand displacement activity;

(e) a step for providing the primer elongation chain with a new 3' end, through the recognition of the base X in the first primer elongation chain of the double-stranded nucleic acid formed in the step (d) and cleavage of a phosphodiester bond positioned at a downstream side (3' side) of said base X, by endonuclease V;

(f) a step for forming a double-stranded nucleic acid and carrying out strand displacement, by synthesizing a primer elongation chain complementary with the template nucleic acid from the 3' end of the first primer elongation chain which newly provided in the step (e), with the DNA polymerase having a strand displacement activity;

(g) a step for using the nucleic acid released by the strand displacement in the step (d) or (f) as the template nucleic acid and allowing at least one kind of a second primer to cause annealing to said template nucleic acid wherein said primer is an oligonucleotide primer which has a nucleotide sequence substantially complementary with the nucleotide sequence of a template nucleic acid and also contains at least one base X which can be recognized by endonuclease V;

(h) a step for forming a double-stranded nucleic acid from the second primer chain annealed to the template nucleic acid in the step (g), by synthesizing a primer elongation chain complementary with the template nucleic acid by a DNA polymerase;

(i) a step for providing the primer elongation chain with a new 3' end, through the recognition of a base X in the second primer elongation chain of the double-stranded nucleic acid formed in the step (f) and cleavage of a phosphodiester bond positioned at a downstream side (3' side) of said base X, by endonuclease V;

(j) a step for forming a double-stranded nucleic acid and carrying out strand displacement, by synthesizing a primer elongation chain complementary with the template nucleic acid from the 3' end of the second primer elongation chain which newly provided in the step (i), with a DNA polymerase having a strand displacement activity;

(k) a step for providing the primer elongation chain with a new 3' end, through the recognition of the base X in the second primer elongation chain of the double-stranded nucleic acid formed in the step (j) and cleavage of a phosphodiester bond positioned at a downstream side (3' side) of said base X, by endonuclease V;

(l) a step for forming a double-stranded nucleic acid and carrying out strand displacement, by synthesizing a primer elongation chain complementary with the template nucleic acid from the 3' end which is newly provided to the primer elongation chain in the step (k), by the DNA polymerase having a strand displacement activity.

Figure 2:
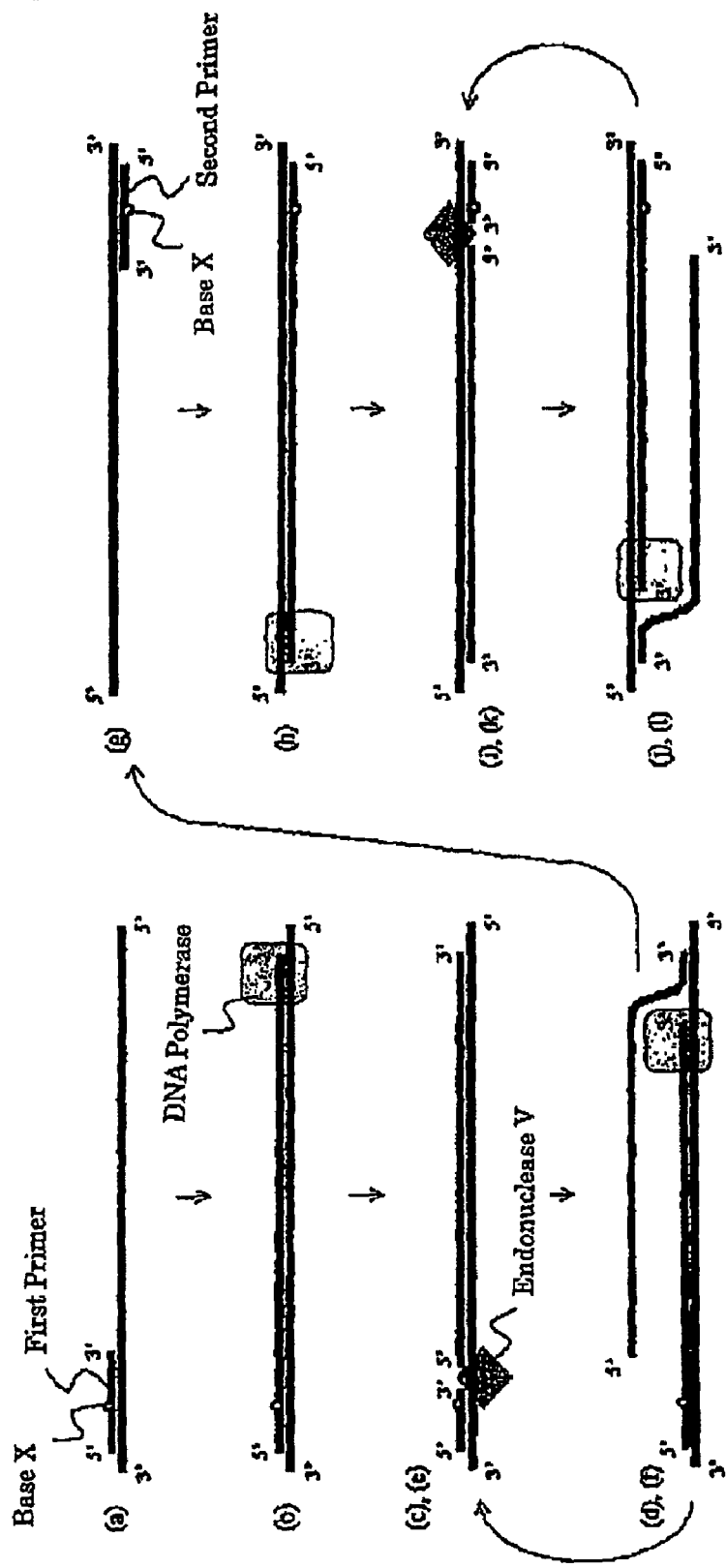
FIG. 2 shows a schematic illustration to be used for the description of a nucleic acid amplification method which uses a first primer and a second primer as an embodiment of the present invention.

An example of the schematic illustration for describing the reaction mode of present embodiment is shown in FIG. 2. In the case of using a first primer and a second primer as shown in FIG. 2, according to progression of the nucleic acid amplification reaction of present embodiment, synthesis of the nucleic acid chain from the primers as the starting points is repeatedly carried out and amplification of the target nucleic acid sequence is thereby attained. Additionally, according to this reaction, synthesis of a nucleic acid chain from the first primer as the starting point and synthesis of a nucleic acid chain from the second primer as the starting point are respectively carried out repeatedly and amplification of the target nucleic acid sequence is attained. According to the embodiment, the amplification product is accumulated with the lapse of the reaction time, theoretically from at least one molecule of the template nucleic acid via at least one molecule of the first primer and at least one molecule of the second primer.

Also in the case of the present embodiment, the nucleic acid amplification is continued without stopping in theory. Additionally, theoretically, depletion of primer does not occur with the advance of the nucleic acid amplification reaction, regarding both of the first primer and second primer.

It can be understood from FIG. 2 that, in the present embodiment, the amplification product formed from the first primer as the starting point of the synthesis and the amplification product formed from the second primer as the starting point of the synthesis have mutually complementary nucleic acid sequences. Accordingly, it can be understood that the mutually complementary nucleic acid sequences of these amplification products can form a double-strand during the nucleic acid amplification reaction. Namely, it can be understood that the amplification products of the present embodiment can be present as a double-stranded nucleic acid.

(3) Embodiment 3

A Case of Using a First Primer and a Second Primer

A preferable embodiment of the present invention is a nucleic acid amplification method which comprises the following steps (a) to (y) wherein the steps (c) to (f), (i) to (l) and (m) to (y) are continuously repeated. According to the present embodiment, it is possible to effect re-annealing of nucleic acid sequence of the first primer to the nucleic acid chain released by the strand displacement reaction in the following steps (j) and (l) where the second primer chain is elongated:

(a) a step for allowing at least one kind of a first primer to cause annealing to a template nucleic acid (wherein said primer is an oligonucleotide primer which has a nucleotide sequence substantially complementary with the nucleotide sequence of a template nucleic acid and also contains at least one base X which can be recognized by endonuclease V);

(b) a step for forming a double-stranded nucleic acid from the first primer annealed to the template nucleic acid in the step (a), by synthesizing a primer elongation chain complementary with the template nucleic acid with a DNA polymerase;

(c) a step for providing the primer elongation chain with a new 3' end, through the recognition of a base X in the first primer elongation chain of the double-stranded nucleic acid formed in the step (b) and cleavage of a phosphodiester bond positioned at a downstream side (3' side) of said base X, by endonuclease V;

(d) a step for forming a double-stranded nucleic acid and carrying out strand displacement, by synthesizing a primer elongation chain complementary with the template nucleic acid from the 3' end of primer elongation chain which is newly provided in the step (c), with a DNA polymerase having a strand displacement activity;

(e) a step for providing the primer elongation chain with a new 3' end, through the recognition of the base X in the first primer elongation chain of the double-stranded nucleic acid formed in the step (d) and cleavage of a phosphodiester bond positioned at a downstream side (3' side) of said base X, by endonuclease V;

(f) a step for forming a double-stranded nucleic acid and carrying out strand displacement, by synthesizing a primer elongation chain complementary with the template nucleic acid from the 3' end of the first primer elongation chain which is newly provided in the step (e), by the DNA polymerase having a strand displacement activity;

(g) a step for using the nucleic acid released by the strand displacement in the step (d) or (f) as the template nucleic acid and allowing at least one kind of a second primer to cause annealing to said template nucleic acid wherein said primer is an oligonucleotide primer which has a nucleotide sequence substantially complementary with the nucleotide sequence of a template nucleic acid and also contains at least one base X which can be recognized by endonuclease V;

(h) a step for forming a double-stranded nucleic acid from the second primer chain annealed to the template nucleic acid in the step (g), by synthesizing a primer elongation chain complementary with the template nucleic acid by a DNA polymerase;

(i) a step for providing the primer elongation chain with a new 3' end, through the recognition of a base X in the second primer elongation chain of the double-stranded nucleic acid formed in the step (f) and cleavage of a phosphodiester bond positioned at a downstream side (3' side) of said base X, by endonuclease V;

(j) a step for forming a double-stranded nucleic acid and carrying out strand displacement, by synthesizing a primer elongation chain complementary with the template nucleic acid from the 3' end of the second primer elongation chain which is newly provided in the step (i), with a DNA polymerase having a strand displacement activity;

(k) a step for providing the primer elongation chain with a new 3' end, through the recognition of the base X in the second primer elongation chain of the double-stranded nucleic acid formed in the step (j) and cleavage of a phosphodiester bond positioned at a downstream side (3' side) of said base X, by endonuclease V;

(l) a step for forming a double-stranded nucleic acid and carrying out strand displacement, by synthesizing a primer elongation chain complementary with the template nucleic acid from the 3' end which is newly provided to the primer elongation chain in the step (k), by the DNA polymerase having a strand displacement activity;

(m) a step for using the nucleic acid released by the strand displacement in the step (j) or (l) as the template nucleic acid and allowing the first primer described in the step (a) to anneal to said template nucleic acid;

(n) a step for forming a double-stranded nucleic acid from the first primer annealed to the template nucleic acid in the step (m), by synthesizing an elongation chain complementary with the template nucleic acid by a DNA polymerase;

(o) a step for providing the primer elongation chain with a new 3' end, through the recognition of a base X in the first primer elongation chain of the double-stranded nucleic acid formed in the step (n) and cleavage of a phosphodiester bond positioned at a downstream side (3' side) of said base X, by endonuclease V;

(p) a step for forming a double-stranded nucleic acid and carrying out strand displacement, by synthesizing a primer elongation chain complementary with the template nucleic acid from the 3' end which is newly provided to the first primer elongation chain in the step (o), with a DNA polymerase having a strand displacement activity;

(q) a step for providing the primer elongation chain with a new 3' end, through the recognition of the base X in the first primer elongation chain of the double-stranded nucleic acid formed in the step (p) and cleavage of a phosphodiester bond positioned at a downstream side (3' side) of said base X, by endonuclease V;

(r) a step for forming a double-stranded nucleic acid and carrying out strand displacement, by synthesizing a primer elongation chain complementary with the template nucleic acid from the 3' end newly provided to the first primer elongation chain in the step (q), by the DNA polymerase having a strand displacement activity;

(s) a step for using the nucleic acid released by the strand displacement in the step (p) or (r) as the template nucleic acid and allowing the second primer described in the step (g) to anneal to said template nucleic acid;

(t) a step for forming a double-stranded nucleic acid from the second primer annealed to the template nucleic acid in the step (s), by synthesizing an elongation chain complementary with the template nucleic acid by a DNA polymerase;

(u) a step for providing the primer elongation chain with a new 3' end, through the recognition of a base X in the primer elongation chain of the double-stranded nucleic acid formed in the step (t) and cleavage of a phosphodiester bond positioned at a downstream side (3' side) of said base X, by endonuclease V;

(v) a step for forming a double-stranded nucleic acid and carrying out strand displacement, by synthesizing a primer elongation chain complementary with the template nucleic acid from the 3' end which is newly provided to the primer elongation chain in the step (u), by a DNA polymerase having a strand displacement activity;

(w) a step for providing the primer elongation chain with a new 3' end, through the recognition of the base X in the primer elongation chain of the double-stranded nucleic acid formed in the step (v) and cleavage of a phosphodiester bond positioned at a downstream side (3' side) of said base X, by endonuclease V;

(x) a step for forming a double-stranded nucleic acid and carrying out strand displacement, by synthesizing a primer elongation chain complementary with the template nucleic acid from the 3' end of the primer elongation chain which is newly provided in the step (w), by the DNA polymerase having a strand displacement activity;

(y) a step for using the nucleic acid released by the strand displacement in the step (v) or (x) as the template nucleic acid in the step (m).

Figure 3:
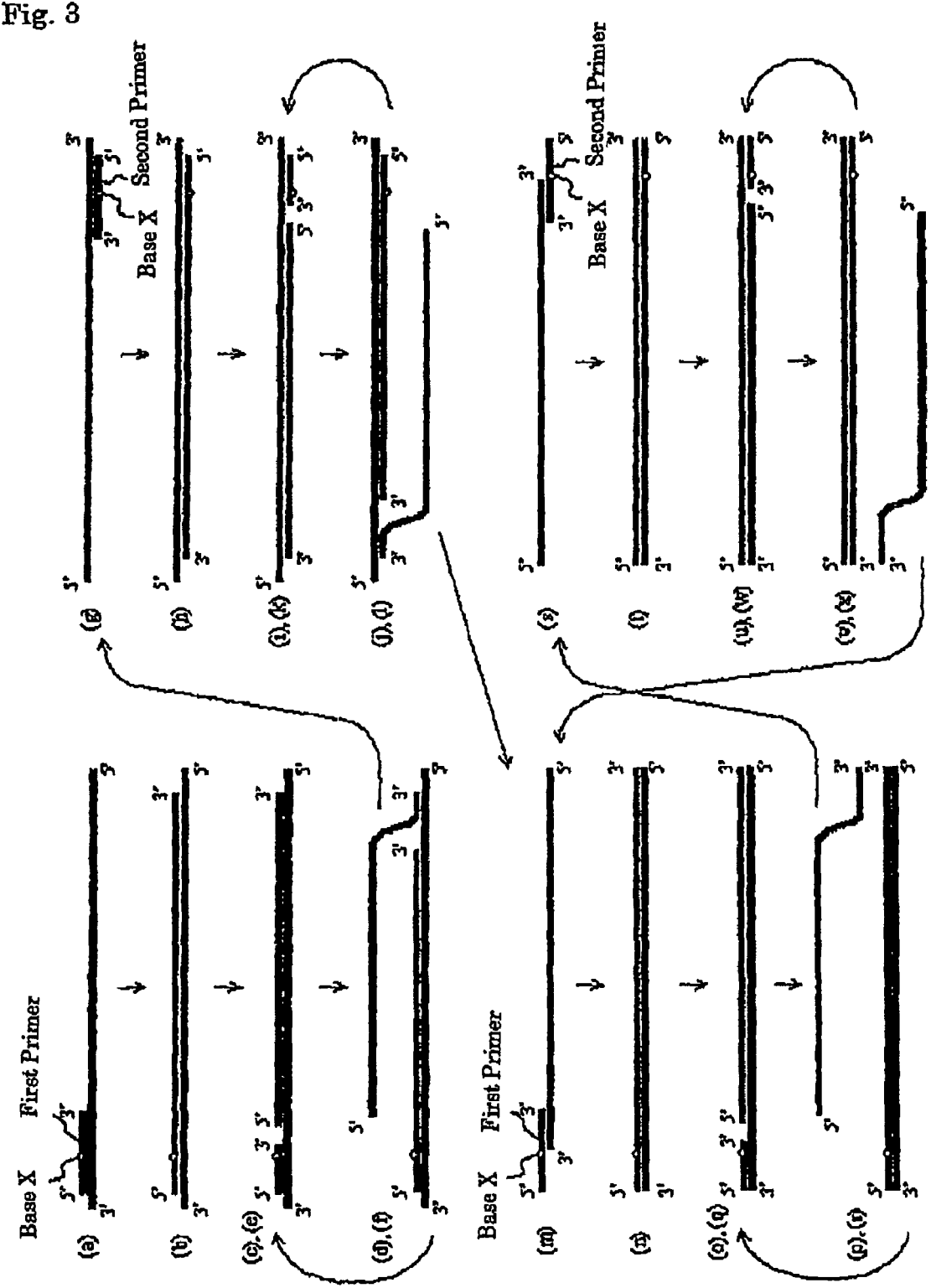
FIG. 3 shows a schematic illustration to be used for the description of a nucleic acid amplification method which uses a first primer and a second primer as an embodiment of the present invention.

An example of the schematic illustration for describing the reaction mode of present embodiment is shown in FIG. 3. In FIG. 3, the figures representing endonuclease V and strand displacement type DNA polymerase are omitted. In the present embodiment, not only the same mode of amplification reaction of the embodiment previously described together with FIG. 2 (namely the steps (a) to (l)) occurs, but also a chain cycle of additional nucleic acid chain synthesis (namely the steps (m) to (y)) is further produced. It can be understood from FIG. 3 that amplification of the target nucleic acid sequence in the present embodiment is achieved, theoretically, from at least one molecule of the template nucleic acid via the annealing of at least two molecules or more of the first primer and at least two molecules or more of the second primer.

Also in the case of the present embodiment, ideally, the reaction is continued without stopping. Also, theoretically, depletion of primer does not occur with the progression of the reaction, regarding both of the first primer and second primer. Additionally, also in the present embodiment, the amplification product formed from the first primer as the starting point of the synthesis and the amplification product formed from the second primer as the starting point of the synthesis have mutually complementary nucleic acid sequences. Accordingly, it is possible that the mutually complementary nucleic acid sequences of these amplification products form a double-strand during the reaction, so that the amplification products can be present as a double-stranded nucleic acid.

In this connection, although a case in which the template nucleic acid is a single strand is shown in FIG. 2 and FIG. 3 for the sake of conveniently describing the reaction modes, in reality, the template nucleic acid may be a double strand. When the template nucleic acid is a double strand, the amplification reaction described by FIG. 2 and FIG. 3 occurs on each of the chains constituting said double strand. Namely, although the amplification reaction described using FIG. 2 and FIG. 3 occurs on one chain of said double-stranded template as already described, on the other chain of said template, it can be understood that the amplification reaction occurs in the same manner when the aforementioned first primer is newly regarded as a second primer and the aforementioned second primer is newly regarded as a first primer, in the aforementioned descriptions by FIG. 2 and FIG. 3. Accordingly, any one of the two kinds of primers can be regarded as the first primer, and the amplification reaction which occurs on each chain of the double-stranded template is included in the embodiments of the nucleic acid amplification method of the present invention.

Figure 4:
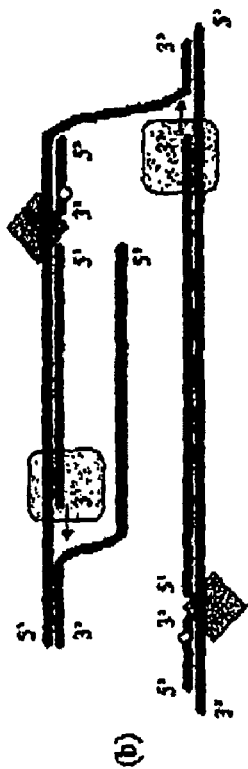
FIG. 4 shows a schematic illustration to be used for the description of a nucleic acid amplification method in which two or three of a specific annealing of a primer to the target nucleic acid, an elongation chain synthesis reaction or strand displacement reaction by a DNA polymerase and a cleavage reaction of phosphodiester bond by endonuclease V are carried out on the same template nucleic acid, as an embodiment of the present invention.
Figure 4:
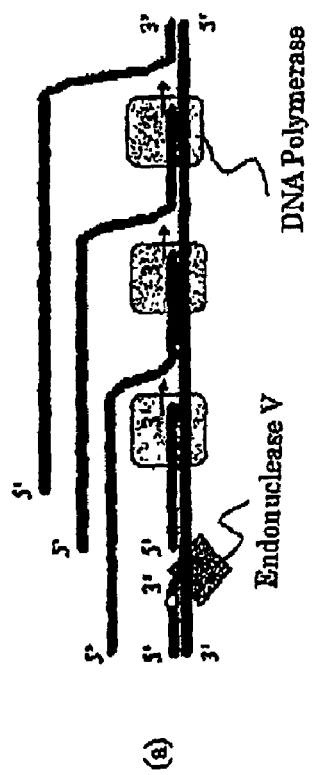

Although FIGS. 1 to 3 are schematic illustrations in which the respective steps are shown by stages for the sake of conveniently describing the reaction modes of the embodiments of the present invention, it is obvious that respective steps can occur simultaneously and frequently in the real reactions. An example of such a case is schematically shown in FIG. 4. FIG. 4(a) schematically shows a state in which cleavage by endonuclease V and two or more elongation reactions of DNA polymerase are occurring on the same template molecule. Also, FIG. 4(b) schematically shows a state in which annealing of primer, cleavage by endonuclease V and elongation reaction and strand displacement reaction by DNA polymerase are occurring on the complementary chain replaced by the template. The range of the present invention is not limited to the example shown in FIG. 4, and all of the possible examples are not shown therein. However, according to the preferable embodiment of the present invention, two or more of plural steps such as annealing of primer, cleavage by endonuclease V and elongation reaction and strand displacement reaction by DNA polymerase and the like can occur on the same template molecule during the nucleic acid amplification.

Additionally, in the embodiments shown in FIG. 2 and FIG. 3 which use a first primer and a second primer, the elongation and strand displacement by DNA polymerase using the first primer as the starting point and the elongation and strand displacement by DNA polymerase using the second primer as the starting point can occur on the same template molecule simultaneously or almost simultaneously in mutually facing directions. An example of such a case is schematically shown in FIG. 5 (in this case, the figure representing the strand displacement type DNA polymerase is omitted in FIG. 5).

FIGS. 5(a) and (b) schematically show a state in which the elongation and strand displacement by DNA polymerase are occurring on the same template molecule from both sides in mutually facing directions. In such a case, so-called "template exchange reaction" (template switching reaction), in which one template of the elongation chains is switched to the other template of the elongation chains in the middle of the synthesis of said elongation chains, can occur at a certain probability. FIG. 5(c) schematically shows the template switching reaction, and FIG. 5(d) schematically shows a state in which elongation by the DNA polymerase proceeded after the template switching reaction. An embodiment of the present invention is a method for amplifying a nucleic acid sequence, which accompanies the template switching reaction during the amplification reaction.

The aforementioned "template switching reaction" means a reaction in which, when synthesis of complementary chains by the strand displacement reaction is carried out from both sides of a double-stranded nucleic acids, one DNA polymerase changes its template, and the other DNA polymerase carries out the subsequent complementary chain synthesis using the newly synthesized complementary chains respectively as the templates. Namely, it means a reaction in which, in a reaction for forming elongation chains complementary with a double-stranded nucleic acid to be used as the template nucleic acid by treating said template nucleic acid with respective primers and a DNA polymerase having a strand displacement activity, the DNA polymerase actively switches the template from the original template of one primer elongation chain to the other primer elongation chain during synthesis of said primer elongation chains. The possibility of generating such a reaction under a certain condition is conventionally known and disclosed, for example, in International Publication 02/16639, "Development of a progressive isothermal gene amplification method (ICAN method)" (Takara Shuzo Co., Ltd. News Release, Sep. 25, 2000) and the like.

Figure 5:
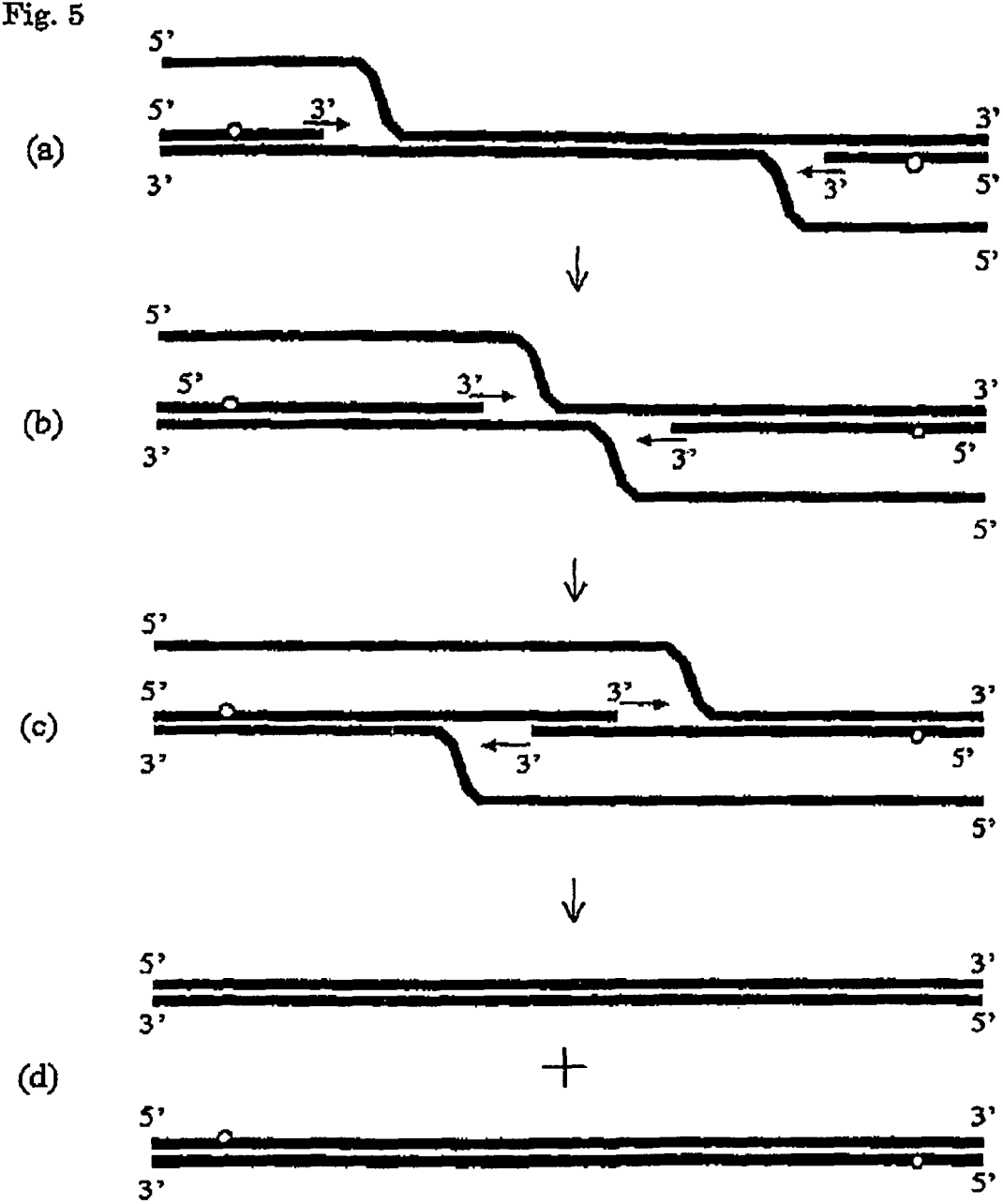
FIG. 5 shows a schematic illustration to be used for the description of a template switching reaction in an embodiment of the nucleic acid amplification method of the present invention.

In the above-mentioned embodiment which uses a first primer and a second primer, in addition to the reaction mode shown in FIG. 2, a chain cycle of further additional nucleic acid chain synthesis (namely the steps (m) to (y)) can occur, and/or the template switching reaction shown in FIG. 5 can occur, so that it can be understood that exponential accumulation of the amplification product is possible in the preferable embodiment. Additionally, in the preferable embodiment of the present invention which uses a first primer and a second primer, the main amplification product becomes a DNA fragment having a predictable length based on the positions where the two primers anneal to the template nucleic acid.

The following describes the respective reaction components to be used in the present invention and the reaction conditions further in detail.

2. Endonuclease V

Although the endonuclease V to be used in the present invention may be any organism- or virus-derived one, a bacterium-derived or archaebacterium-derived one can for example be selected. Examples thereof include those which are derived from *Escherichia coli, Salmonella typhimurium, Thermotoga maritima, Thermus thermophilus, Thermoplasma acidophilum, Thermoplasma volcanium, Aeropyrum pernix, Pyrococcus abyssi, Pyrococcus horikoshii, Sulfolobus tokodaii, Archaeoglobus fulgidus* and the like. Additionally, the endonuclease V to be used in the present invention may be either a substance prepared by purifying from its natural origin or a recombinant protein produced by genetic engineering.

As the endonuclease V to be used in the present invention, those which are broadly and generally on the market can be used. For example, *Escherichia coli* endonuclease V is put on the market by Trevigen and New England Biolabs. Also, *Thermotoga maritima* endonuclease V is put on the market by Fermentas.

Additionally, the endonuclease V to be used in the present invention may be a result of adding substitution, deletion, addition, insertion and the like modifications by genetic engineering or other means. Example of such an endonuclease V include the mutation type endonuclease V disclosed in JP-A-2007-111017 or the like.

The "specific nucleic acid cleavage activity" of the endonuclease V according to the present invention means an activity of said enzyme to recognize a specific nucleotide or base or a specific structure such as deoxyinosine or the base thereof (hypoxanthine), deoxyuridine or the base thereof (uracil), the base of deoxyxanthosine (xanthine), the base of deoxyoxanosine (oxanine), AP site (apurinic/apyrimidinic site or abasic site), mismatch of bases, insertion/deletion of base, flap structure or pseudo-Y structure, a derivative of any one of intact bases which can be found in natural DNA (adenine, thymine, guanine, cytosine) or a nucleotide residue containing the derivative and the like, which are contained in nucleic acid molecules, and to cleave a phosphodiester bond in the vicinity of the recognition site. For example, in the case of a "deoxyinosine-specific nucleic acid cleavage activity" of endonuclease V, it means a nucleic acid cleavage activity which accompanies specific recognition of deoxyinosine or the base thereof (hypoxanthine) by said enzyme, among the aforementioned specific nucleic acid cleavage activities.

The "nonspecific nucleic acid cleavage activity" of the endonuclease V according to the present invention means a nucleic acid cleavage activity of said enzyme, which is not included in the aforementioned "specific nucleic acid cleavage activity". For example, a random nicking activity of DNA chain and the like are included in it. Such an activity of endonuclease V is disclosed for example in International Publication 2004/046383.

Among the specific nucleic acid cleavage activities of endonuclease V, the endonuclease V to be used in the present invention may have a specific nucleic acid cleavage activity for at least one kind of base. For example, it may have a specific nucleic acid cleavage activity for at least one kind among the base of deoxyinosine (hypoxanthine), the base of deoxyuridine (uracil), the base of deoxyxanthosine (xanthine), the base of deoxyoxanosine (oxanine) and the AP site (apurinic/apyrimidinic site or abasic site).

An example of the specific activity of the endonuclease V to be used in the present invention is a deoxyinosine-specific or deoxyuridine-specific nucleic acid cleavage activity. Thus, when the endonuclease V to be used in the present invention has the aforementioned at least one kind of specific nucleic acid cleavage activity, its other activities may be disappeared caused by modifications such as the substitution, deletion, addition, insertion and the like by genetic engineering or other means, or as a natural property.

Although the endonuclease V to be used in the present invention may have a nonspecific nucleic acid cleavage activity, an endonuclease V which does not show nonspecific nucleic acid cleavage activities but shows a specific nucleic acid cleavage activity is preferable. As examples of such an endonuclease V, there are a mutation type endonuclease V and the like disclosed in Japanese Patent Application 2005-308533. An example of the mutation type endonuclease V to be used in the present invention is a mutation type endonuclease V which has a deoxyinosine-specific nucleic acid cleavage activity as the specific nucleic acid cleavage activity.

Additionally, an example of the specific endonuclease V to be used in the present invention is a mutation type endonuclease V in which (a) the 80-position amino acid or an amino acid of a position equivalent to the 80-position of *Thermotoga maritima* endonuclease V is mutated to an other amino acid $Z_1$, and (b) the 105-position amino acid or an amino acid of a position equivalent the 105-position of *Thermotoga maritima* endonuclease V is mutated to an other amino acid $Z_2$, in the amino acid sequence of a wild type endonuclease V.

The "amino acid of a position equivalent to the 80-position of *Thermotoga maritima* endonuclease V" and "amino acid of a position equivalent to the 105-position of *Thermotoga maritima* endonuclease V" according to the present invention mean amino acids which correspond to the 80-position and 105-position amino acids of *Thermotoga maritima* endonuclease V when amino acid sequence of the endonuclease V to be used in the present invention is compared with amino acid sequence of *Thermotoga maritima* endonuclease V (e.g., GenBank Accession AAD 36927).

The aforementioned positions of amino acids can be easily calculated by comparing homology of the amino acid sequence of respective endonuclease V with the amino acid sequence of *Thermotoga maritima* endonuclease V. For example, a ready-made software (e.g., GENETYX (mfd. by Software Development)) or the like amino acid sequence homology analyzing function or the like can be used for it. In the case of the wild type endonuclease V tyrosine can for example be cited as the amino acid of a position equivalent to the 80-position of *Thermotoga maritima* endonuclease V, and aspartic acid can for example be cited as the amino acid of a position equivalent to the 105-position of *Thermotoga maritima* endonuclease V.

For example, in the case of the amino acid sequence of *Escherichia coli* endonuclease V (GenBank Accession AAC 76972), the amino acid of a position equivalent to the 80-position of *Thermotoga maritima* endonuclease V is the 75-position tyrosine, and the amino acid of a position equivalent to the 105-position of *Thermotoga maritima* endonuclease V is the 100-position aspartic acid.

For example, in the case of the amino acid sequence of *Salmonella typhimurium* endonuclease V (GenBank Accession AAL 22996), the amino acid of a position equivalent to the 80-position of *Thermotoga maritima* endonuclease V is the 73-position tyrosine, and the amino acid of a position equivalent to the 105-position of *Thermotoga maritima* endonuclease V is the 98-position aspartic acid.

For example, in the case of the amino acid sequence of *Thermus thermophilus*endonuclease V (GenBank Accession BAD 71170), the amino acid of a position equivalent to the 80-position of *Thermotoga maritima* endonuclease V is the 80-position tyrosine, and the amino acid of a position equivalent to the 105-position of *Thermotoga maritima* endonuclease V is the 105-position glutamic acid.

For example, in the case of the amino acid sequence of *Thermoplasma acidophilum* endonuclease V (GenBank Accession CAC 11602), the amino acid of a position equivalent to the 80-position of *Thermotoga maritima* endonuclease V is the 183-position tyrosine, and the amino acid of a position equivalent to the 105-position of *Thermotoga maritima* endonuclease V is the 204-position aspartic acid.

For example, in the case of the amino acid sequence of *Thermoplasma volcanium* endonuclease V (GenBank Accession NP_111300), the amino acid of a position equivalent to the 80-position of *Thermotoga maritima* endonuclease V is the 178-position tyrosine, and the amino acid of a position equivalent to the 105-position of *Thermotoga maritima* endonuclease V is the 199-position threonine.

For example, in the case of the amino acid sequence of *Aeropyrum pernix* endonuclease V (GenBank Accession NP_147286), the amino acid of a position equivalent to the 80-position of *Thermotoga maritima* endonuclease V is the 43-position tyrosine, and the amino acid of a position equivalent to the 105-position of *Thermotoga maritima* endonuclease V is the 68-position aspartic acid.

For example, in the case of the amino acid sequence of *Pyrococcus abyssi*endonuclease V (GenBank Accession NP_127057), the amino acid of a position equivalent to the 80-position of *Thermotoga maritima* endonuclease V is the 67-position tyrosine, and the amino acid of a position equivalent to the 105-position of *Thermotoga maritima* endonuclease V is the 90-position aspartic acid.

For example, in the case of the amino acid sequence of *Pyrococcus horikoshii* endonuclease V (GenBank Accession O 58394), the amino acid of a position equivalent to the 80-position of *Thermotoga maritima* endonuclease V is the 67-position tyrosine, and the amino acid of a position equivalent to the 105-position of *Thermotoga maritima* endonuclease V is the 90-position aspartic acid.

For example, in the case of the amino acid sequence of *Sulfolobus tokodaii* endonuclease V (GenBank Accession Q974T1), the amino acid of a position equivalent to the 80-position of *Thermotoga maritima* endonuclease V is the 70-position tyrosine, and the amino acid of a position equivalent to the 105-position of *Thermotoga maritima* endonuclease V is the 93-position aspartic acid.

For example, in the case of the amino acid sequence of *Magnetospirillum magnetotacicum* endonuclease V (GenBank Accession ZP_00051831), the amino acid of a position equivalent to the 80-position of *Thermotoga maritima* endonuclease V is the 81-position tyrosine. Regarding the amino acid of a position equivalent to the 105-position of *Thermotoga maritima* endonuclease V, the 106-position aspartic acid is the amino acid of said position.

When a mutation is applied to (a) the 80-position amino acid or an amino acid of a position equivalent to the 80-position of *Thermotoga maritima* endonuclease V and (b) the 105-position amino acid or an amino acid of a position equivalent the 105-position of *Thermotoga maritima* endonuclease V in the amino acid sequence of the wild type endonuclease V, the amino acid after replacement may be any amino acid.

As the amino acid $Z_1$ which replaces the 80-position amino acid or an amino acid of a position equivalent to the 80-position of *Thermotoga maritima* endonuclease V in the amino acid sequence of the wild type endonuclease V, for example, alanine, glycine, leucine, isoleucine, valine, phenylalanine, methionine and the like are preferable, and alanine is more preferable. As the amino acid $Z_2$ which replaces the 105-position amino acid or an amino acid of a position equivalent the 105-position of *Thermotoga maritima* endonuclease V in the amino acid sequence of the wild type endonuclease V, for example, alanine, glutamic acid, asparagine, glutamine, arginine, glycine, serine, threonine, histidine and the like are preferable, and alanine, glutamic acid, asparagine and glutamine are more preferable.

The wild type endonuclease V as the origin of the mutation type endonuclease V to be used in the present invention may be any organism- or virus-derived one, and a bacterium-derived one and an archaebacterium-derived one can for example be selected. Examples of the bacterium-derived one or archaebacterium-derived endonuclease V include the endonuclease V derived from *Escherichia coli, Salmonella typhimurium, Thermotoga maritima, Thermus thermophilus, Thermoplasma acidophilum, Thermoplasma volcanium, Aeropyrum pernix, Pyrococcus abyssi, Pyrococcus horikoshii, Sulfolobus tokodaii, Archaeoglobus fulgidus* and the like. Examples of preferable examples of the bacterium-derived or archaebacterium-derived wild type endonuclease V include those which are derived from thermophilic bacteria or thermophilic archaebacteria, and a *Thermotoga maritima*-derived one is further preferable. Additionally, preferable examples of a mesophilic bacterium-derived wild type endonuclease V as the origin of the mutation type endonuclease V include those which are derived from *Escherichia coli*.

The optimum temperature of every specific activity of the endonuclease V to be used in the present invention may be any temperature, and the endonuclease V to be used in the present invention may for example be an endonuclease V which has "heat resistance". According to the present invention, the term, an enzyme has "heat resistance", means that the optimum temperature for showing the activity of the enzyme is a temperature higher than the ordinary temperature range (from 20 to 40° C.). For example, it means that the optimum temperature for showing the activity of the enzyme is a temperature higher than a mildly high temperature range (from 45 to 65° C.), high temperature range (from 60 to 80° C.) or ultra-high temperature range (80° C. or more or 90° C. or more).

A suitable example of the mutation type specific endonuclease V to be used in the present invention is an endonuclease V which has the amino acid sequence shown in SEQ ID NO:2.

3. Base X

Figure 6:
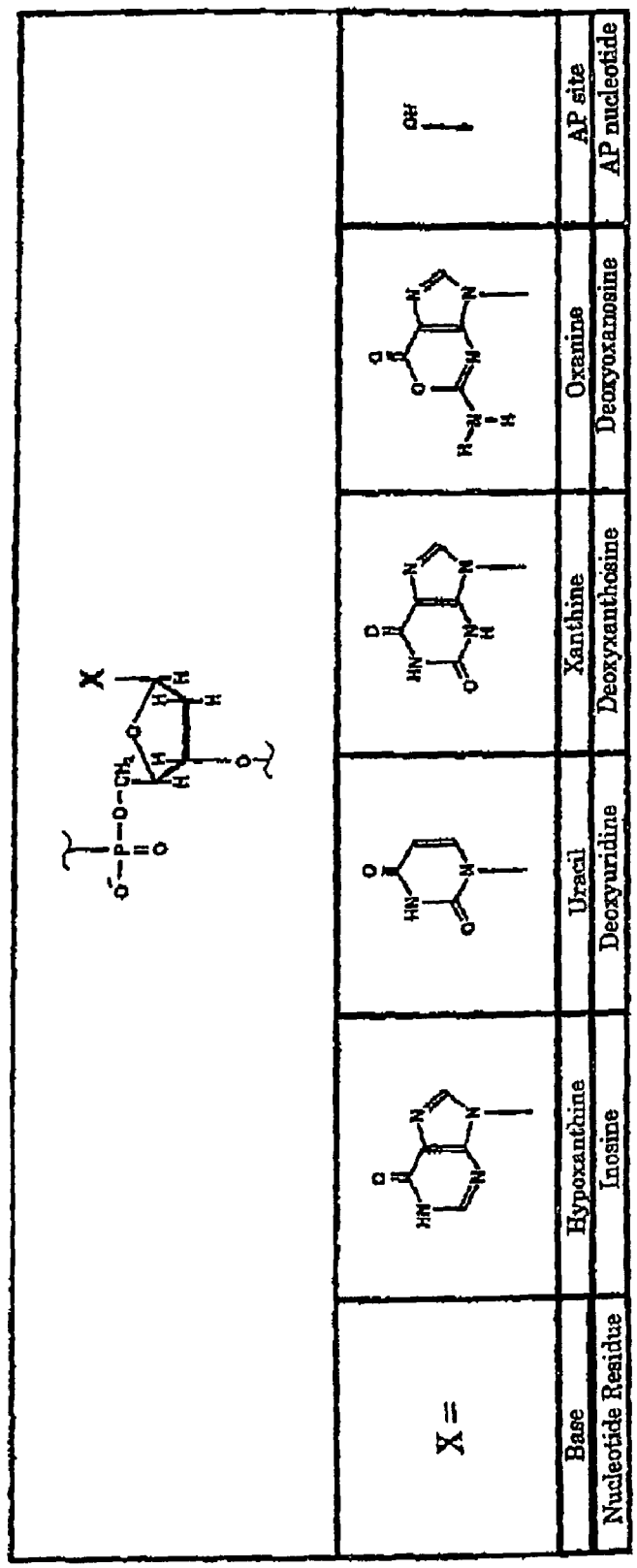
FIG. 6 is an illustration showing examples of the base X and nucleotide residue (in the case of deoxyribonucleotide) having the base X to be used in the present invention.

The primer to be used in the nucleic acid amplification method of the present invention is an oligonucleotide primer which contains at least one base which can be recognized by the endonuclease V. Although the base X according to the present invention may be any substance which can be recognized by the endonuclease V to be used, examples thereof include hypoxanthine (the base of deoxyinosine), uracil (the base of deoxyuridine), xanthine (the base of deoxyxanthosine), oxanine (the base of deoxyoxanosine), AP site (apurinic/apyrimidinic site or abasic site) or a derivative of any one of intact bases which can be found in natural DNA (adenine, thymine, guanine, cytosine) and the like. Structures of some suitable examples of the base X according to the present invention are shown in FIG. 6.

The base X according to the present invention can be suitably included in the oligonucleotide primer by optionally using enzymatic methods, chemical methods or other conventionally known methods. Particularly, similar to the other ordinary bases (adenine, thymine, guanine, cytosine and the like), it is possible to include hypoxanthine and uracil in the primer at optional positions by a chemical primer synthesis technique which is generally carried out by those skilled in the art (e.g., phosphoamidite method or the like).

The base X according to the present invention may be a base which is complementary with the template nucleic acid. Additionally, in case where the oligonucleotide primer to be used in the present invention is substantially complementary with the template nucleic acid, the base X in the present invention may not be complementary with the template nucleic acid, but can form a mismatch. Since it is known that hypoxanthine does not form mismatch with any base, it can be suitably used as the base X of the present invention.

4. Oligonucleotide Primer

The oligonucleotide primer to be used in the present invention is an oligonucleotide primer which has a nucleotide sequence substantially complementary with the nucleotide sequence of the template nucleic acid and also contains at least one base X which can be recognized by endonuclease V. The oligonucleotide primer to be used in the present invention is preferably constituted by a deoxyribonucleotide. Additionally, the oligonucleotide primer to be used in the present invention may contain one or more ribonucleotides. It is preferable that the oligonucleotide primer to be used in the present invention has a 3'—OH group on said 3' end in order to make elongation of DNA chain from the 3' end possible. However, said 3'—OH group is not essential, since the nucleic acid cleavage activity of the endonuclease V has the ability to provide the primer chain with a new 3'—OH group in the preferable embodiment of the present invention.

The oligonucleotide primer to be used in the present invention can be synthesized by for example the phosphoamidite method, phosphotrimester method, H-phosphonate method, thiophosphonate method or the like, using for example a commercially available automatic DNA synthesizer.

The oligonucleotide primer to be used in the present invention is generally designed in such a manner that it can be annealed to the template nucleic acid by such a positional relation that the region to be amplified is set on the downstream side looking from said primer. Said primer is designed in such a manner that it is substantially complementary for the nucleotide sequence of the region to which it is going to be annealed. Regarding the designing of said primer, those skilled in the art can design it by almost the same means for the designing of primers for PCR use (and primers of other amplification methods). In general, it is conventionally known to those skilled in the art that there is a case in which a primer having a nucleotide sequence in the nucleotide sequence of the primer, that can form a base pair between primers and inside the primer under the conditions to be used, is not preferable. Also, techniques for designing a primer having a preferable nucleotide sequence by avoiding or minimizing such an unpreferable nucleotide sequence is conventionally known to those skilled in the art.

Additionally, it is preferable that the oligonucleotide primer to be used in the present invention has such a nucleotide sequence that the nucleotide sequence substantially complementary with the nucleotide sequence of the template nucleic acid can anneal to the template nucleic acid under the conditions to be used. Such a nucleotide sequence can be designed, for example, based on the melting temperature, GC content, nucleotide sequence information, length and the like of said sequence under the conditions to be used, and said techniques are conventionally known to those skilled in the art. In the designing of a desired primer nucleotide sequence, for example, it can be designed by referring to "Bio Jikken Illustrated Volume 3" (edited by Haruki Suma, Saibo Kogaku Supplement, edited by Haruki Suma, published by Shujunsha, 1996, p. 13-59) and the like. For example, a commercially available primer designing software such as OLIGO Primer Analysis Software (mfd. by Takara Shuzo) and the like can be used.

In designing the primer to be used in the present invention, although it is preferable that the nucleotide sequence of the region on the template nucleic acid where the primer is annealed is already known, nucleotide sequences of regions other than said region on the template nucleic acid are not necessarily already known. Additionally, even when the nucleotide sequence of the region on the template nucleic acid where the primer is annealed is not completely known, it may be enough when information which is necessary for designing a primer substantially complementary with said region is available. For example, the nucleotide sequence of said region may have a possibility of mutations such as unknown substitution, deletion, addition, insertion and the like, or there is a case in which it may be an analogized, predicted or presumed sequence. Namely, according to the preferable embodiment of the present invention, it is not necessary that all parts of the sequence of target nucleic acid are already known.

According to the nucleic acid amplification method of the present invention, it becomes possible to obtain an amplification product containing an unknown nucleic acid sequence from already known sequence information. For example, by the use of at least one kind of primer designed from already known sequence information, it is possible to carry out amplification of a nucleic acid containing an unknown nucleic acid sequence which is present in the direction of advancing the elongation reaction from the region where said primer is annealed. Also for example, by the use of two species of primers designed from already known sequence information, it is possible to amplify a nucleic acid containing an unknown nucleic acid sequence inside a region specified by the region where said primer is annealed.

The oligonucleotide primer to be used in the present invention may have at least one base X which can be recognized by the endonuclease V to be used. When the oligonucleotide primer to be used in the present invention contains two or more of the base X, said base X is not limited to one kind of base and may be continuously present or scattered in the primer sequence.

Regarding the oligonucleotide primer to be used in the present invention, the base X is present preferably in a part other than the 5' side regions in the nucleotide sequence of the primer which is substantially complementary with the template nucleic acid, or is present preferably in the central area or 3' side region.

Although length of the oligonucleotide primer to be used in the present invention is not particularly limited, from about 11 to 100 bases is preferable, and from about 15 to 50 bases is more preferable. Also, it is preferable that a base is not present in the downstream side (3' side) than the base X in the oligonucleotide primer to be used in the present invention, or the number of bases as the length of the downstream side (3' side) than the base X is from about 1 to 50 bases. Additionally, the length of the upstream side (5' side) than the base X is preferably from about 10 to 100 bases, more preferably from about 10 to 50 bases.

A preferable example of the oligonucleotide primer to be used in the present invention is a primer having a complete length of appropriately from 14 to 34 bases in which the downstream side length than the base X is from 1 to 3 bases and the upstream side length than the base X is from 12 to 30 bases. Additionally, another preferable example is a primer having a complete length of appropriately from 31 to 61 bases in which the downstream side length than the base X is from 15 to 30 bases and the upstream side length than the base X is from 15 to 30 bases.

In addition to the nucleotide sequence which is substantially complementary with the template nucleic acid, the oligonucleotide primer to be used in the present invention may have an additional sequence which does not anneal to the template nucleic acid, in the upstream side and/or downstream side of said sequence, within such a range that the function of said primer is not lost. For example, it may have said additional sequence in the upstream side of the nucleotide sequence of the primer which is substantially complementary with the template nucleic acid. Examples of said additional sequence include a restriction enzyme recognition sequence, a DNA binding protein recognition sequence, a sequence which is recognized by other protein or nucleic acid or by a chemical reagent, a sequence which can form a hairpin structure or stem loop structure by self annealing, or an optional nucleotide sequence, a nonsense nucleotide sequence and the like.

It is preferable that the neighboring base of the 5' side of the base X in the oligonucleotide primer to be used in the present invention is adenine or thymine or the neighboring base of the 3' side of the base X is adenine or thymine, or both cases. When such a primer is used, it is suitably cleaved by the endonuclease V, and the nucleic acid sequence is more suitably amplified.

The oligonucleotide primer to be used in the present invention may contain at least one modified nucleotide within such a range that it does not lose the function of said primer. Among the whole nucleotides in the upstream (5') side of the base X of the primer, it is preferable that the containing amount of said modified nucleotide is set to 60% or less and it is more preferable within the range of from one nucleotide to 60%. As said modified nucleotide, although it is not particularly limited, examples thereof include a nuclease-resistant modified nucleotide having such a property that it can provide resistance to the cleavage by the nuclease activity. Examples of said nuclease-resistant modified nucleotide include an ($\alpha$-S) nucleotide in which the oxygen atom binding to the α-position phosphorus atom of the nucleotide was replaced by sulfur atom, and the like. Said modified nucleotide can be contained at an optional position in the primer, by optionally using a chemical synthesis method, for example conventionally known method such as the phosphoamidite method or the like. Two or more of said modified nucleotide may be continuously present or scattered in the primer sequence.

The use of a primer containing at least one modified nucleotide which shows nuclease resistance, as the primer to be used in the present invention, is useful from the viewpoint that nonspecific cleavage of the primer and cleavage of un-annealed primer by the endonuclease V can be controlled. The primer which contains said nuclease-resistant modified nucleotide may contain at least one said modified nucleotide in both or one of the upstream side and downstream side regions of the base X. Examples of the primer containing said nuclease-resistant modified nucleotide include a primer which contains at least one said modified nucleotide in the upstream side region of the base X.

The oligonucleotide primer to be used in the present invention may also be a random primer or a degenerate primer, as long as the function of said primer is not lost.

Although kinds of the oligonucleotide primer to be used in the nucleic acid amplification method of the present invention are not particularly limited, it is preferable that one kind or two kinds of oligonucleotide primers are used. In the nucleic acid amplification method of the present invention, three or more kinds of primers may be used. For example, three or more kinds of primers which anneal to different target regions may be used. Additionally, for example, by using a group consisting of at least two species of primers as a primer set, a first primer set and a second primer set may be allowed to coexist in a reaction mixture, or three or more of primer sets may be used. Thus, according to the nucleic acid amplification method of the present invention, it is possible also to carry out multiple (multiplex) amplification.

In the nucleic acid amplification method of the present invention, an additional primer which anneals to a region of upstream side of the region to which the primer containing the base X to be used in the present invention anneals, looking from said primer, may be further used. According to the present invention, said additional primer is called "outer primer". It is preferable that the outer primer is substantially complementary for the nucleic acid sequence of the aforementioned upstream region and has 3'—OH group on its 3' end in order to make elongation of a DNA chain from said 3' end possible. In designing the outer primer, the nucleotide sequence, length ant melting temperature of said primer have no particular limitation, as long as said primer can be suitably annealed under the conditions to be used. Examples of the preferable outer primer to be used in the present invention are those in which melting temperature of said outer primer under the conditions to be used is within the range of from about +5° C. to about −10° C., more preferably within the range of from almost the same temperature to about −5° C., in comparison with the melting temperature, under the conditions to be used of the primer which contains the base X to be used in the present invention.

Preferable annealing position of the outer primer to be used in the nucleic acid amplification method of the present invention is not particularly limited as long as it is upstream than the annealing position of the primer which contains the base X. However, a position which is separated by a distance of from 0 base to about 100 bases, preferably from 0 base to about 60 bases, from the annealing position of the primer which contains said base X is preferable.

According to the nucleic acid amplification method of the present invention, although the outer primer is not essential, there is a case in which the use of the outer primer results in further favorable production of the amplification product.

The oligonucleotide primer to be used in the present invention may be modified with a fluorescence or chemiluminescence labeling, biotin labeling or the like within such a range that the function of said primer is not lost. Also, examples of another label include a radioisotope, a chromophore and the like. Additionally, examples of still another label include a substance which cannot be detected directly but becomes indirectly detectable by its reaction with a substance (e.g., avidin) which specifically binds with a label, such as a hapten, an antibody and the like.

Additionally, the oligonucleotide primer to be used in the present invention may be linked by itself to a solid phase within such a range that the function of said primer is not lost. Said primer may be directly linked to a solid phase, or may be linked indirectly to the solid phase by a hapten, antibody or the like which cannot be immobilized directly but can be immobilized via its specific binding partner (e.g., avidin or the like).

5. Strand Displacement Type DNA Polymerase

A strand displacement type DNA polymerase having DNA strand displacement activity can be used in the present invention. Additionally, it is particularly preferable that said strand displacement type DNA polymerase does not substantially have 5'→3' exonuclease activity.

The DNA polymerase to be used in the present invention is not particularly limited with as long as it has the stand displacement activity. Examples thereof include the following substances:

Klenow fragment of DNA polymerase I derived from *Escherichia coli*,

Phi29 DNA polymerase derived from bacteriophage φ29,

5'→3' exonuclease-deficient DNA polymerase derived from bacteriophage T7 (e.g., Sequenase or the like), 5'→3' exonuclease-deficient Bst DNA polymerase derived from *Bacillus stearothermophilus*, 5'→3' exonuclease-deficient Bca DNA polymerase derived from *Bacillus* caldotenax (e.g. BcaBEST DNA polymerase or the like), 5'→3' exonuclease-deficient DNA polymerase derived from *Pyrococcus* sp. GB-D (e.g., Deep VentR DNA polymerase, Deep VentR (exo-)DNA polymerase or the like), 5'→3' exonuclease-deficient DNA polymerase derived from *Pyrococcus furiosus* (e.g., Pfu DNA polymerase, Pfu Turbo DNA polymerase or the like), 5'→3' exonuclease-deficient DNA polymerase derived from *Thermus aquaticus* (e.g., Z-Taq DNA polymerase, Topo-Taq DNS polymerase or the like), 5'→3' exonuclease-deficient DNA polymerase derived from *Thermus thermophilus* (e.g., Δ Tth DNA polymerase or the like), 5'→3' exonuclease-deficient DNA polymerase derived from *Thermococcus* sp. 9° N-7 (e.g., 9° $N_m$ DNA polymerase, Therminator DNA polymerase or the like), 5'→3' exonuclease-deficient DNA polymerase derived from *Thermococcus litoralis* (e.g., Tli DNA polymerase, VentR DNA polymerase, VentR (exo-)DNA polymerase or the like), and 5→3' exonuclease-deficient DNA polymerase derived from *Thermococcus kodakaraensis* strain KOD 1 (e.g., KOD DNA polymerase, KOD Dash DNA polymerase, KOD-Plus-DNA polymerase or the like).

Regarding the DNA polymerase to be used in the present invention, any one of from mesophilic to heat-resistant ones can be suitably used. Additionally, the DNA polymerase to be used in the present invention may have an ability to carry out reverse transcription reaction.

The strand displacement type DNA polymerase to be used in the present invention may be either a substance obtained by purifying from a natural resource or a recombinant protein produced by means of a genetic engineering. Additionally, said enzyme may be those to which modifications such as substitution, deletion, addition, insertion and the like were applied by a genetic engineering or other methods.

Examples of particularly preferable examples of the strand displacement type DNA polymerase to be used in the present invention include a Klenow fragment of DNA polymerase I derived from *Escherichia coli*, which has been used for a long time, and a Phi29 DNA polymerase derived from bacteriophage φ29, a 5'→3' exonuclease-deficient Bst DNA polymerase derived from *Bacillus stearothermophilus*, a 5'→3' exonuclease-deficient Bca DNA polymerase derived from *Bacillus caldotenax* and the like, which are known to have particularly high strand displacement activity.

6. Template Nucleic Acid

The template nucleic acid in the nucleic acid amplification method of the present invention may be prepared or separated from any supply source having a possibility of containing said nucleic acid. As such a nucleic acid-containing supply source, for example, an environmental resource, food, agricultural product, fermented product, body fluid or tissue of the living body, cell or virus and the like can be cited. The body fluid or tissue of the living body includes, for example, blood, milk, cerebrospinal fluid, phlegm, saliva, feces, lung suction liquid, swab of a mucous membrane or tissue sample and the like. Also, it may be a nucleic acid-containing preparation obtained by treating these samples or the like with a conventionally known method. Also, the template nucleic acid may be a nucleic acid such as DNA, RNA or the like amplified by a conventionally known method from the aforementioned samples or the like or nucleic acid-containing preparation. Additionally, it may be a product completely or partially treated with a restriction enzyme or other nucleic acid-cleaving or degrading enzyme or the like.

Although is it not particularly limited as the template nucleic acid of the present invention, for example, a genomic DNA, a plasmid DNA, a double-stranded DNA such as an amplification product by PCR or other amplification method, a single-stranded DNA such as a cDNA prepared by the reverse transcription reaction from total RNA or messenger RNA, and the like can be suitably used as the template nucleic acid of the method of the present invention. Additionally, those in which a double-stranded DNA is denatured or unstabilized in such a manner that it becomes a single-stranded DNA completely or partially can also be used suitably.

When a nucleic acid having an RNA-derived sequence is amplified by the nucleic acid amplification method of the present invention, a cDNA prepared by the reverse transcription reaction using said RNA as the template can be suitably used as the template nucleic acid in the method of the present invention. Such a method for preparing cDNA by the reverse transcription reaction is conventionally known.

7. Deoxyribonucleotide 3-Phosphate

As the deoxyribonucleotide 3-phosphate (dNTP) to be used in the nucleic acid amplification method of the present invention, the substrate which is generally used in the general DNA synthesis reaction by a DNA polymerase, namely a mixture of dATP, dCTP, dGTP and dTTP, can be suitably used. Additionally, there is a case in which it may be a dNTP which does not contain at least one of dATP, dCTP, dGTP and dTTP.

Additionally, the dNTP to be used in the present invention may contain other dNTP or a derivative of the dNTP, as long as it can be used as the substrate of the DNA polymerase. Examples of the other dNTP or a derivative of the dNTP include dUTP, dITP, 7-deaza-dGTP, α-S-dNTP in which oxygen atom of the α-position phosphate group is replaced by sulfur atom, dNTP labeled with a radioisotope, a fluorescent material or the like, and the like.

8. Combination of Endonuclease V and DNA Polymerase

Regarding the combination of the endonuclease V and DNA polymerase to be used in the present invention, a suitable combination may be selected from the aforementioned preferable endonuclease V and the aforementioned preferable DNA polymerase. Namely, such a combination that the endonuclease V and DNA polymerase can suitably function the respective reactions in the reaction mixture of nucleic acid amplification reaction is preferable. Such a combination that the endonuclease V and DNA polymerase can suitably function the respective reactions under the same temperature condition is preferable. For example, a combination in which both of the endonuclease V and DNA polymerase are mesophilic enzymes and a combination in which both of the endonuclease V and DNA polymerase are heat-resistant enzymes are preferable.

Although examples of the preferable combination is not limited thereto, the examples include a combination in which the endonuclease V is an *Escherichia coli*-derived endonuclease V or the same to which modifications such as substitution, deletion, addition, insertion and the like are applied, and the DNA polymerase is Klenow fragment of an *Escherichia coli*-derived DNA polymerase I, a bacteriophage φ29-derived phi 29 DNA polymerase or either one of them to which modifications such as substitution, deletion, addition, insertion and the like are applied. Additionally, another examples of the preferable combination include a combination in which the endonuclease V is a *Thermotoga maritima*-derived endonuclease V or the same to which modifications such as substitution, deletion, addition, insertion and the like are applied, such as the *Thermotoga maritima*-derived mutation type endonuclease V disclosed in Japanese Patent Application 2005-308533, and the DNA polymerase is a 5'→3' exonuclease-deficient Bst DNA polymerase derived from *Bacillus stearothermophilus*, a 5'→3' exonuclease-deficient Bca DNA polymerase derived from *Bacillus caldotenax* or either one of them to which modifications such as substitution, deletion, addition, insertion and the like are applied.

Additionally, the endonuclease V and DNA polymerase to be used in the present invention may be provided as a form in which both enzymes are bound, as long as respective enzyme activity is not lost. For example, the endonuclease V and DNA polymerase may be provided as a fusion protein. Said fusion protein can be prepared as a recombinant protein by preparing a fusion gene from the genes encoding for respective enzyme, for example by a conventionally known genetic engineering means, and using said fusion gene.

9. Composition of Reaction Mixture

It is preferable that the reaction mixture in the nucleic acid amplification method of the present invention comprises a buffer agent which provides the enzyme activities with suitable conditions (e.g., pH, metal ion concentration, salt concentration and the like), a metal ion providing substance, salts and the like. Although the buffer agent is not particularly limited, examples thereof include conventionally known buffer agents generally used by those skilled in the art, such as Tris, Tricine, Bicine, HEPES, MOPS, TES, TAPS, PIPES, CAPS, a phosphate (sodium phosphate, potassium phosphate or the like) and the like.

As the aforementioned metal ion providing substance, it may be a conventionally known substance generally used by those skilled in the art and is not particularly limited. However, when the desired metal ion is for example $Mg^{2+}$, examples thereof include magnesium chloride, magnesium acetate, magnesium sulfate and the like. Additionally, the salts may also be conventionally known substances generally used by those skilled in the art and are not particularly limited. However, examples thereof include potassium chloride, potassium acetate, potassium sulfate, ammonium sulfate, ammonium chloride, ammonium acetate and the like. Also, as a matter of course, suitable selection and suitable concentration of these substances can be changed according to the kind and combination of the enzymes to be used. Additionally, the possibility of these substances to exert influence on the melting temperature of nucleic acid, the possibility of the dNTP to exert influence on the concentration of a free metal ion by chelating the metal ion, and the like are conventionally known, so that those skilled in the art can select an optimum reaction composition by taking these facts also into consideration.

Concentration of buffer agent in the aforementioned reaction mixture is preferably from 1 to 100 mM, more preferably from 5 to 50 mM. Also, pH of the buffer agent is preferably from 6.0 to 9.5, more preferably from 7.0 to 8.8. Concentration of magnesium chloride, magnesium acetate, magnesium sulfate or the like magnesium salt is preferably from 0.2 to 20 mM, more preferably from 2 to 12 mM. Also, concentration of potassium chloride, potassium acetate, potassium sulfate, ammonium sulfate, ammonium chloride, ammonium acetate or the like salt is preferably from 1 to 200 mM, more preferably from 2 to 125 mM.

For example, in case that the *Thermotoga maritima*-derived mutation type endonuclease V disclosed in Japanese Patent Application 2005-308533 is used as the endonuclease V, and a 5'→3' exonuclease-deficient Bst DNA polymerase derived from *Bacillus stearothermophilus* as the DNA polymerase, HEPES or the like can be used as a preferable example of the buffer agent. The concentration of said buffer agent is preferably from 5 to 30 mM and the pH is preferably from pH 7.0 to 8.8.

The concentration of each deoxyribonucleotide 3-phosphate (dNTP) in the aforementioned reaction mixture is preferably from 0.1 to 3.0 mM, more preferably from 0.2 to 1.2 mM.

The amount of each primer in the aforementioned reaction mixture is preferably from 10 to 1000 pmol, more preferably from 1 to 200 pmol, per 50 μl reaction mixture. In the case of the use of an outer primer, the amount of the outer primer is preferably from equivalent to 1/100 mol, preferably from 1/4 to 1/50 mol, based on the amount of the corresponding base X-containing primer.

Regarding the amount of enzymes in the aforementioned reaction mixture, the endonuclease V is preferably from 1 to 1000 pmol and the DNA polymerase is preferably from 0.2 to 32 U, per 50 μl reaction mixture. However, the amounts of enzymes can be optionally changed according to the kind, property and combination of the enzymes to be used. Also, it is well known to those skilled in the art that the definition of unit U (unit) which represents the enzyme activity sometimes varies depending on the kinds of enzymes and makers of the enzyme preparations. Additionally, optimum amounts of the enzymes for achieving proper amplification can also be changed according to the using conditions, amount of the primer, amount of the template nucleic acid, other reaction composition and the like.

Additionally, an additive agent may be allowed to coexist in the aforementioned reaction mixture. Although said additive agent is not particularly limited, examples thereof include 10% or less of dimethyl sulfoxide (DMSO), 3 M or less of betaine (N,N,N-trimethylglycine), 5% or less of formamide, 100 mM or less of tetramethylammonium chloride (TMAC), 1% or less of a surfactant (e.g., NP-40, Tween-20, Triton X-100 or the like), 10% or less of glycerol, 10% or less of a saccharide (dextran or the like), 10% or les of polyethylene glycol (PEG), 10 mM or less of dithiothreitol (DTT), 0.1% or less of bovine serum albumin (BSA), SSB protein (single-stranded DNA-binding protein) and the like.

Melting temperature of nucleic acid may be adjusted by adding a melting temperature adjusting agent to the aforementioned reaction mixture. Examples of said melting temperature adjusting agent include betaine, dimethylglycine, triethylamine N-oxide, DMSO and the like, and betaine is particularly preferable. The concentration of betaine in the reaction mixture is preferably within the range of no more than about 5.2 M which is its isostabilizing concentration, more preferably from 0.3 to 1.5 M.

A single-stranded nucleic acid-stabilizing agent may be used as said additive agent to be coexisted in the reaction mixture. Examples of the single-stranded nucleic acid-stabilizing agent include a single-stranded nucleic acid-binding protein. Examples of the single-stranded nucleic acid-binding protein include *Escherichia coli* SSB protein (single-stranded DNA-binding protein), *Escherichia coli* RecA protein, T4 phage gp32 or their corresponding proteins derived from other organisms or viruses, and the like can. The concentration of these single-stranded nucleic acid-binding proteins in the reaction mixture can be optionally selected by those skilled in the art. It is preferable to set the *Escherichia coli* SSB protein within the range of from 0.5 to 1.5 μg, and the *Escherichia coli* RecA protein and T4 phage gp32 within the range of from 0.5 to 3 μg, per 50 μl reaction mixture. Additionally, together with these single-stranded nucleic acid-binding proteins, their cofactors (e.g., ATP and its derivatives and the like) may be allowed to coexist, if necessary.

10. Incubation Step

In the nucleic acid amplification method of the present invention, the step for incubating the reaction mixture is not particularly limited, as long as it is under such conditions that it can carry out (i) specific annealing of the primer to the template nucleic acid, (ii) elongation chain synthesis reaction and strand displacement reaction by the DNA polymerase and (iii) recognition of a base X in a nucleic acid chain containing the base X and cleavage reaction of a phosphodiester bond positioned at downstream side (3' side) of the base X, by the endonuclease V. Although the temperature condition of said incubation step may be either alternating temperature or isothermal condition, isothermal condition is more preferable.

The "alternating temperature" according to the present invention means that the reaction temperature is changed for suitably carrying out respective reaction steps. For example, it means to change temperature suited for each of the aforementioned steps (i) to (iii). Also, the incubation step of alternating temperature may contain a temperature condition for modifying a double-stranded nucleic acid into a single-stranded counterpart. Additionally, the "isothermal condition" according to the present invention means that the incubation step is carried out at substantially a constant temperature without changing the temperature for carrying out respective reaction steps.

An advantage of the nucleic acid amplification method of the present invention is a point that raising and dropping of temperature namely temperature cycling is not necessary in the incubation step. Accordingly, an isothermal nucleic acid amplification method becomes possible according to the present invention. Said isothermal nucleic acid amplification method does not require the use of an expensive temperature cycling device, and keeping of the reaction mixture at a substantially constant temperature is enough. As said method for keeping of the reaction mixture at a substantially constant temperature, although it is not particularly limited, examples thereof include use of a device for controlling temperature (e.g., block incubator) and contact of a material body or substance of thermal insulation or exothermic state with the reaction mixture (e.g., a container charged with the reaction mixture is allowed to be present in a water bath, or a warm stone, a body heater or the like is allowed to contact with the reaction mixture or a container charged with the reaction mixture).

Regarding the temperature condition of the aforementioned isothermal nucleic acid amplification method, a temperature at which both of the endonuclease V and DNA polymerase can suitably carry out their activities is preferable, which is selected for example from a range of from about 20 to 80° C. For example, when both of the endonuclease V and DNA polymerase are mesophilic enzymes, from 20 to 40° C. is preferable. Additionally, when the endonuclease V is an *Escherichia coli*-derived endonuclease V or the same to which modifications such as substitution, deletion, addition, insertion and the like are applied, and the DNA polymerase is Klenow fragment of an *Escherichia coli*-derived DNA polymerase I, a bacteriophage φ29-derived phi 29 DNA polymerase or either one of them to which modifications such as substitution, deletion, addition, insertion and the like are applied, it is preferably from 30 to 40° C., and more preferably 30° C. or 37° C.

Also, when both of the endonuclease V and DNA polymerase are heat-resistant enzymes, the temperature condition of the aforementioned isothermal nucleic acid amplification method is preferably from 50 to 80° C. Additionally, for example, when the endonuclease V is a *Thermotoga maritima*-derived endonuclease V or the same to which to which modifications such as substitution, deletion, addition, insertion and the like are applied (e.g., the *Thermotoga maritima*-derived mutation type endonuclease V disclosed in Japanese Patent Application 2005-308533), and the DNA polymerase is a 5'→3' exonuclease-deficient Bst DNA polymerase derived from *Bacillus stearothermophilus*, a 5'→3' exonuclease-deficient Bca DNA polymerase derived from *Bacillus caldotenax* or either one of them to which modifications such as substitution, deletion, addition, insertion and the like are applied, it is preferably from 50 to 70° C., and more preferably from 55 to 65° C.

Additionally, the temperature condition of the aforementioned isothermal nucleic acid amplification method may be set to such a temperature that nonspecific annealing of the primer in the reaction mixture is reduced and also the primer is specifically annealed to the template nucleic acid sequence. Said temperature can be determined by referring to the melting temperature of the primer in the reaction mixture to be used and is selected for example from a range of from about 20 to 80° C. As a matter of course, by deciding the incubation temperature firstly, the primer designing may be carried out in such a manner that the reaction can be suitably carried out under said temperature, or kinds and concentrations of the melting temperature adjusting agent and other reaction constituents may be selected.

According to the nucleic acid amplification method of the present invention, the time for incubating the reaction mixture has no particular limitation as long as it is a time sufficient to achieve the desired amplification reaction. Suitable incubation time is for example within 4 hours, and more suitably from 20 minutes to 2 hours.

According to the nucleic acid amplification method of the present invention, the reaction during the incubation step is continued idealistically. However, in reality, the reaction is delayed or stopped in some cases due to factors such as concentration lowering or depletion of various components in the reaction mixture, lowering or deactivation of the enzyme activities and the like. When it is difficult to achieve the desired amplification reaction due to such a reason, the substances which are necessary for continuing the reaction may be supplied into the reaction mixture during the incubation step continuously or intermittently.

According to the nucleic acid amplification method of the present invention, even in the case of carrying out the amplification reaction under substantially isothermal condition, there is a case that firstly carrying out a thermal denaturation step (an incubation step by which a double-stranded nucleic acid is denatured or un-stabilized in such a manner that it becomes a single-stranded nucleic acid completely or partially) once is suitable for achieving further preferable amplification reaction. For example, when the template nucleic acid is a double-stranded DNA, there is a case that passing through said thermal denaturation step is suitable. As said thermal denaturation step, incubation is carried out for example at 95° C. for approximately from 1 to 10 minutes, although it is not limited thereto. Additionally, when the enzyme activities are completely or significantly lost through the denaturation step, it is preferable that, after carrying out the denaturation step, said enzymes are added to said reaction mixture adjusted to such a temperature that said enzyme activities are not lost, and subsequently incubated at a single temperature.

However, according to the nucleic acid amplification method of the present invention, the aforementioned thermal denaturation step is not always necessary even when the template nucleic acid is a double-stranded DNA. For example, when a melting temperature adjusting agent such as a betaine is contained in the reaction mixture at an appropriate concentration, there is a case in which an appropriate amplification reaction can be achieved by a step which does not contain the thermal denaturation step even when the template nucleic acid is a double-stranded DNA. Furthermore, according to the nucleic acid amplification method of the present invention, an appropriate amplification reaction can be achieved without using a melting temperature adjusting agent and by a step which does not contain the thermal denaturation step, even when the template nucleic acid is a double-stranded DNA. Thus, the use of a betaine or the like melting temperature adjusting agent and the presence or absence of carrying out a thermal denaturation step may be selected according to the necessity.

Additionally, according to the nucleic acid amplification method of the present invention, there is an effective case to further carry out an incubation step for suitably annealing the primer to the template nucleic acid, after the aforementioned thermal denaturation step and before the single temperature incubation for effecting accumulation of the amplification product. However, said annealing step is also not essential, or preferably unnecessary, so that those skilled in the art may select the presence or absence of carrying out said annealing step according to the necessity.

11. Detection Method of Target Nucleic Acid

The present invention further provides a method for detecting a target nucleic acid, which comprises a step for amplifying a target nucleic acid by the nucleic acid amplification method of the present invention (EVA) and a step for detecting whether or not an amplification product was formed by said step. The detection method of the present invention can be used in detecting the presence or absence of a target nucleic acid in various samples.

Although the use of the detection method of the present invention is not particularly limited, for example, when the target nucleic acid is a specific nucleic acid or a nucleic acid derived from an organism or virus belonging to a specific group, said organism or virus in a sample to be tested can be detected by the detection method of the present invention. When said organism is a pathogen, the pathogen in a sample to be tested can be detected. Additionally, the detection method of the present invention can also be used in the discrimination of genotype of an organism and expressing state of a gene, detection of a disease-related gene, drug reaction-related gene and the like, and the like.

According to the detection method of the present invention, an amplified nucleic acid can be detected by various methods, and it can be detected by various labels such as a staining which uses a nucleic acid binding agent (e.g., ethidium bromide, SYBR Green or the like) and by a radioactive material, a fluorescent material, a fluorescence quenching material, an enzyme and the like. Regarding the detection method of the present invention, the means for detecting whether or not an amplification product was formed is not particularly limited. For example, conventional methods such as an electrophoresis, a hybridization assay, a combination thereof and the like can be used. Additionally, various methods which are conventionally known to those skilled in the art, which are used for detecting products of PCR and other nucleic acid amplification methods, can also be used suitably for the detection of a product by the detection method of the present invention.

For example, by using a nucleic acid having a sequence substantially complementary with an amplification product as the probe, a signal based on the hybridization of said probe to the amplification product or a change in the signal may be detected. Said probe may be immobilized on a solid phase or not. For example, it may be detected using a nucleic acid probe labeled with a fluorescent material, by a method for detecting an amplification product based on a change in the dissolution degree of its fluorescence polarization, namely a fluorescence polarization [e.g., "*High Function Biosensor for Food Industry*" edited by High Function Biosensor Work Sectional Meeting, Society for Techno-innovation of Agriculture, Forestry and Fisheries, published by Kagaku Kogyo Nippo, 2003, p. 73-82 and 261-292, Tsuruoka M., Karube I: Rapid hybridization at high salt concentration and detection of bacterial DNA using fluorescence polarization. Comb Chem High Throughput Screen, 6, p. 225-34 (2003)]. Also, for example, hybridization of the probe may be carried out by the detection by surface plasmon resonance [e.g., Kai E, Sawata S, Ikebukuro K, Tida T, Honada T, Karube I: Detection of PCR products in solution using surface plasmon resonance. *Anal Chem,* 71, p. 796-800 (1999)], detection by quartz crystal microbalance [e.g., Takahisa Miyamoto: Quick *Salmonella* detection method by PCR and DNA-immobilized quartz oscillator, *Japanese Journal of Food Microbiology,* 17, 2000, p. 217-224] and the like.

Also, according to the detection method of the present invention, whether or not an amplification product was formed may be detected by detecting a substance which is secondarily formed accompanied by the amplification of nucleic acid. For example, pyrophosphoric acid or a salt thereof, such as magnesium pyrophosphate, released from dNTP accompanied by the synthesis of a nucleic acid chain may be detected by the measurement of turbidity or observation of the precipitate, or by an enzymatic method [e.g., Misako Endo, Noriyuki Saito, Noboru Maruyama: Development of easy and quick detection method of food pathogenic microorganisms, $2002^{nd}$ Research Report, Miyagi Prefectural General Industrial Technology Center, 1, 2002, 10-14].

According to the detection method of the present invention, the step for detecting whether or not an amplification product was formed may be carried out after the amplification step of the nucleic acid amplification method of the present invention, or may be carried out during the operation of said amplification step. For example, amplification of the target nucleic acid may be monitored real time. In a preferable embodiment of such a case, a nucleic acid detecting agent is allowed to be present in the reaction mixture in advance, and the amplification product is detected based on the change in a signal derived from the detecting agent. Examples of said nucleic acid detecting agent include a nucleic acid binding agent (ethidium bromide, SYBR Green or the like), a labeled nucleic acid probe (e.g., a fluorescence-labeled probe, a fluorescence energy transfer probe or the like) and the like. Additionally, the nucleic acid detecting agent may be dNTP, and in that case, a signal based on the pyrophosphoric acid or a salt thereof, such as magnesium pyrophosphate, released from dNTP accompanied by the synthesis of a nucleic acid chain can be detected for example by the measurement of turbidity.

12. Kit

An embodiment of the present invention is a reagent kit to be used in the nucleic acid amplification method of the present invention, namely a nucleic acid amplification reagent kit. It is preferable that said kit comprises a medium which records instructions instructing the use of the endonuclease V and the DNA polymerase having strand displacement activity. It is more preferable that said kit comprises at least the endonuclease V, or at least the endonuclease V and the DNA polymerase having strand displacement activity.

Additionally, another embodiment of the present invention is a reagent kit to be used in the nucleic acid sequence detection method of the present invention, namely a nucleic acid detection reagent kit. It is preferable that said kit comprises a medium which records instructions instructing the use of the endonuclease V and the DNA polymerase having strand displacement activity. It is more preferable that said kit comprises at least the endonuclease V, or at least the endonuclease V and the DNA polymerase having strand displacement activity.

In order to facilitate operation of the method of the present invention by the users, the nucleic acid amplification reagent kit and nucleic acid detection reagent kit of the present invention may use, in addition to the enzymes to be used, a reaction liquid which is prepared in advance for the enzymes to be used, or a buffer liquid, a substrate or a substrate solution, primers, a supply source of metal ions such as magnesium ion and the like and the like as the materials for preparing said reaction liquid, as composing elements according to the necessity. Also if necessary, a nucleic acid detecting agent may be used as a composing element. Said composing elements can be provided as a solution having such a concentration that the method of the present invention can be suitably carried out or a certain times of said concentration (e.g., 10 times concentration of said concentration). Also, said composing elements may be contained in a single container in respective amounts for use in one or two or more times of the reaction. Additionally, a medium recording the procedure for carrying out the method of the present invention, examples thereof, and the like may also be used as a composing element of the present invention according to the necessity.

EXAMPLES

The following describes the present invention further in detail with reference to examples. In this connection, the present invention is not limited to the examples described in the following.

Example 1

Preparation of Wild Type and Mutation Type Endonuclease V (1) Preparation of Wild Type Endonuclease V Gene A wild type endonuclease V gene was prepared by the following procedure. Firstly, a *Thermotoga maritima* strain ATCC 43589 was purchased from a systematic microorganisms preservation facility (Japan Collection of Microorganisms, JCM), RIKEN, (JCM No. 10099). Into 100 ml of a predetermined medium, 1 ml of said strain liquid was inoculated and statistically cultured at 80° C. for 48 hours under anaerobic condition. After carrying out centrifugation of 20 ml of the culture broth at 13000×g for 5 minutes, the precipitated cells were suspended in 1 ml of ultrapure water. The suspension was subjected to an ultrasonic disintegration treatment and then centrifuged at 13000×g for 5 minutes to recover the supernatant to obtain a disintegration supernatant containing *Thermotoga maritima* chromosomal DNA.

Next, a *Thermotoga maritima* endonuclease V gene (GenBank Accession AAD 36927) was amplified by a PCR shown in the following procedure. As the template, 1 µl of the *Thermotoga maritima* disintegration supernatant was used and added to a reaction liquid (50 µl in total volume). As the DNA polymerase, 1.0 U of KOD plus (mfd. by TOYOBO Co., Ltd.) was added to the reaction liquid. As the buffer, 5 µl of the 10 times concentration buffer (10×KOD-PCR buffer) attached to the KOD plus product was added. As the primers, the oligonucleotides represented by SEQ ID NOs:3 and 4 were added to the reaction liquid to a final concentration of 0.3 µM, respectively. A dNTP mixture was added to be final concentration of 0.2 mM, and MgSO$_4$ was added to be final concentration of 1 mM, to the reaction liquid respectively.

GeneAmp PCR System 9600 (mfd. by Perkin Elmer Co., Ltd.) was used as the thermal cycler and, after heating once at 94° C. for 2 minutes, a temperature cycle of 15 seconds at 94° C., 30 seconds at 57° C. and 1 minute at 68° C. was repeated 35 times. The amplification product was purified using QIAquick PCR Purification Kit (mfd. by QIAGEN) and eluted with 50 µl of ultrapure water. Procedure of the purification operation was carried out in accordance with the instructions attached to said kit.

In accordance with the usual manner, the thus obtained amplification product was inserted into an *Escherichia coli* recombinant protein expression vector pET16b having a His-tag sequence (mfd. by Novogen). Nucleotide sequence of the endonuclease V gene of the thus obtained recombinant DNA (to be referred to as pET16 TmaEV hereinafter) was deciphered by a DNA sequencer. The thus deciphered sequence coincided with the already known nucleotide sequence of *Thermotoga maritima* endonuclease V gene (GenBank Accession AE 001823).

(2) Preparation of Mutation Type Endonuclease V Gene

Double site-specific mutations were introduced into the amino acid sequence of wild type endonuclease V by the following procedure. Firstly, as the first mutagenesis, an endonuclease V gene in which a nucleotide sequence encoding for the tyrosine positioned at the 80-position of the amino acid sequence of wild type endonuclease V was replaced by a nucleotide sequence encoding for alanine (Y80A mutation) was prepared. Site-specific mutation was introduced into the object nucleotide sequence of using QuickchangeII Site Directed Mutagenesis Kit (mfd. by Stratagene). As the template, 50 ng of pET16 TmaEV was used, and the oligonucleotides shown by SEQ ID NOs:5 and 6 were used as the primers for Y80A mutagenesis use. Total volume of the reaction liquid was adjusted to 51 µl. The reaction liquid composition and operation procedure were effected in accordance with the instructions attached to the kit. In the manner, a recombinant DNA containing a mutation type endonuclease V gene introduced with the Y80A mutation (to be referred to as pET16 TmaEVM1 hereinafter) was obtained.

Next, as the second mutagenesis, a nucleotide sequence encoding for the aspartic acid positioned at the 105-position of the amino acid sequence of the endonuclease V (Y80A) encoded by pET16 TmaEVM1 was replaced by a nucleotide sequence encoding for alanine (D105A mutation) in the same manner as in the above-mentioned method. The pET16 TmaEVM1 was used as the template, and the oligonucleotides shown by SEQ ID NOs: 7 and 8 were used as the primers for D105A mutagenesis use. In the manner, a recombinant DNA containing a mutation type endonuclease V gene introduced with double amino acid mutagenesis of Y80A and D105A (to be referred to as pET16 TmaEVM2 hereinafter) was obtained. By deciphering nucleotide sequence of the endonuclease V gene of pET16 TmaEVM2 by a DNA sequencer, it was confirmed that substitution of the object base is present. Additionally, the nucleotide sequence other than the mutation-introduced parts coincided with the already known nucleotide sequence of *Thermotoga maritima* endonuclease V gene (GenBank Accession AE 001823). In the above manner, a mutation type endonuclease V gene was obtained.

(3) Expression and Purification of Wild Type and Mutation Type Endonuclease V

By making use of an *Escherichia coli* recombinant protein expression system, the wild type endonuclease V and mutation type endonuclease V were expressed by the following procedure. Using pET16 TmaEV having wild type *Thermotoga maritima* endonuclease V gene or pET16 TmaEVM2 having mutation type *Thermotoga maritima* endonuclease V gene, a host *Escherichia coli* strain BL21(DE3) (mfd. by Novogen) was transformed by the usual way. The thus obtained transformant was inoculated into 8 ml of an LB medium (peptone 10 g/l, yeast extract 5 g/l, NaCl 10 g/l) containing ampicillin (50 µg/m1 in final concentration), and shaking culture was carried out at 37° C. until OD 600 of the medium reached 0.6. Subsequently, the culture broth was inoculated into 800 ml of the LB medium containing ampicillin (50 µg/ml in final concentration), and shaking culture was carried out at 37° C. until OD 600 of the medium reached 0.6. Thereafter, expression of the object protein was induced by adding isopropyl-β-thiogalacto-pyranoside (1 mM in final concentration), and shaking culture was carried out at 30° C. for 5 hours. The culture broth was centrifuged at 13000×g for 10 minutes. The thus precipitated cells were suspended in 30 ml of a buffer [20 mM HEPES (pH 7.4), 1 mM EDTA, 0.1 mM DTT, 50 mM NaCl] containing a protease inhibitor cocktail (mfd. by Sigma). To an ultrasonic disintegration treatment, 30 ml of the suspension was subjected and then centrifuged at 13000×g for 10 minutes to recover the supernatant. By heat-treating the thus obtained supernatant at 75° C. for 15 minutes, the protein derived from the host *Escherichia coli* contained in the supernatant was denatured.

Thereafter, the heat-treated liquid was centrifuged at 13000×g for 10 minutes, and the supernatant was recovered.

The thus obtained supernatant was filtered through a 0.2 μm pore size filter, and then the wild type endonuclease V or mutation type endonuclease V was purified using a His-tag fusion protein purification column, HisTrap HP (mfd. by Amersham Bioscience). In this case, a stepwise elution was carried out using vacuum-deaerated buffer A [50 mM HEPES (pH 7.4), 1 mM EDTA, 0.1 mM DTT, 50 mM NaCl, 20 mM imidazole] and buffer 13 [50mM HEPES (pH 7.4), 1 mM EDTA 0.1 mM DTT, 50 znM NaCl, 500 mM imidazole] as the buffers. By carrying out SDSPAGE on the thus obtained elution fractions, a single protein band was observed for the expected molecular weight, so that it was confirmed that the wild type endonuclease V or mutation type endonuclease V was purified.

The double mutation (Y80A and D105A) *Thermotoga maritima* endonuclease V prepared in the above manner (to be referred to as mutation type Tma endonuclease V hereinafter) was used in the Examples shown in the following.

Example 2

Amplification Using Linear DNA Fragment as the Template (1) Preparation of Template DNA A DNA fragment to be used as the template of EVA was prepared by PCR. As the template for PCR use, 20 ng of a plasmid pUC18 (GenBank Accession No. L09136) was used, and 20 pmol of the oligonucleotides shown by SEQ ID NOs: 9 and 10 were used as the primers. These primers were designed in such a manner that a DNA fragment of 243 bp containing the multi-cloning site of pUC18 is amplified, and each of them contains one deoxyinosine. As the DNA polymerase, 2.5 U of TaKaRa Taq (mfd. by Takara Bio) was used, and those attached to the same product were used as the reaction buffer and dNTP mixture.

PCR was carried out by preparing 100 μl in total volume of a PCR reaction liquid. GeneAmp PCR System 9600 (mfd. by Perkin Elmer Co., Ltd.) was used as the thermal cycler and, after heating once at 94° C. for 1 minute, a temperature cycle of 30 seconds at 94° C., 30 second at 63° C. and 30 seconds at 72° C. was repeated for 35 times. After completion of the reaction, the thus obtained amplification product was purified using QIAquick PCR Purification Kit (mfd. by QIAGEN) and eluted with 50 μl of ultrapure water. The purification operation was carried out in accordance with the instructions attached to said purification kit. The purified sample was subjected to a 1.5% agarose gel electrophoresis and the gel was stained with ethidium bromide, and then the presence of a DNA fragment having a length of about 240 bp was confirmed under UV irradiation.

(2) Amplification Reaction by EVA

A nucleic acid amplification by the EVA method was carried out using the DNA fragment prepared by the method described in Example 2(1) as the template. The oligonucleotide shown by SEQ ID NOs: 9 and 10 were used as the primers. These respectively contain one deoxyinosine. The *Thermotoga maritima* endonuclease V containing the double mutation (Y80A and D105A mutations) which was prepared in Example 1 (to be referred to as mutation type Tma endonuclease V hereinafter) was used as the endonuclease V.

EVA reaction liquid [final composition: 10 mM HEPES buffer (pH 7.4), 5 mM magnesium chloride, 1 mM dithiothreitol, 0.4 mM of each of dNTP (dATP, dCTP, dGTP and dTTP), 2 pmol, 200 fmol or 20 fmol of each primer, 10 fmol of template DNA, 8 U of Bst DNA polymerase (mfd. by New England Biolabs), 19 pmol of mutation type Tma endonuclease V, ultrapure water] was prepared to be a total volume of 25 μl. Additionally, similar reaction liquid which does not contain the template DNA was also prepared as a control.

The above-mentioned EVA reaction liquid thus prepared was allowed to undergo the reaction by incubating at 65° C. for 2 hours. After completion of the reaction, 5 μl of the reaction liquid was fractioned and subjected to 1.5% agarose gel electrophoresis. After staining with ethidium bromide, the presence or absence of the amplification product and its color density were confirmed under UV irradiation. The results are shown in FIG. 7.

Figure 7:
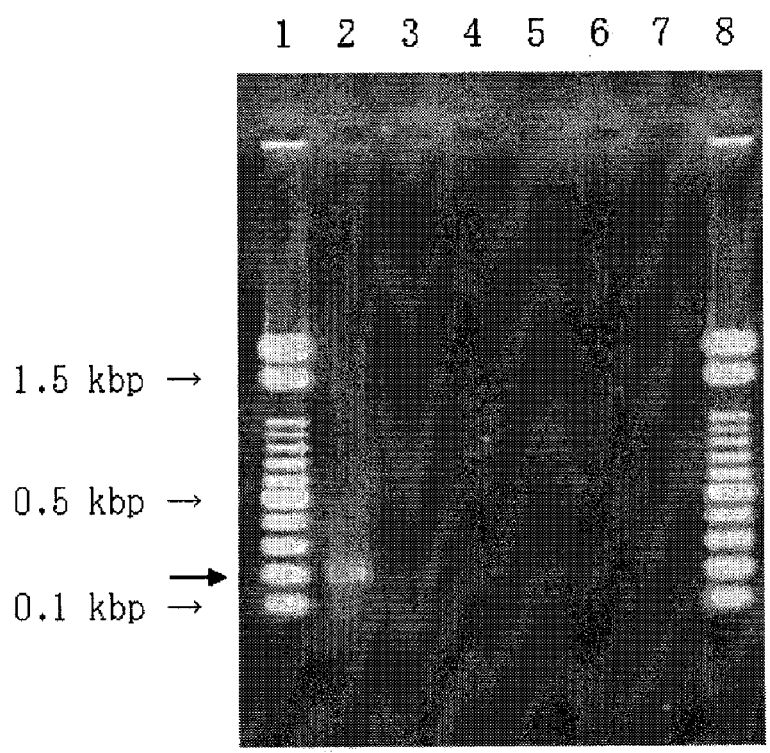
FIG. 7 is a figure showing an agarose electrophoresis image of an amplification product obtained by the nucleic acid amplification method of the present invention using a linear DNA fragment as the template.

In FIG. 7, the lane 1 and lane 8 are molecular weight size marker 100 bp DNA Ladder (mfd. by TOYOBO), and the lanes 2, 3 and 4 are results of using the EVA reaction liquid which used 2 pmol, 200 fmol and 20 fmol of respective primers. Also, the lanes 5, 6 and 7 are results of using the template DNA-free EVA reaction liquid which used 2 pmol, 200 fmol and 20 fmol of respective primers. In the lanes 2 and 3 of FIG. 7, a single band was detected at around the position expected to be the size of the amplification product so that amplification of the object DNA fragment was confirmed. On the other hand, the amplification product was not detected from the lanes 5 to 7 (reaction which does not contain the template DNA).

(3) Restriction Enzyme Digestion of Amplification Product

Digestion with restriction enzymes was carried out in order to verify whether or not the amplification product obtained in Example 2(2) is a DNA fragment having the object nucleic acid sequence. Using 20 μl of the aforementioned EVA reaction liquid which used 2 pmol of primers (FIG. 7, lane 2), the amplification product was purified using QIAquick PCR Purification Kit (mfd. by QIAGEN) and eluted with 35 μl of ultrapure water. The purification operation was carried out in accordance with the instructions attached to said kit.

Figure 8:
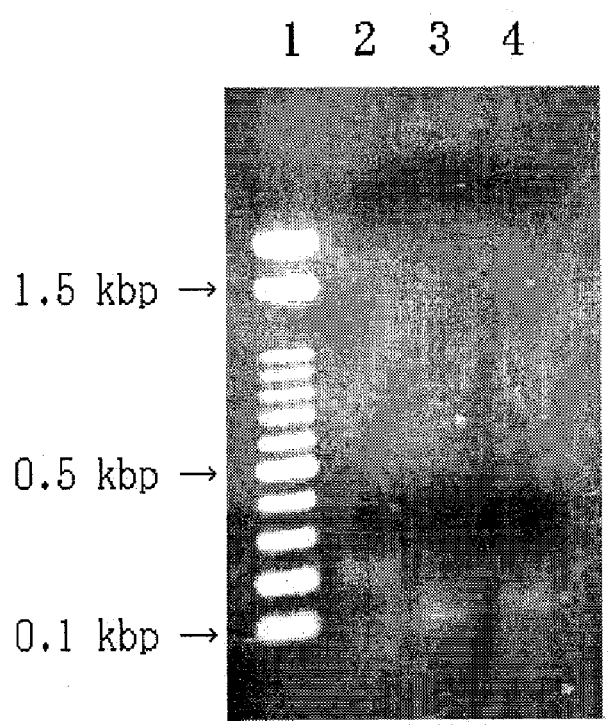
FIG. 8 is a figure showing an agarose electrophoresis image of product restriction enzyme digests of an amplification product obtained by the nucleic acid amplification method of the present invention.

Using 8 μl of the purified amplification product, restriction enzyme treatment with 10 U of restriction enzyme BamHI or 10 U of HindIII (mfd. by Nippon Gene Co., Ltd.) was carried out. The buffer solution attached to the enzyme products was used as the reaction buffer. After preparing 20 μl of a reaction liquid, it was incubated at 37° C. for 1 hour. After completion of the reaction, 10 μl of the sample was fractioned and subjected to 1.5% agarose gel electrophoresis. FIG. 8 shows the result of the size of the DNA fragment was observed under UV irradiation after staining with ethidium bromide.

In FIG. 8, the lane 1 is molecular weight size marker 100 bp DNA Ladder (mfd. by TOYOBO Co., Ltd.); the lane 2 is the amplification product which was not treated with the restriction enzyme; the lane 3 is the BamHI digest; and the lane 4 is the HindIII digest. When the amplification product is formed by the specific amplification, the BamHI and HindIII recognition sites are present each at one position in its nucleotide sequence, and two DNA fragments are formed when the amplification product was digested with each enzyme. The length of the expected digestion fragment was 109 bp and 134 bp in the case of the BamHI digestion, and 79 bp and 164 bp in the case of the HindIII digestion. As shown in the lanes 3 and 4, the band of original amplification product disappeared as a result of the digestion of the amplification product with BamHI or HindIII, and bands were detected at around the expected molecular weights of the digest. Based on this, it was found that the amplification product of EVA obtained in Example 2(2) is the specific amplification product having the object nucleic acid sequence.

Example 3

Amplification Using Cyclic Plasmid DNA as the Template (1)

Using the cyclic plasmid pUC18 as the template, the nucleic acid was amplified by the EVA method. The oligonucleotides shown by SEQ ID NOs: 9 and 10 were used as the primers. The expected amplification range when these primers are used was a region of about 240 bp containing the multi-cloning site of pUC18.

EVA reaction liquid [final composition: 10 mM HEPES buffer (pH 7.4), 5 mM magnesium chloride, 1 mM dithiothreitol, 100 mM potassium acetate, 0.4 mM of each of dNTP (dATP, dCTP, dGTP and dTTP), 4 pmol of each primer, 2 fmol or 20 fmol of pUC18, 16 U of Bst DNA polymerase (mfd. by New England Biolabs), 38 pmol of mutation type Tma endonuclease V, ultrapure water] was prepared to be a total volume of 50 µl.

The above-mentioned EVA reaction liquid was allowed to undergo the reaction by incubating at 65° C. for 2 hours. After completion of the reaction, 5 µl of the reaction liquid was fractioned and subjected to 1.5% agarose gel electrophoresis. After staining with ethidium bromide, the presence or absence of the amplification product and its color density were verified under UV irradiation. The results were shown in FIG. 9.

Figure 9:
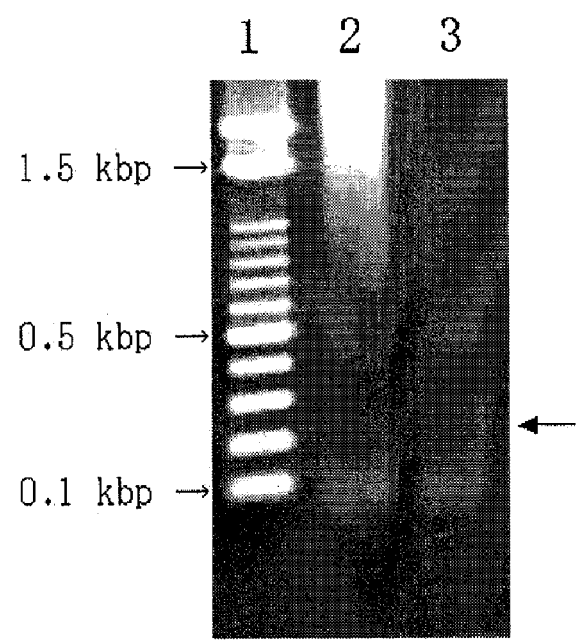
FIG. 9 is a figure showing an agarose electrophoresis image of an amplification product obtained by the nucleic acid amplification method of the present invention using a cyclic plasmid DNA as the template.

In FIG. 9, the lane 1 is molecular weight size marker 100 bp DNA Ladder (mfd. by TOYOBO), and the lanes 2 and 3 are results when the EVA was carried out respectively using 2 fmol and 20 fmol of pUC18 as the template. As shown in the lane 3, the presence of the amplification product having the expected size was detected.

Example 4

Amplification Using Cyclic Plasmid DNA as the Template (2)

Using the cyclic plasmid pUC18 as the template and using the oligonucleotides shown by SEQ ID NOs:11 and 12 as the primers, nucleic acid amplification by the EVA method was carried out. The expected amplification range when these primers are used was a region of about 240 bp containing the multi-cloning site of pUC18.

EVA reaction liquid [final composition: 10 mM HEPES buffer (pH 7.4), 5 mM magnesium chloride, 1 mM dithiothreitol, 100 mM potassium acetate, 0.4 mM of each of dNTP, 4 pmol of each primer, 2 fmol or 20 fmol of pUC18, 16 U of Bst DNA polymerase (mfd. by New England Biolabs), 38 pmol of mutation type Tma endonuclease V, ultrapure water] was prepared to be a total volume of 50 µl.

The above-mentioned EVA reaction liquid was allowed to undergo the reaction by incubating at 65° C. for 90 minutes. After completion of the reaction, 5 µl of the reaction liquid was used as an analyte and subjected to 1.5% agarose gel electrophoresis. After staining the gel with ethidium bromide, the presence or absence of the amplification product was verified under UV irradiation. The results were shown in FIG. 10.

Figure 10:
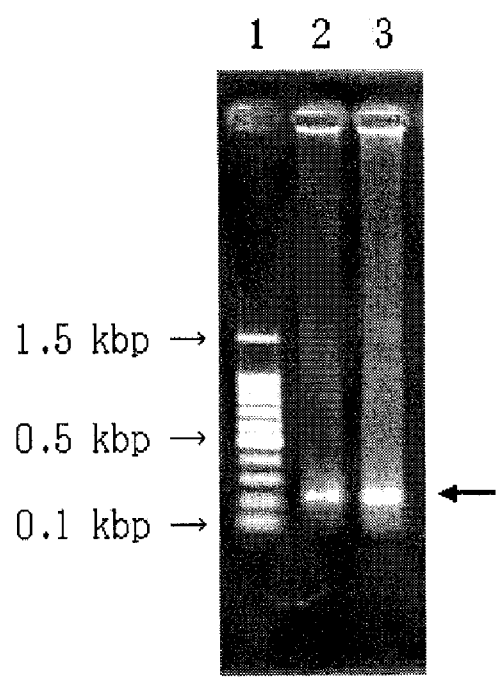
FIG. 10 is a figure showing an agarose electrophoresis image of an amplification product obtained by the nucleic acid amplification method of the present invention using a cyclic plasmid DNA as the template.

In FIG. 10, the lane 1 is molecular weight size marker 100 bp DNA Ladder (mfd. by TOYOBO), and the lanes 2 and 3 are results when the EVA was carried out respectively using 2 fmol and 20 fmol of pUC18 as the template. As shown in FIG. 10, the presence of the amplification product having the expected size was detected in the lanes 2 and 3.

Example 5

Amplification Using Cyclic Plasmid DNA as the Template (3)

Using the cyclic plasmid pUC18 as the template and the oligonucleotides shown by SEQ ID NOs:13 and 14 as the primers, the nucleic acid was amplified by the EVA method. The expected amplification range when these primers are used was a region of about 630 bp.

EVA reaction liquid [final composition: 10 mM HEPES buffer (pH 7.4), 5 mM magnesium chloride, 1 mM dithiothreitol, 100 mM potassium acetate, 0.4 mM of each of dNTP, 4 pmol of each primer, 2 fmol or 20 fmol of pUC18, 16 U of Bst DNA polymerase (mfd. by New England Biolabs), 38 pmol of mutation type Tma endonuclease V, ultrapure water] was prepared to be a total volume of 50 µl.

The above-mentioned EVA reaction liquid was allowed to undergo the reaction by incubating at 65° C. for 90 minutes. After completion of the reaction, 5 µl of the reaction liquid was used as an analyte and subjected to 1.5% agarose gel electrophoresis. After staining with ethidium bromide, the presence or absence of the amplification product was verified under UV irradiation. The results were shown in FIG. 11.

Figure 11:
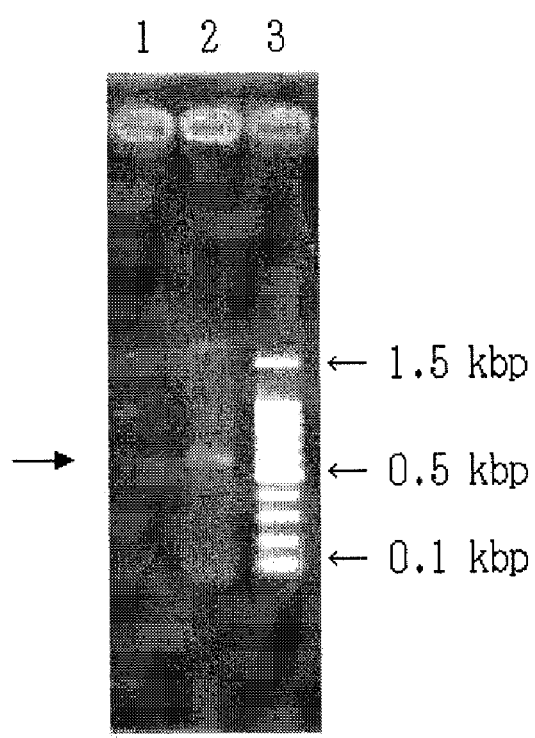
FIG. 11 is a figure showing an agarose electrophoresis image of an amplification product obtained by the nucleic acid amplification method of the present invention using a cyclic plasmid DNA as the template.

In FIG. 11, the lanes 1 and 2 are results when the EVA was carried out respectively using 2 fmol and 20 fmol of pUC18 as the template. The lane 3 is molecular weight size marker 100 bp DNA Ladder (mfd. by TOYOBO Co., Ltd.). As shown in the lanes 1 and 2, a band of DNA fragment was detected at a position of around 630 bp which is the size of expected amplification product.

Example 6

EVA Including Thermal Denaturation Step of Template

Using the cyclic plasmid pUC18 as the template and the oligonucleotides shown by SEQ ID NOs:13 and 14 as the primers, the nucleic acid was amplified by the EVA method. The expected amplification range when these primers are used was a region of about 630 bp.

A reaction liquid was prepared by the following procedure. Firstly, a reaction liquid containing all of the components excluding the two kinds of enzymes (Bst DNA polymerase and mutation type Tma endonuclease V) was prepared to be a total volume of 46 µl. Next, for the thermal denaturation of template, the reaction liquid was kept at 95° C. for 5 minutes and then cooled on ice. Subsequently, the Bst DNA polymerase and mutation type Tma endonuclease V were added to the reaction liquid and mixed. EVA reaction liquid [final composition: 10 mM HEPES buffer (pH 7.4), 5 mM magnesium chloride, 1 mM dithiothreitol, 100 mM potassium acetate, 0.4 mM of each of dNTP (dATP, dCTP, dGTP and dTTP), 4 pmol of each primer, 20 fmol of pUC18, 16 U of Bst DNA polymerase (mfd. by New England Biolabs), 3.8 pmol of mutation type Tma endonuclease V, ultrapure water] was finally prepared to be be a total volume of 50 µl.

The above-mentioned EVA reaction liquid was allowed to undergo the reaction by incubating at 65° C. for 1 hour. After completion of the reaction, 5 µl of the reaction liquid was used as an analyte and subjected to 1.5% agarose gel electrophoresis, and after staining with ethidium bromide, the presence or absence of the amplification product and its color density were verified under UV irradiation, with the results shown in FIG. 12.

Figure 12:
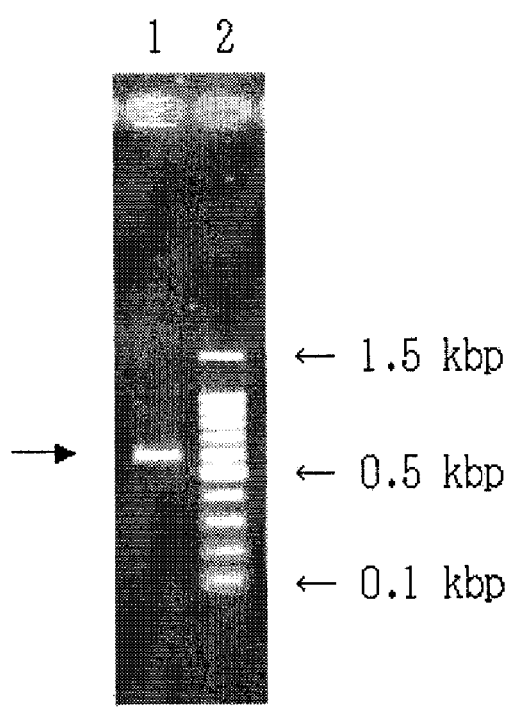
FIG. 12 is a figure showing an agarose gel electrophoresis of an amplification product obtained by the nucleic acid amplification method of the present invention which includes a thermal denaturation step of the template.

In FIG. 12, the lanes 1 is the amplification product by the above-mentioned method, and the lane 2 is molecular weight size marker 100 bp DNA Ladder (mfd. by TOYOBO). In the lane 1, a band was detected at a position of around 630 bp which is the size of expected amplification product.

Example 7

Restriction Enzyme Digestion of Plasmid Amplification Product

Using the cyclic plasmid pUC18 as the template, and the oligonucleotides shown by SEQ ID NOs:11 and 12 as the primers, the nucleic acid was amplified by the EVA method. The expected amplification range when these primers are used was a region of about 240 bp including the multi-cloning site of pUC18.

A reaction liquid was prepared by the following procedure. Firstly, a reaction liquid containing all of the components excluding the two kinds of enzymes (Bst DNA polymerase and mutation type Tma endonuclease V) was prepared to be a total volume of 92 μl. Next, this reaction liquid was kept at 95° C. for 5 minutes and then quickly cooled on ice. Subsequently, the Bst DNA polymerase and mutation type Tma endonuclease V were added to the reaction liquid and mixed, and 100 μl in total volume of EVA reaction liquid [final composition: 10 mM HEPES buffer (pH 7.4), 4 mM magnesium chloride, 1 mM dithiothreitol, 100 mM potassium acetate, 0.4 mM of each of dNTP (dATP, dCTP, dGTP and dTTP), 0.5 mM betaine, 32 pmol of each primer, 4 fmol of pUC18, 32 U of Bst DNA polymerase (mfd. by New England Biolabs), 7.6 pmol of mutation type Tma endonuclease V, ultrapure water] was finally prepared.

The above-mentioned EVA reaction liquid was allowed to undergo the reaction by incubating at 65° C. for 75 minutes. After completion of the reaction, 5 μl of the reaction liquid was fractioned and subjected to a 2.0% agarose gel electrophoresis. After staining with ethidium bromide, it was confirmed under UV irradiation that the amplification product of about 240 bp was obtained.

By digesting the amplification product obtained by the above-mentioned reaction with restriction enzymes, whether or not it is a DNA fragment having the object nucleic acid sequence was verified. By taking out 90 μl of the reaction liquid after amplification reaction, the amplification product was purified using QIAquick PCR Purification Kit (mfd. by QIAGEN) and eluted with 50 μl of ultrapure water. The purification operation was carried out in accordance with the instructions attached to said purification kit. Digestion of 10 μl of the thus obtained eluate with 20 U of a restriction enzyme BamHI, 20 U of HindIII or 15 U of XhoI, was carried out respectively. The buffer attached to each enzyme product was used and the reaction liquid was adjusted to be a total volume of 20 μl with ultrapure water, followed by digestion with the restriction enzymes through 2 hours of incubation at 37° C. Thereafter, by subjecting to a 2.0% agarose gel electrophoresis and then staining the gel with ethidium bromide, the presence or absence of the amplification product was verified under UV irradiation. The results were shown in FIG. 13.

Figure 13:
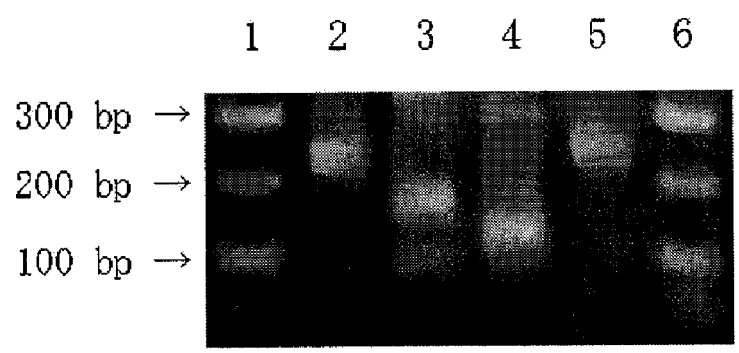
FIG. 13 is a figure showing an agarose gel electrophoresis image of restriction enzyme digests of an amplification product by the nucleic acid amplification method of the present invention.

In FIG. 13, the lanes 1 and 6 are molecular weight size marker 100 bp DNA Ladder (mfd. by TOYOBO Co., Ltd.); the lane 2 is the amplification product which was not treated with the restriction enzymes; the lane 3 is the BamHI digest; the lane 4 is the HindIII digest; and the lane 5 is the XhoI digest. It was considered that when the amplification product was formed by the specific amplification, the BamHI and HindIII recognition sites are present each at one position in its nucleotide sequence, and two DNA fragments are formed when digested with each enzyme. The lengths of the fragments were 79 bp and 164 bp when digested with HindIII, and the lengths of the fragments were 109 bp and 134 bp when digested with BamHI. On the other hand, since the XhoI recognition site is not present in the nucleic acid sequence in the amplification region, it was considered that the amplification product is not digested by said enzyme. As shown in the lanes 3 and 4, the band of original amplification product disappeared as a result of the digestion of the amplification product with BamHI or HindIII, and bands were detected at around the expected molecular weights of the digest. It was confirmed by the lane 5 that the amplification product was not digested when it was treated with XhoI. Based on this, it was found that the specific object amplification product was obtained by the EVA method.

Example 8

Control Test for Showing Components which is Necessary for the Reaction of the Nucleic Acid Amplification Method of the Present Invention Reaction liquid 1 for EVA was prepared by the following procedure. Firstly, reaction liquid containing all of the components excluding the two kinds of enzymes (Bst DNA polymerase and mutation type Tma endonuclease V) was prepared to be a total volume of 46 μl. Next, the reaction liquid was kept at 95° C. for 5 minutes and then cooled on ice. Subsequently, the Bst DNA polymerase and mutation type Tma endonuclease V were added to the reaction liquid and mixed, and 50 μl in total volume of EVA reaction liquid [final composition: 10 mM HEPES buffer (pH 7.4), 4 mM magnesium chloride, 1 mM dithiothreitol, 100 mM potassium acetate, 0.4 mM of each of dNTP (dATP, dCTP, dGTP and dTTP), 0.5 mM betaine, 16 pmol of the primer of SEQ ID NO:11, 16 pmol of the primer of SEQ ID NO:12, 2 fmol of pUC18, 16 U of Bst DNA polymerase (mfd. by New England Biolabs), 3.8 pmol of mutation type Tma endonuclease V, ultrapure water] was finally prepared.

Additionally, although similar to the above-mentioned EVA reaction liquid 1, reaction liquids 2 to 6 which do not contain one of the DNA polymerase, endonuclease V, primer set, dNTP and template DNA were respectively prepared. The thus prepared these EVA reaction liquids were allowed to undergo the reaction by incubating at 65° C. for 75 minutes. After completion of the reaction, 5 μl was fractioned from each reaction liquid and subjected to a 2.0% agarose gel electrophoresis. Then the gel was stained with ethidium bromide to verify the presence or absence of the amplification product under UV irradiation. The results were shown in FIG. 14.

Figure 14:
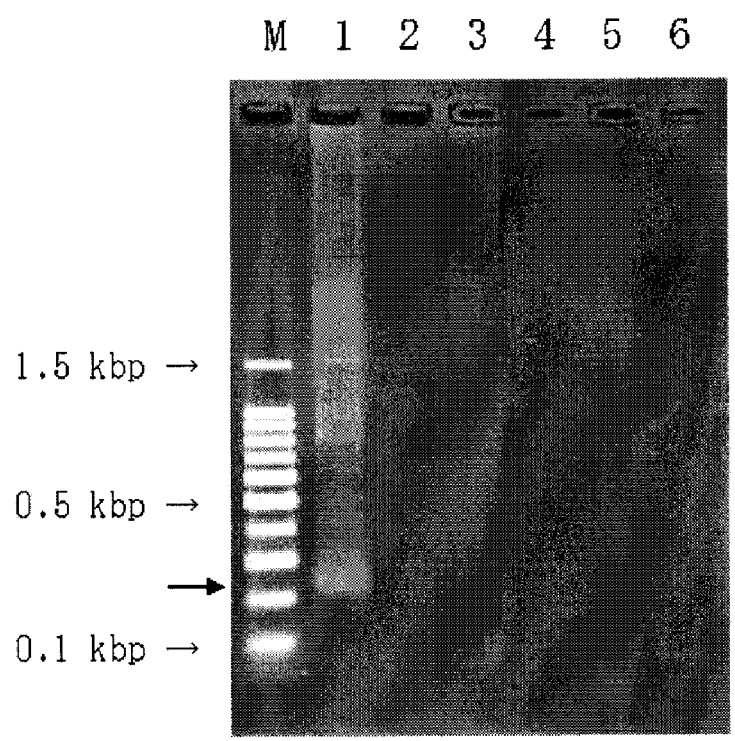
FIG. 14 is a figure showing a result in which essential components of the reaction composition of the nucleic acid amplification method of the present invention were examined and analyzed by an agarose electrophoresis image.

In FIG. 14, the lane 1 and lane M is molecular weight size marker 100 bp DNA Ladder (mfd. by TOYOBO Corporation), lane 1 is the result by the EVA reaction liquid which contains all of the components and lanes 2 to 6 are the result by the reaction liquids 2 to 6 which does not contain any one of the components. The components contained in each EVA reaction liquid are shown in Table 1.

TABLE 1

Component contained (+) and component not contained (−) in each EVA reaction liquid of Example 8

| EVA reaction liquid (lane no.) | Bst DNA polymerase | Endonuclease V | Primer set | dNTP | Template DNA |
|---|---|---|---|---|---|
| 1 | + | + | + | + | + |
| 2 | − | + | + | + | + |
| 3 | + | − | + | + | + |

TABLE 1-continued

Component contained (+) and component not contained (−)
in each EVA reaction liquid of Example 8

| EVA reaction liquid (lane no.) | Bst DNA polymerase | Endonuclease V | Primer set | dNTP | Template DNA |
|---|---|---|---|---|---|
| 4 | + | + | − | + | + |
| 5 | + | + | + | − | + |
| 6 | + | + | + | + | − |

As a result of this, a band was detected at around the expected size in the EVA reaction liquid 1 which contains all of the components (lane 1). Thus, it could be known that the object amplification product was obtained. On the other hand, the amplification product was not detected in the reaction liquids 2 to 6 (lanes 2 to 6) which do not contain one of the components. Accordingly, it was found that the presence of DNA polymerase, endonuclease V, primers, dNTP and template DNA in the reaction liquid is necessary for forming the amplification product by the EVA reaction.

Example 9

Amplification using one kind of primer

EVA was carried out using one kind of primer. The oligonucleotide shown by SEQ ID NO:11 or 12 was used as the primer.

EVA reaction liquid was prepared by the following procedure. Firstly, reaction liquid containing all of the components excluding the two kinds of enzymes (Bst DNA polymerase and mutation type Tma endonuclease V) was prepared to be a total volume of 46 μl. Next, the reaction liquid was kept at 95° C. for 5 minutes and then cooled on ice. Subsequently, the Bst DNA polymerase and mutation type Tma endonuclease V were added to the reaction liquid and mixed, and 50 μl in total volume of EVA reaction liquid [final composition: 10 mM HEPES buffer (pH 7.4), 4 mM magnesium chloride, 1 mM dithiothreitol, 100 mM potassium acetate, 0.4 mM of each of dNTP (dATP, dCTP, dGTP and dTTP), 0.5 mM betaine, 16 pmol of a primer (the primer of SEQ ID NO:11 or 12), 20 fmol of pUC18, 16 U of Bst DNA polymerase (mfd. by New England Biolabs), 3.8 pmol of mutation type Tma endonuclease V, ultrapure water] was finally prepared.

The above-mentioned EVA reaction liquid was allowed to undergo the reaction by incubating at 65° C. for 3 hours. After completion of the reaction, a 5 μl was fractioned from each reaction liquid and subjected to a 2.0% agarose gel electrophoresis. Then the gel was stained with ethidium bromide to verify the presence or absence of the amplification product under UV irradiation. The results were shown in FIG. 15, lanes 1 to 4.

Figure 15:
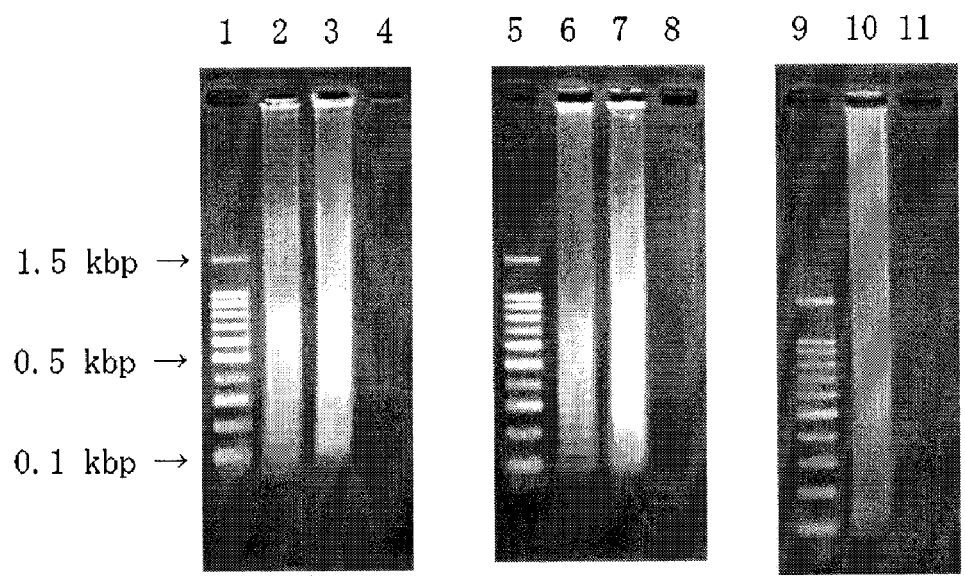
FIG. 15 is a figure showing an agarose electrophoresis image of an amplification product obtained by the nucleic acid amplification method of the present invention using one kind of primer.

In FIG. 15, the lane 1 is molecular weight size marker 100 bp DNA Ladder (mfd. by TOYOBO Corporation); lane 2 is the EVA amplification product when the primer of SEQ ID NO:11 was used; lane 3 is the EVA amplification product when the primer of SEQ ID NO:12 was used; and lane 4 is a sample in which the primer was not added to the reaction liquid. In the lanes 2 and 3, the amplification product was detected over the entire lanes so that amplification of nucleic acid by EVA by the use of one kind of primer was shown.

Also, the EVA reaction was carried out by the same above-mentioned procedure using 2 fmol of pUC18 as the template. The electrophoresis results of that case are shown in FIG. 15, lanes 5 to 8. In FIG. 15, lane 5 is molecular weight size marker 100 bp DNA Ladder; lane 6 is the EVA amplification product when the primer of SEQ ID NO:11 was used; lane 7 is the EVA amplification product when the primer of SEQ ID NO:12 was used; and lane 8 is a sample in which the primer was not added to the reaction liquid. Also in this case, in the lanes 6 and 7, the amplification product was detected over the entire lanes so that amplification of nucleic acid by EVA by the use of one kind of primer was shown. Additionally, the electrophoresis results of a negative control (2 hours of the reaction time) in which the template was not added to the reaction liquid in the same EVA reaction which used the primer of SEQ ID NO:11 are shown in FIG. 15, lanes 9 to 11.

In FIG. 15, lane 9 is molecular weight size marker 100 bp DNA Ladder; lane 10 is a sample in which 20 fmol of the template was added to the reaction liquid; and lane 11 is a sample to which the template was not added. While the amplification was detected in the lane 10, it was confirmed in the lane 11 that the amplification product is not formed when the template is not present during the reaction.

Example 10

EVA Under Various Reaction Composition Conditions (1) Amount of Endonuclease V

EVA was carried out by setting the amount of endonuclease V in the EVA reaction liquid to a range of from 3.8 to 77 pmol. Firstly, a reaction liquid was prepared by the following procedure. Reaction liquid containing all of the components excluding the enzymes (Bst DNA polymerase and mutation type Tma endonuclease V) was prepared to be a total volume of 44 μl. Next, the reaction liquid was kept at 95° C. for 5 minutes and then cooled on ice. Subsequently, the Bst DNA polymerase and mutation type Tma endonuclease V were added to the reaction liquid and mixed, and 50 μl in total volume of EVA reaction liquid [final composition: 10 mM HEPES buffer (pH 7.4), 5 mM magnesium chloride, 1 mM dithiothreitol, 100 mM potassium acetate, 0.4 mM of each of dNTP (dATP, dCTP, dGTP and dTTP), 4 pmol of each primer (the primer of SEQ ID NOs:11 and 12), 20 fmol of pUC18, 16 U of Bst DNA polymerase (mfd. by New England Biolabs), a certain amount of mutation type Tma endonuclease V within the range of from 19 to 77 pmol, ultrapure water] was finally prepared. The thus prepared these EVA reaction liquids were allowed to undergo the reaction by incubating at 65° C. for 1 hour.

Also, by the same procedure as described in the above, 50 μl in total volume of EVA reaction liquid [final composition: 10 mM HEPES buffer (pH 7.4), 4 mM magnesium chloride, 1 mM dithiothreitol, 100 mM potassium acetate, 0.4 mM of each of dNTP (dATP, dCTP, dGTP and dTTP), 16 pmol of each primer, 20 fmol of pUC18, 16 U of Bst DNA polymerase (mfd. by New England Biolabs), 0 or 3.8 pmol of mutation type Tma endonuclease V, ultrapure water] was finally prepared. The thus prepared these EVA reaction liquids were allowed to undergo the reaction by incubating at 65° C. for 90 minutes.

After completion of the reaction, a 5 μl was fractioned from each EVA reaction liquid and subjected to a 2.0% agarose gel electrophoresis. Then the gel was stained with ethidium bromide to verify the presence or absence of the amplification product under UV irradiation. Results of the electrophoresis at that time are shown in FIG. 16.

Figure 16:
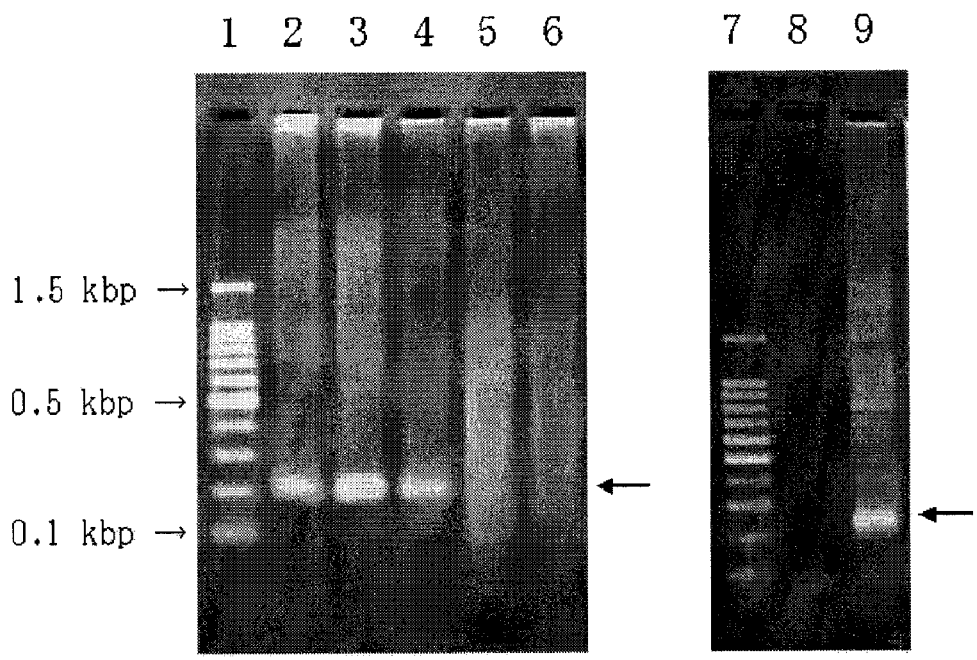
FIG. 16 is a figure showing a result of analyzing, by an agarose electrophoresis image, an amplification product amplified by the method of the present invention.

In FIG. 16, the lanes 1 and 7 are molecular weight size marker 100 bp DNA Ladder (mfd. by TOYOBO) and lanes 2 to 6 are results when the amount of endonuclease V was set to be 19, 29, 38, 58 and 77 pmol, respectively. Also, lane 8 is a result in which endonuclease V was not added, and lane 9 is a result in which the amount of endonuclease V was set to be 3.8 pmol. Under the conditions carried out in this case, a single band (about 240 bp) of specific amplification product was formed (lanes 2, 3, 4 and 9). Additionally, the amplification was not observed at all when endonuclease V was not added (lane 8).

(2) Amount of Primer and Amount of Template

EVA was carried out by preparing EVA reaction liquids having different amount of primers. Firstly, reaction liquid containing all of the components excluding the enzymes was prepared to be a total volume of 46 µl. Next, the reaction liquid was kept at 95° C. for 5 minutes and then cooled on ice. Subsequently, the Bst DNA polymerase and mutation type Tma endonuclease V were added to the reaction liquid and mixed, and 50 µl in total volume of EVA reaction liquid [final composition: 10 mM HEPES buffer (pH 7.4), 5 mM magnesium chloride, 1 mM dithiothreitol, 100 mM potassium acetate, 0.4 mM of each of dNTP (dATP, dCTP, dGTP and dTTP), 2, 4 or 8 pmol of each primer (the primer of SEQ ID NOs:11 and 12), 2 fmol of pUC18, 16 U of Bst DNA polymerase (mfd. by New England Biolabs), 19 pmol or 29 pmol of mutation type Tma endonuclease V, ultrapure water] was finally prepared.

Also, by the same procedure as described in the above, EVA reaction liquid with varied amount of the template [final composition: 10 mM HEPES buffer (pH 7.4), 4 mM magnesium chloride, 1 mM dithiothreitol, 100 mM potassium acetate, 0.4 mM of each of dNTP (dATP, dCTP, dGTP and dTTP), 16 pmol of each primer, 200 amol or 20 amol of pUC18, 16 U of Bst DNA polymerase (mfd. by New England Biolabs), 19 pmol of mutation type Tma endonuclease V, ultrapure water] was prepared.

The above-mentioned EVA reaction liquids were allowed to undergo the reaction by incubating at 65° C. for 1 hour. After completion of the reaction, a 5 µl was fractioned from each reaction liquid and subjected to a 2.0% agarose gel electrophoresis and then the gel was stained with ethidium bromide to verify the presence or absence of the amplification product under UV irradiation. The results were shown in FIG. 17.

Figure 17:
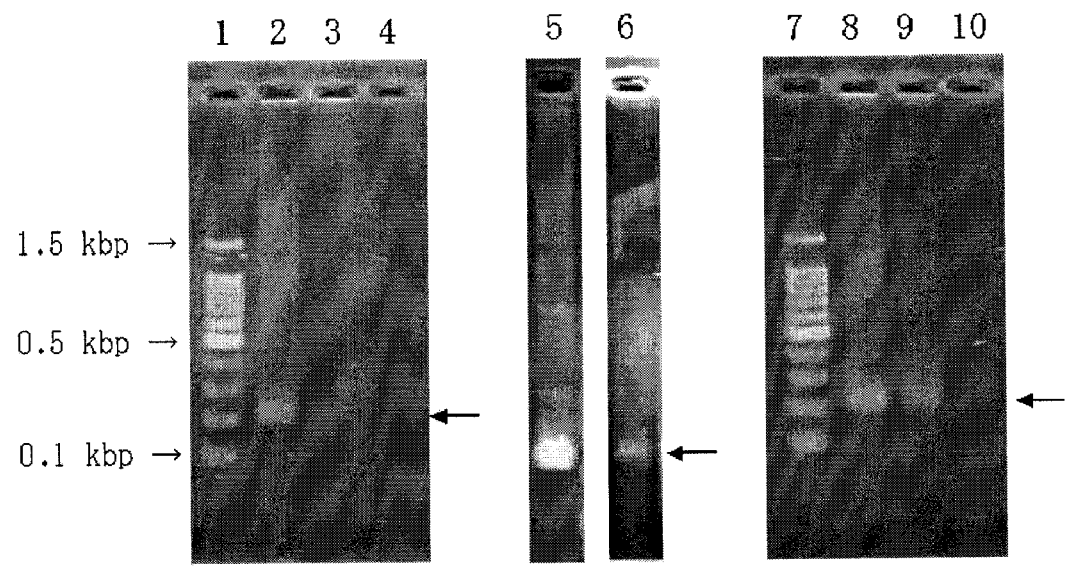
FIG. 17 is a figure showing a result of analyzing, by an agarose electrophoresis image, an amplification product amplified by the method of the present invention.

In FIG. 17, lanes 1 and 7 are molecular weight size marker 100 bp DNA Ladder and lanes 2 to 4 are results when 19 pmol of endonuclease V and respectively 8, 4 and 2 pmol of primers were used. Also, the results of the use of 19 pmol of endonuclease V, 16 pmol of primers and 200 amol and 20 amol of the template are lanes 5 and 6, respectively. Lanes 8 to 10 are results when 29 pmol of endonuclease V and respectively 8, 4 and 2 pmol of primers were used. From these results, it was found that a single band (about 240 bp) of specific amplification product can be obtained when from 4 to 16 pmol of the primers and 20 amol, 200 amol or 2 fmol amount of the template were used under the above-mentioned conditions.

(3) Magnesium Chloride Concentration and dNTP Concentration

Nucleic acid was amplified by EVA by setting the magnesium chloride concentration in the reaction liquid to be a range of from 2 to 12 mM. Firstly, EVA reaction liquid was prepared by the following procedure. Reaction liquid containing all of the components excluding the enzymes (Bst DNA polymerase and mutation type Tma endonuclease V) was prepared to be a total volume of 47 µl. Next, the reaction liquid was kept at 95° C. for 5 minutes and then cooled on ice. Subsequently, the Bst DNA polymerase and mutation type Tma endonuclease V were added to the reaction liquid and mixed, and 50 µl in total volume of EVA reaction liquid [final composition: 10 mM HEPES buffer (pH 7.4), 2, 4, 5, 6, 7, 8 or 12 mM magnesium chloride, 1 mM dithiothreitol, 100 mM potassium acetate, 0.4 mM of each of dNTP (dATP, dCTP, dGTP and dTTP), 16 pmol of each primer (the primer of SEQ ID NOs:11 and 12), 200 amol of pUC18, 16 U of Bst DNA polymerase (mfd. by New England Biolabs), 19 pmol of mutation type Tma endonuclease V, ultrapure water] was finally prepared.

The above-mentioned EVA reaction liquid was allowed to undergo the reaction by incubating at 65° C. for 1 hour. After completion of the reaction, 5 µl was fractioned from each reaction liquid and subjected to a 2.0% agarose gel electrophoresis. The agarose gel after electrophoresis was stained with ethidium bromide and then the presence or absence of the amplification product was verified under UV irradiation. As a result, it was found that the object amplification product can be detected most distinctively when final concentration of magnesium chloride is 4 mM, under the above-mentioned conditions.

Next, nucleic acid was amplified by EVA by setting concentration of dNTP (dATP, dCTP, dGTP and dTTP) in the reaction liquid to be 0.2 to 1.0 mM. Firstly, EVA reaction liquid [final composition: 10 mM HEPES buffer (pH 7.4), 4 mM magnesium chloride, 1 mM dithiothreitol, 100 mM potassium acetate, 0.2, 0.4, 0.6, 0.8 or 1.0 mM of each dNTP, 16 pmol of each primer, 200 amol of pUC18, 16 U of Bst DNA polymerase (mfd. by New England Biolabs), 19 pmol of mutation type Tma endonuclease V, ultrapure water] was prepared by the same procedure described in the above.

The thus prepared these EVA reaction liquids were allowed to undergo the reaction by incubating at 65° C. for 1 hour. After completion of the reaction, 5 µl was fractioned from each EVA reaction liquid and subjected to a 2.0% agarose gel electrophoresis. The agarose gel after electrophoresis was stained with ethidium bromide, and then the presence or absence of the amplification product was verified under UV irradiation. As a result, it was found that the object amplification product can be detected distinctively when final concentration of each dNTP is 0.2 to 0.4 mM, under the above-mentioned conditions.

The results when 4 mM of magnesium chloride, 0.4 mM of each dNTP and 200 and 20 amol of the template were respectively used are shown in the lanes 5 and 6 in FIG. 17 (other reaction compositions and reaction conditions are the same as in the above).

(4) Kind and Concentration of Salts and Concentration of Betaine

Nucleic acid was amplified by EVA, by using potassium acetate as the salts to be coexisted in the reaction liquid and setting its concentration to be 50 to 150 mM. Firstly, EVA reaction liquid was prepared by the following procedure. Reaction liquid containing all of the components excluding the enzymes (Bst DNA polymerase and mutation type Tma endonuclease V) was prepared to be a total volume of 46 µl. Next, the reaction liquid was kept at 95° C. for 5 minutes and then cooled on ice. Subsequently, the Bst DNA polymerase and mutation type Tma endonuclease V were added to the reaction liquid and mixed, and 50 µl in total volume of EVA reaction liquid [final composition: 10 mM HEPES buffer (pH 7.4), 4 mM magnesium chloride, 1 mM dithiothreitol, 50, 75, 100, 125 or 150 mM potassium acetate, 0.4 mM of each of dNTP (dATP, dCTP, dGTP and dTTP), 16 pmol of each primer (the primer of SEQ ID NOs:11 and 12), 200 amol of pUC18, 16 U of Bst DNA polymerase (mfd. by New England Biolabs), 3.8 pmol of mutation type Tma endonuclease V, ultrapure water] was finally prepared.

The above-mentioned EVA reaction liquid was allowed to undergo the reaction by incubating at 65° C. for 90 minutes or 2 hours. After completion of the reaction, 5 μl was fractioned from each reaction liquid and subjected to a 2.0% agarose gel electrophoresis. The agarose gel after electrophoresis was stained with ethidium bromide, and then the presence or absence of the amplification product was verified under UV irradiation. As a result, it was found that the object amplification product can be detected when final concentration of potassium acetate is within the range of from 100 to 125 mM, under the above-mentioned conditions.

Also, by the same procedure as described in the above and using potassium chloride (10 to 130 mM) as the salts to be coexisted in the reaction liquid, EVA reaction liquid [final composition: 10 mM HEPES buffer (pH 7.4), 4 mM magnesium chloride, 1 mM dithiothreitol, 10, 30, 50, 70, 90, 110 or 130 mM potassium chloride, 0.4 mM of each of dNTP (dATP, dCTP, dGTP and dTTP), 16 pmol of each primer, 200 amol of pUC18, 16 U of Bst DNA polymerase, 7.7 pmol of mutation type Tma endonuclease V, ultrapure water] was prepared.

The above-mentioned EVA reaction liquid was allowed to undergo the reaction by incubating at 65° C. for 2 hours. After completion of the reaction, 5 μl was fractioned from each reaction liquid and subjected to a 2.0% agarose gel electrophoresis and then the gel was stained with ethidium bromide to verify the presence or absence of the amplification product under UV irradiation. As a result, the object amplification product was confirmed when final concentration of potassium chloride was from 70 to 90 mM, under the above-mentioned conditions.

Additionally, by the same procedure as described in the above and setting the concentration of betaine (N,N,N-trimethylglycine) in the EVA reaction liquid to be 0.5 to 1.5 M, EVA reaction liquid [final composition: 10 mM HEPES buffer (pH 7.4), 4 mM magnesium chloride, 1 mM dithiothreitol, 100 mM potassium acetate, 0.5, 1.0 or 1.5 M of betaine, 0.4 mM of each of dNTP (dATP, dCTP, dGTP and dTTP), 16 pmol of each primer (the primers of SEQ ID NOs:11 and 12), 200 amol of pUC18, 16 U of Bst DNA polymerase, 3.8 pmol of mutation type Tma endonuclease V, ultrapure water] was prepared.

The above-mentioned EVA reaction liquid was allowed to undergo the reaction by incubating at 65° C. for 90 minutes. After completion of the reaction, 5 μl was fractioned from each reaction liquid and subjected to a 2.0% agarose gel electrophoresis and then the gel was stained with ethidium bromide to verify the presence or absence of the amplification product under UV irradiation. The results were shown in FIG. 18.

Figure 18:
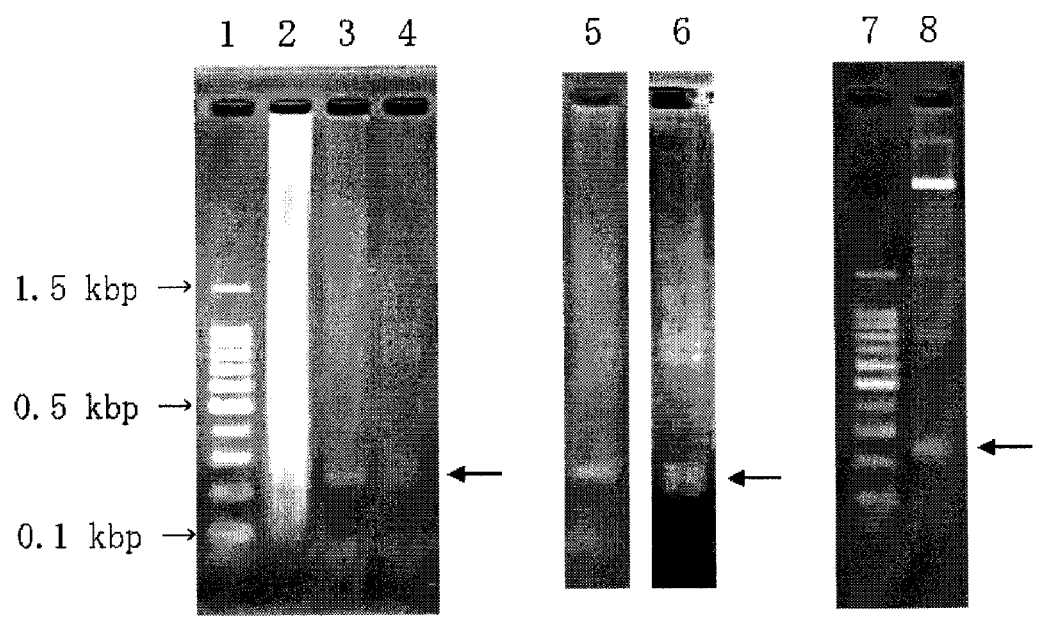
FIG. 18 is a figure showing a result of analyzing, by an agarose electrophoresis image, an amplification product amplified by the method of the present invention.

In FIG. 18, the lane 1 is molecular weight size marker 100 bp DNA Ladder (mfd. by TOYOBO Co., Ltd.); lane 2 is a result of using 1.5 M in final concentration of betaine; lane 3 is a result of using 1.0 M in final concentration of betaine; and lane 4 is a result of using 0.5 M in final concentration of betaine. From the result, it was found that the object amplification product can be obtained when the final concentration of betaine is from 0.5 to 1.0 M.

(5) Incubation Temperature

Nucleic acid was amplified by EVA by setting the incubation temperature of the reaction to be a range of from 48 to 70° C. Firstly, reaction liquid was prepared by the following procedure. Reaction liquid containing all of the components excluding the enzymes (Bst DNA polymerase and mutation type Tma endonuclease V) was prepared to be a total volume of 46 μl. Next, the reaction liquid was kept at 95° C. for 5 minutes and then cooled on ice. Subsequently, the Bst DNA polymerase and mutation type Tma endonuclease V were added to the reaction liquid and mixed, and 50 μl in total volume of EVA reaction liquid [final composition: 10 mM HEPES buffer (pH 7.4), 4 mM magnesium chloride, 1 mM dithiothreitol, 100 mM potassium acetate, 0.4 mM of each of dNTP (dATP, dCTP, dGTP and dTTP), 16 pmol of each primer (the primer of SEQ ID NOs:11 and 12), 20 amol of pUC18, 16 U of Bst DNA polymerase (mfd. by New England Biolabs), 19 pmol of mutation type Tma endonuclease V, ultrapure water] was finally prepared.

Two or more of the above-mentioned EVA reaction liquids were prepared and allowed to undergo the reaction by respectively keeping them at a different constant temperature within the range of from 48 to 70° C. on a gradient thermal cycler MJ Opticon (mfd. by MJ Japan) and incubating for 1 hour. After completion of the reaction, 5 μl was fractioned from each reaction liquid and subjected to a 2.0% agarose gel electrophoresis. Then the gel was stained with ethidium bromide to verify the presence or absence of the amplification product under UV irradiation. As a result, good amplification was confirmed when the incubation temperature is 64° C., under the above-mentioned conditions.

Example 11

EVA using a *Bacillus caldotenax*-Derived DNA Polymerase

Nucleic acid was amplified by EVA using a *Bacillus caldotenax*-derived 5'→3' exonuclease-deficient DNA polymerase (Bca DNA polymerase) as the strand displacement type DNA polymerase. A reaction liquid was prepared by the following procedure. Firstly, a reaction liquid containing all of the components excluding the enzymes was prepared to be a total volume of 45.5 μl. Next, the reaction liquid was kept at 95° C. for 5 minutes and then cooled on ice. Subsequently, the Bca DNA polymerase and mutation type Tma endonuclease V were added to the reaction liquid and mixed, and 50 μl in total volume of EVA reaction liquid [final composition: 10 mM HEPES buffer (pH 7.4), 4 mM magnesium chloride, 1 mM dithiothreitol, 100 mM potassium acetate, 0.4 mM of each of dNTP (dATP, dCTP, dGTP and dTTP), 16 pmol of each primer (the primer of SEQ ID NOs:11 and 12), 2 fmol of pUC18, 5 U of Bca DNA polymerase (BcaBEST DNA polymerase, mfd. by Takara Bio), 3.8 pmol of mutation type Tma endonuclease V, ultrapure water] was finally prepared.

The above-mentioned EVA reaction liquid was allowed to undergo the reaction by incubating at 60° C. for 1 hour. After completion of the reaction, 5 μl was fractioned from the reaction liquid and subjected to a 2.0% agarose gel electrophoresis. The agarose gel after electrophoresis was stained with ethidium bromide, and then the presence or absence of the amplification product was verified under UV irradiation. An electrophoresis image of this case is shown in the lane 5 of FIG. 18. As a result, it was found that the amplification product was obtained since a specific band having the expected length (about 240 bp) was confirmed.

Example 12

EVA Using Outer Primers

Nucleic acid was amplified by EVA using outer primers. The cyclic plasmid pUC18 was used as the template, and the oligonucleotides shown by SEQ ID NOs:11 and 12 were used as the primers and the oligonucleotides shown by SEQ ID NOs:15 and 16 were used as the outer primers. The outer primer of SEQ ID NO:15 was designed in such a manner that it anneals on the pUC18 template at a position of about 17 bases upstream from the region where the primer of SEQ ID NO:11 anneals. Also, the outer primer of SEQ ID NO:16 was designed in such a manner that it anneals on the pUC18 template at a position of about 17 bases upstream from the region where the primer of SEQ ID NO:12 anneals.

EVA reaction liquid was prepared by the following procedure. Firstly, reaction liquid containing all of the components excluding the enzymes was prepared to be a total volume of 46 µl. Next, the reaction liquid was kept at 95° C. for 5 minutes and then cooled on ice. Subsequently, the Bst DNA polymerase and mutation type Tma endonuclease V were added to the reaction liquid and mixed, and 50 µl in total volume of EVA reaction liquid [final composition: 10 mM HEPES buffer (pH 7.4), 4 mM magnesium chloride, 1 mM dithiothreitol, 100 mM potassium acetate, 0.5 mM betaine, 0.4 mM of each of dNTP (dATP, dCTP, dGTP and dTTP), 16 pmol of the primer of SEQ ID NO:11, 16 pmol of the primer of SEQ ID NO:12, 4 pmol of the outer primer of SEQ ID NO:15, 4 pmol of the outer primer of SEQ ID NO:16, 20 amol of pUC18, 16 U of Bst DNA polymerase (mfd. by New England Biolabs), 3.8 pmol of mutation type Tma endonuclease V, ultrapure water] was finally prepared.

The above-mentioned EVA reaction liquid was incubated at 65° C. for 90 minutes. After completion of the reaction, 5 µl was fractioned from the reaction liquid and subjected to a 2.0% agarose gel electrophoresis. The gel was stained with ethidium bromide, and then the presence or absence of the amplification product was verified under UV irradiation. The results were shown in the lane 6 of FIG. 18. As a result of this, it was found that the amplification product was obtained since a specific band having the expected length (about 240 bp) was confirmed.

Example 13

Amplification of Target Nucleic Acid in the Coexistence of Non-Target Nucleic Acid Using the cyclic plasmid pUC18 as the template having a target nucleic acid sequence, the nucleic acid was amplified by EVA under a condition in which a nucleic acid which is not the target (non-target nucleic acid) is present in a large amount.

EVA reaction liquid was prepared by the following procedure. Firstly, a reaction liquid containing all of the components excluding the enzymes was prepared to be a total volume of 46 µl. Next, the reaction liquid was kept at 95° C. for 5 minutes and then cooled on ice. Subsequently, the Bst DNA polymerase and mutation type Tma endonuclease V were added to the reaction liquid and mixed, and 50 µl in total volume of EVA reaction liquid [final composition: 10 mM HEPES buffer (pH 7.4), 4 mM magnesium chloride, 1 mM dithiothreitol, 100 mM potassium acetate, 0.5 mM betaine, 0.4 mM of each of dNTP (dATP, dCTP, dGTP and dTTP), 16 pmol of the primer of SEQ ID NO:11, 16 pmol of the primer of SEQ ID NO:12, 2 fmol of pUC18, 1 µg of pET16b, 16 U of Bst DNA polymerase (mfd. by New England Biolabs), 3.8 pmol of mutation type Tma endonuclease V, ultrapure water] was finally prepared. The cyclic plasmid pET16b used herein does not have a nucleic acid sequence which becomes the target of the used primers. Additionally, the amount of the used pET16b is such a large amount that it can be observed by electrophoresis without amplification.

The above-mentioned EVA reaction liquid was incubated at 65° C. for 90 minutes. After completion of the reaction, 5 µl was fractioned from the reaction liquid and subjected to a 2.0% agarose gel electrophoresis. The gel was stained with ethidium bromide and then the presence or absence of the amplification product was verified under UV irradiation, with the results shown in the lane 8 of FIG. 18. In this connection, the lane 7 of FIG. 18 is a molecular weight size marker 100 bp DNA Ladder (mfd. by TOYOBO Corporation). As a result of this, in addition to a band derived from a large amount of the pET16b having a large molecular weight, a specific band having the expected length (about 240 bp) was confirmed as the amplification product. Based on this, it was found that the target nucleic acid sequence alone is specifically amplified in the EVA reaction liquid, even when a non-target nucleic acid sequence coexists in large excess based on the presence of a very small amount of the target nucleic acid sequence.

Example 14

Amplification Using Various Mutation Type Endonuclease V

The recombinant DNA (pET16 TmaEVM2) prepared in Example 1(2), having the mutation type endonuclease V gene into which the Y80A and D105A mutations were introduced, was used as the template, and genes of mutation type endonuclease V in which the amino acid $Z_2$ was further changed to other amino acids were prepared by the same method of Example 1(2).

Using the oligonucleotides shown in Table 2 as the primers for mutation introducing use, a recombinant DNA having the gene of a mutation type endonuclease V in which the amino acid $Z_2$ is glycine, arginine, histidine, glutamic acid, asparagine or glutamine was prepared (to be called pET16 TmaEVM2-2, pET16 TmaEVM2-3, pET16 TmaEVM2-4, pET16 TmaEVM2-5, pET16 TmaEVM2-6 and pET16 TmaEVM2-7, respectively).

TABLE 2

Mutation introducing primer sequences

| Recombinant DNA | Mutation introducing primer sequence (5'-3') | SEQ ID NO | Amino acid $Z_2$ |
|---|---|---|---|
| pET16 TmaEVM2-2 | GCTGAGAACGAAACCCGGTGTTGTGGTCTTCGATG<br>CATCGAAGACCACAACACCGGGTTTCGTTCTCAGC | 17<br>18 | Glycine |
| pET16 TmaEVM2-3 | AAGCTGAGAACGAAACCCCGTGTTGTGGTCTTCGATGG<br>CCATCGAAGACCACAACACGGGGTTTCGTTCTCAGCTT | 19<br>20 | Arginine |
| pET16 TmaEVM2-4 | GCTGAGAACGAAACCCCATGTTGTGGTCTTCGA<br>TCGAAGACCACAACATGGGGTTTCGTTCTCAGC | 21<br>22 | Histidine |
| pET16 | CTGAGAACGAAACCCGAGGTTGTGGTCTTCGATGG | 23 | Glutamic |

TABLE 2-continued

Mutation introducing primer sequences

| Recombinant DNA | Mutation introducing primer sequence (5'-3') | SEQ ID NO | Amino acid $Z_2$ |
|---|---|---|---|
| TmaEVM2-5 | CCATCGAAGACCACAACCTCGGGTTTCGTTCTCAG | 24 | acid |
| pET16 TmaEVM2-6 | AGCTGAGAACGAAACCCAATGTTGTGGTCTTCGAT ATCGAAGACCACAACATTGGGTTTCGTTCTCAGCT | 25 26 | Asparagine |
| pET16 TmaEVM2-7 | AGCTGAGAACGAAACCCCAGGTTGTGGTCTTCGATGG CCATCGAAGACCACAACCTGGGGTTTCGTTCTCAGCT | 27 28 | Glutamine |

Expression and purification of each endonuclease V was further carried out by the same method of Example 1(3). In this manner, mutation type endonuclease V enzyme preparations in which the amino acid $Z_2$ is glycine, arginine, histidine, glutamic acid, asparagine and glutamine were obtained (to be called as TmaEVM2-2, TmaEVM2-3, TmaEVM2-4, TmaEVM2-5, TmaEVM2-6 and TmaEVM2-7, respectively). It was confirmed by a method similar to the method for measuring the cleavage activity of endonuclease V, disclosed in Japanese Patent Application 2005-308533, that each of these enzymes has higher specificity than that of the wild type endonuclease V and has high specificity equal to or higher than that of the mutation type endonuclease V prepared in Example 1 in which Y80A and D105A mutations were introduced. When EVA was carried out using these enzymes by the same method as Example 8, it was shown that all of these enzymes can be used in EVA. Additionally, it was shown that the mutation type endonuclease V in which the amino acid $Z_2$ is glutamic acid, asparagine or glutamine (TmaEVM2-5, TmaEVM2-6 or TmaEVM2-7) has further higher specificity than that of the mutation type endonuclease V prepared in Example 1 and can therefore be used in EVA more preferably.

Example 15

Use of (α-S) Nucleotide-Containing Primers

The same EVA reaction of Example 8 was carried out using primer sets containing the (1-S) nucleotide at various positions and ratios. The primer sets used and the amplification results are shown in Table 3.

TABLE 3

Amplification using (α-S) nucleotide-containing primers

| Primer set | Sequence (5' - 3') [a] | SEQ ID NO | % S [b] | Amp [c] |
|---|---|---|---|---|
| S01 | GGATGTGCTGCAAGGCGAT*IAAGTTGGGTAACGCCAGGGTTT | 29 | 5% | + |
| | ACTCATTAGGCACCCCAGGCT*ITACACTTTATGCTTCCGGCTCG | 30 | 5% | |
| S02 | G*GATGTGCTGCAAGGCGATIAAGTTGGGTAACGCCAGGGTTT | 31 | 5% | + |
| | A*CTCATTAGGCACCCCAGGCTITACACTTTATGCTTCCGGCTCG | 32 | 5% | |
| S03 | G*GAT*GTG*CTG*CAA*GGC*GAT*IAAGTTGGGTAACGCCAGGGTTT | 33 | 37% | + |
| | A*CTC*ATT*AGG*CAC*CCC*AGG*CT*ITACACTTTATGCTTCCGGCTCG | 34 | 38% | |
| S04 | GG*A*TG*TGC*TGC*A*AGGCG*A*T*IAAGTGGGTAACGCCAGGGTTT | 35 | 47% | + |
| | AC*TC*A*T*T*AGGC*ACCCC*AGGC*T*ITACACTTTATGCTTCCGGCTCG | 36 | 43% | |
| S05 | G*GA*TG*TG*CT*GC*AA*GG*CG*AT*IAAGTTGGGTAACGCCAGGGTTT | 37 | 53% | + |
| | A*CT*CA*TT*AG*GC*AC*CC*CA*GG*CT*ITACACTTTATGCTTCCGGCTCG | 38 | 52% | |
| S06 | G*G*A*T*G*T*G*C*T*G*C*A*A*G*G*C*G*A*T*IAAGTTGGGTAACGCCAGGGTTT | 39 | 100% | - |
| | A*C*T*C*A*T*T*A*G*G*C*A*C*C*C*C*A*G*G*C*T*ITACACTTTATGCTTCCGGCTCG | 40 | 100% | |

[a] Phosphorothioate group (*)

[b] Ratio (%) of (α-S) nucleotide in the upstream side from base X

[c] Result of amplification by EVA; +, amplification; -, no amplification

As can be seen from Table 3, the amplification product was obtained by the reaction using the primer sets SO1 to SO5. Namely, the amplification product was obtained by the primer set in which at least one or more, about 60% or less, of nucleotides among total nucleotides in the upstream side region of the base X of the primers are (α-S) nucleotides. On the other hand, the amplification did not occur by the primers in which all nucleotides in the upstream side region of the base X of the primers are (α-S) nucleotides (primer set SO6).

Example 16

Use of Single-Stranded Nucleic Acid Binding Protein

EVA was carried out under the same reaction conditions of Example 8, by further adding from 0.5 to 3 μg of an *Escherichia coli* SSB protein (SIGMA), an *Escherichia coli* RecA protein (NEB) or a T4 phage gp32 (NEB) respectively to 50 μl of EVA reaction liquid having the same reaction composition of Example 8. As a result of this, the amplification reaction occurred within the tested range, on the *Escherichia coli* RecA protein and T4 phage gp32. In the case of the *Escherichia coli* SSB protein, the amplification reaction did not occur when it was added in an amount of larger than 1.5 μg, which shows that the EVA reaction is inhibited. Accordingly, it was found that suitable amount of the single-stranded nucleic acid binding protein to be used in EVA is within the range of from about 0.5 to 1.5 μg for the *Escherichia coli* SSB protein and is within the range of from about 0.5 to 3 μg for *Escherichia coli* RecA protein and T4 phage gp32, in 50 μl of the reaction mixture.

INDUSTRIAL APPLICABILITY

The nucleic acid amplification method of the present invention is industrially very useful since it has advantages of the following (1) to (9).
(1) It can provide a nucleic acid sequence amplification method for achieving synthesis and amplification of a nucleic acid under an isothermal reaction condition which does not require an expensive temperature cycling device;
(2) Since it is sufficient for the primer used to contain at least one base X, there is no limitation for primer designing;
(3) It can provide a nucleic acid sequence amplification method in which it is not necessary to use a modified dNTP [α-S-dNTP or the like for example) which results in high cost, in a large amount as a substrate for DNA synthesis;
(4) It can provide a nucleic acid sequence amplification method which does not produce an amplification product having limitations for its use in subsequent steps, such as a nucleic acid fragment containing a large amount of modified nucleotides, a mixture of nucleic acid fragments having different lengths due to repetitions of the target sequence;
(5) It can provide a nucleic acid sequence amplification method which can use an optional sequence region as the target independently from whether or not a specific restriction enzyme recognition site is present in the target sequence;
(6) It can provide a nucleic acid sequence amplification method which does not require an additional pre-step for preparing a cyclic template nucleic acid;
(7) It can provide a nucleic acid sequence amplification method which does not require designing of complex and limitative primer sequences for a large number of regions, for achieving amplification of certain one target sequence;
(8) It can provide a nucleic acid sequence amplification method in which it is not necessary to contain an unstable and easily degradable RNA component in the primer molecule;
(9) It can provide a nucleic acid sequence amplification method in which it is not necessary to allow cofactors such as ATP, dATP and the like as energy supplying substances for the enzyme activity to be present in the reaction in large amounts during the reaction, and it is not necessary to allow an ATP regeneration system to coexist during the reaction;
(10) It is not always necessary that all parts of the sequence of the target nucleic acid are already known, so that it is possible to obtain an amplification product containing an unknown nucleic acid sequence, using a primer designed based on the already known limited sequence information.

SEQUENCE LISTING FREE TEXT

SEQ ID NO:1: Amino acid sequence of endonuclease V.
SEQ ID NO:2: Amino acid sequence of mutation type endonuclease V.
SEQ ID NO:3: DNA designed as an upstream side primer for endonuclease V gene amplification.
SEQ ID NO:4: DNA designed as a downstream side primer for endonuclease V gene amplification.
SEQ ID NO:5: DNA designed as an oligonucleotide 1 for Y80A mutation introduction use.
SEQ ID NO:6: DNA designed as an oligonucleotide 2 for Y80A mutation introduction use.
SEQ ID NO:7: DNA designed as an oligonucleotide 1 for D105A mutation introduction use.
SEQ ID NO:8: DNA designed as an oligonucleotide 2 for D105A mutation introduction use.
SEQ ID NO:9: DNA designed as a deoxyinosine-containing primer PIT321-01. The letter i in the nucleotide sequence represents deoxyinosine.
SEQ ID NO:10: DNA designed as a deoxyinosine-containing primer PIT541-01. The letter i in the nucleotide sequence represents deoxyinosine.
SEQ ID NO:11: DNA designed as a deoxyinosine-containing primer PIT321-04. The letter i in the nucleotide sequence represents deoxyinosine.
SEQ ID NO:12: DNA designed as a deoxyinosine-containing primer PIT541-04. The letter i in the nucleotide sequence represents deoxyinosine.
SEQ ID NO:13: DNA designed as a deoxyinosine-containing primer PIT1849-02. The letter i in the nucleotide sequence represents deoxyinosine.
SEQ ID NO:14: DNA designed as a deoxyinosine-containing primer PIT2454-2. The letter i in the nucleotide sequence represents deoxyinosine.
SEQ ID NO:15: DNA designed as an outer primer PIT321-OP1.
SEQ ID NO:16: DNA designed as an outer primer PIT541-OP1.
SEQ ID NO:17: Nucleotide sequence of a primer for mutation introduction use.
SEQ ID NO:18: Nucleotide sequence of a primer for mutation introduction use.
SEQ ID NO:19: Nucleotide sequence of a primer for mutation introduction use.
SEQ ID NO:20: Nucleotide sequence of a primer for mutation introduction use.
SEQ ID NO:21: Nucleotide sequence of a primer for mutation introduction use.
SEQ ID NO:22: Nucleotide sequence of a primer for mutation introduction use.

SEQ ID NO:23: Nucleotide sequence of a primer for mutation introduction use.
SEQ ID NO:24: Nucleotide sequence of a primer for mutation introduction use.
SEQ ID NO:25: Nucleotide sequence of a primer for mutation introduction use.
SEQ ID NO:26: Nucleotide sequence of a primer for mutation introduction use.
SEQ ID NO:27: Nucleotide sequence of a primer for mutation introduction use.
SEQ ID NO:28: Nucleotide sequence of a primer for mutation introduction use.
SEQ ID NO:29: Nucleotide sequence of an (α-S)nucleotide-containing primer. The letter i in the nucleotide sequence represents deoxyinosine.
SEQ ID NO:30: Nucleotide sequence of an (α-S)nucleotide-containing primer. The letter i in the nucleotide sequence represents deoxyinosine.
SEQ ID NO:31: Nucleotide sequence of an (α-S)nucleotide-containing primer. The letter i in the nucleotide sequence represents deoxyinosine.
SEQ ID NO:32: Nucleotide sequence of an (α-S)nucleotide-containing primer. The letter i in the nucleotide sequence represents deoxyinosine.
SEQ ID NO:33: Nucleotide sequence of an (α-S)nucleotide-containing primer. The letter i in the nucleotide sequence represents deoxyinosine.
SEQ ID NO:34: Nucleotide sequence of an (α-S)nucleotide-containing primer. The letter i in the nucleotide sequence represents deoxyinosine.
SEQ ID NO:35: Nucleotide sequence of an (α-S)nucleotide-containing primer. The letter i in the nucleotide sequence represents deoxyinosine.
SEQ ID NO:36: Nucleotide sequence of an (α-S)nucleotide-containing primer. The letter i in the nucleotide sequence represents deoxyinosine.
SEQ ID NO:37: Nucleotide sequence of an (α-S)nucleotide-containing primer. The letter i in the nucleotide sequence represents deoxyinosine.
SEQ ID NO:38: Nucleotide sequence of an (α-S)nucleotide-containing primer. The letter i in the nucleotide sequence represents deoxyinosine.
SEQ ID NO:39: Nucleotide sequence of an (α-S)nucleotide-containing primer. The letter i in the nucleotide sequence represents deoxyinosine.
SEQ ID NO:40: Nucleotide sequence of an (α-S)nucleotide-containing primer. The letter i in the nucleotide sequence represents deoxyinosine.

While the present invention has been described in detail and with reference to specific embodiments thereof, it will be apparent to one skilled in the art that various changes and modifications can be made therein without departing from the spirit and scope of the present invention.

In this connection, this application is based on a Japanese patent application filed on Jul. 26, 2006 (Japanese Patent Application No. 2006-203414) and a Japanese patent application filed on May 23, 2007 (Japanese Patent Application No. 2007-136392), the entire contents thereof are incorporated by reference.

---

The invention claimed is:

1. A method for amplifying a nucleic acid sequence, which comprises the following steps (I) and (II);

(I) a step for preparing a reaction mixture comprising at least the following:
a template nucleic acid,
deoxyribonucleotide 3-phosphate,
a DNA polymerase having a strand displacement activity,
endonuclease V, and
at least one kind of primer wherein said primer is an oligonucleotide primer which has a nucleotide sequence substantially complementary with the nucleotide sequence of the template nucleic acid and also contains at least one base X which can be recognized by endonuclease V;

(II) a step for incubating the reaction mixture prepared in the step (I) for a period of time sufficient for forming an amplification product under sufficient temperature conditions wherein the following reactions are carried out:
specific annealing of the primer to the template nucleic acid;
elongation chain synthesis reaction and strand displacement reaction by the DNA polymerase; and
recognition of a first base X in a nucleic acid chain containing the first base X and a cleavage reaction of a phosphodiester bond positioned at a downstream side (3' side) of said first base X by the endonuclease V,
wherein the first base X is hypoxanthine,
wherein the endonuclease V is an endonuclease variant comprising the following mutations, based the amino acid sequence of a wild type endonuclease V of SEQ ID NO:1,
(a) the 80th-position amino acid or an amino acid of a position equivalent to the 80th-position of *Thermotoga maritima* endonuclease V is replaced with an other amino acid $Z_1$, and
(b) the 105th-position amino acid or an amino acid of a position equivalent the 105th-position of *Thermotoga maritima* endonuclease V is replaced with an other amino acid $Z_2$,
wherein the amino acid $Z_1$ is selected from the group consisting of alanine, glycine, leucine, isoleucine, valine, phenylalanine and methionine, and
wherein the amino acid $Z_2$ is selected from the group consisting of alanine, glutamic acid, asparagine, glutamine, arginine, glycine, serine, threonine and histidine.

2. A method for amplifying a nucleic acid sequence, which comprises the following steps (I) and (II);

(I) a step for preparing a reaction mixture comprising at least the following:
a template nucleic acid,
deoxyribonucleotide 3-phosphate,
a DNA polymerase having a strand displacement activity,
endonuclease V of SEQ ID NO: 2, and
at least one kind of primer wherein said primer is an oligonucleotide primer which has a nucleotide sequence substantially complementary with the nucleotide sequence of the template nucleic acid and also contains at least one base X which can be recognized by the endonuclease V;

(II) a step for incubating the reaction mixture prepared in the step (I) for a period of time sufficient for forming an amplification product under sufficient temperature conditions wherein the following reactions are carried out:
specific annealing of the primer to the template nucleic acid;
elongation chain synthesis reaction and strand displacement reaction by the DNA polymerase; and recognition of a first base X in a nucleic acid chain containing the first base X and a cleavage reaction of a phosphodiester bond positioned at a downstream side (3' side) of said first base X by the endonuclease V,
wherein the first base X is hypoxanthine.

3. The method for amplifying a nucleic acid sequence according to claim 1, wherein both of the amino acids $Z_1$ and $Z_2$ are alanine.

* * * * *

SEQUENCE LISTING

```
<160> NUMBER OF SEQ ID NOS: 40

<210> SEQ ID NO 1
<211> LENGTH: 225
<212> TYPE: PRT
<213> ORGANISM: Thermotoga maritima

<400> SEQUENCE: 1

Met Asp Tyr Arg Gln Leu His Arg Trp Asp Leu Pro Pro Glu Glu Ala
1               5                   10                  15

Ile Lys Val Gln Asn Glu Leu Arg Lys Lys Ile Lys Leu Thr Pro Tyr
            20                  25                  30

Glu Gly Glu Pro Glu Tyr Val Ala Gly Val Asp Leu Ser Phe Pro Gly
        35                  40                  45

Lys Glu Glu Gly Leu Ala Val Ile Val Val Leu Glu Tyr Pro Ser Phe
    50                  55                  60

Lys Ile Leu Glu Val Val Ser Glu Arg Gly Glu Ile Thr Phe Pro Tyr
65                  70                  75                  80

Ile Pro Gly Leu Leu Ala Phe Arg Glu Gly Pro Leu Phe Leu Lys Ala
                85                  90                  95

Trp Glu Lys Leu Arg Thr Lys Pro Asp Val Val Val Phe Asp Gly Gln
            100                 105                 110

Gly Leu Ala His Pro Arg Lys Leu Gly Ile Ala Ser His Met Gly Leu
        115                 120                 125

Phe Ile Glu Ile Pro Thr Ile Gly Val Ala Lys Ser Arg Leu Tyr Gly
    130                 135                 140

Thr Phe Lys Met Pro Glu Asp Lys Arg Cys Ser Trp Ser Tyr Leu Tyr
145                 150                 155                 160
```

```
Asp Gly Glu Glu Ile Ile Gly Cys Val Ile Arg Thr Lys Glu Gly Ser
            165                 170                 175

Ala Pro Ile Phe Val Ser Pro Gly His Leu Met Asp Val Glu Ser Ser
            180                 185                 190

Lys Arg Leu Ile Lys Ala Phe Thr Leu Pro Gly Arg Arg Ile Pro Glu
            195                 200                 205

Pro Thr Arg Leu Ala His Ile Tyr Thr Gln Arg Leu Lys Lys Gly Leu
            210                 215                 220

Phe
225

<210> SEQ ID NO 2
<211> LENGTH: 225
<212> TYPE: PRT
<213> ORGANISM: Thermotoga maritima

<400> SEQUENCE: 2

Met Asp Tyr Arg Gln Leu His Arg Trp Asp Leu Pro Pro Glu Glu Ala
1               5                   10                  15

Ile Lys Val Gln Asn Glu Leu Arg Lys Lys Ile Lys Leu Thr Pro Tyr
            20                  25                  30

Glu Gly Glu Pro Glu Tyr Val Ala Gly Val Asp Leu Ser Phe Pro Gly
        35                  40                  45

Lys Glu Glu Gly Leu Ala Val Ile Val Val Leu Glu Tyr Pro Ser Phe
50                  55                  60

Lys Ile Leu Glu Val Val Ser Glu Arg Gly Ile Thr Phe Pro Ala
65                  70                  75                  80

Ile Pro Gly Leu Leu Ala Phe Arg Glu Gly Pro Leu Phe Leu Lys Ala
                85                  90                  95

Trp Glu Lys Leu Arg Thr Lys Pro Ala Val Val Phe Asp Gly Gln
            100                 105                 110

Gly Leu Ala His Pro Arg Lys Leu Gly Ile Ala Ser His Met Gly Leu
            115                 120                 125

Phe Ile Glu Ile Pro Thr Ile Gly Val Ala Lys Ser Arg Leu Tyr Gly
130                 135                 140

Thr Phe Lys Met Pro Glu Asp Lys Arg Cys Ser Trp Ser Tyr Leu Tyr
145                 150                 155                 160

Asp Gly Glu Glu Ile Ile Gly Cys Val Ile Arg Thr Lys Glu Gly Ser
            165                 170                 175

Ala Pro Ile Phe Val Ser Pro Gly His Leu Met Asp Val Glu Ser Ser
            180                 185                 190

Lys Arg Leu Ile Lys Ala Phe Thr Leu Pro Gly Arg Arg Ile Pro Glu
            195                 200                 205

Pro Thr Arg Leu Ala His Ile Tyr Thr Gln Arg Leu Lys Lys Gly Leu
            210                 215                 220

Phe
225

<210> SEQ ID NO 3
<211> LENGTH: 34
<212> TYPE: DNA
<213> ORGANISM: Artificial
<220> FEATURE:
<223> OTHER INFORMATION: Synthetic construct

<400> SEQUENCE: 3
ggagggaatc atatggatta caggcagctt caca                            34
```

<210> SEQ ID NO 4
<211> LENGTH: 37
<212> TYPE: DNA
<213> ORGANISM: Artificial
<220> FEATURE:
<223> OTHER INFORMATION: Synthetic construct

<400> SEQUENCE: 4
gcgcctggat cctcagaaaa ggcctttttt gagccgt          37

<210> SEQ ID NO 5
<211> LENGTH: 39
<212> TYPE: DNA
<213> ORGANISM: Artificial
<220> FEATURE:
<223> OTHER INFORMATION: Synthtic construct

<400> SEQUENCE: 5
gggagagata acttttcccg caattccggg gctccttgc          39

<210> SEQ ID NO 6
<211> LENGTH: 39
<212> TYPE: DNA
<213> ORGANISM: Artificial
<220> FEATURE:
<223> OTHER INFORMATION: Synthetic construct

<400> SEQUENCE: 6
gcaaggagcc ccggaattgc gggaaaagtt atctctccc          39

<210> SEQ ID NO 7
<211> LENGTH: 36
<212> TYPE: DNA
<213> ORGANISM: Artificial
<220> FEATURE:
<223> OTHER INFORMATION: Synthetic construct

<400> SEQUENCE: 7
aaagctgaga acgaaacccg cagttgtggt cttcga          36

<210> SEQ ID NO 8
<211> LENGTH: 36
<212> TYPE: DNA
<213> ORGANISM: Artificial
<220> FEATURE:
<223> OTHER INFORMATION: Synthetic construct

<400> SEQUENCE: 8
tcgaagacca caactgcggg tttcgttctc agcttt          36

<210> SEQ ID NO 9
<211> LENGTH: 21
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (20)..(20)
<223> OTHER INFORMATION: n is inosine

<400> SEQUENCE: 9
ggatgtgctg caaggcgatn a          21

<210> SEQ ID NO 10
<211> LENGTH: 23
<212> TYPE: DNA

<213> ORGANISM: Artificial
<220> FEATURE:
<223> OTHER INFORMATION: Synthetic construct
<220> FEATURE:
<221> NAME/KEY: misc_feature
<222> LOCATION: (22)..(22)
<223> OTHER INFORMATION: n is inosine

<400> SEQUENCE: 10
actcattagg cacccccaggc tnt                                              23

<210> SEQ ID NO 11
<211> LENGTH: 42
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (20)..(20)
<223> OTHER INFORMATION: n is inosine

<400> SEQUENCE: 11
ggatgtgctg caaggcgatn aagttgggta acgccagggt tt                          42

<210> SEQ ID NO 12
<211> LENGTH: 44
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (22)..(22)
<223> OTHER INFORMATION: n is inosine

<400> SEQUENCE: 12
actcattagg cacccccaggc tntacacttt atgcttccgg ctcg                       44

<210> SEQ ID NO 13
<211> LENGTH: 47
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (23)..(23)
<223> OTHER INFORMATION: n is inosine

<400> SEQUENCE: 13
ttatccgcct ccatccagtc tantaattgt tgccgggaag ctagagt                     47

<210> SEQ ID NO 14
<211> LENGTH: 42
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (22)..(22)
<223> OTHER INFORMATION: n is inosine

<400> SEQUENCE: 14
aacatttccg tgtcgccctt antcccttttt ttgcggcatt tt                         42

<210> SEQ ID NO 15
<211> LENGTH: 20
<212> TYPE: DNA

```
<213> ORGANISM: Artificial
<220> FEATURE:
<223> OTHER INFORMATION: Synthetic construct

<400> SEQUENCE: 15
cgggcctctt cgctattacg                                               20

<210> SEQ ID NO 16
<211> LENGTH: 20
<212> TYPE: DNA
<213> ORGANISM: Artificial
<220> FEATURE:
<223> OTHER INFORMATION: Synthetic construct

<400> SEQUENCE: 16
ggcagtgagc gcaacgcaat                                               20

<210> SEQ ID NO 17
<211> LENGTH: 35
<212> TYPE: DNA
<213> ORGANISM: Artificial
<220> FEATURE:
<223> OTHER INFORMATION: Synthetic construct

<400> SEQUENCE: 17
gctgagaacg aaacccggtg ttgtggtctt cgatg                              35

<210> SEQ ID NO 18
<211> LENGTH: 35
<212> TYPE: DNA
<213> ORGANISM: Artificial
<220> FEATURE:
<223> OTHER INFORMATION: Synthetic construct

<400> SEQUENCE: 18
catcgaagac cacaacaccg ggtttcgttc tcagc                              35

<210> SEQ ID NO 19
<211> LENGTH: 38
<212> TYPE: DNA
<213> ORGANISM: Artificial
<220> FEATURE:
<223> OTHER INFORMATION: Synthetic construct

<400> SEQUENCE: 19
aagctgagaa cgaaacccccg tgttgtggtc ttcgatgg                          38

<210> SEQ ID NO 20
<211> LENGTH: 38
<212> TYPE: DNA
<213> ORGANISM: Artificial
<220> FEATURE:
<223> OTHER INFORMATION: Synthetic construct

<400> SEQUENCE: 20
ccatcgaaga ccacaacacg gggtttcgtt ctcagctt                           38

<210> SEQ ID NO 21
<211> LENGTH: 33
<212> TYPE: DNA
<213> ORGANISM: Artificial
<220> FEATURE:
<223> OTHER INFORMATION: Synthetic construct

<400> SEQUENCE: 21
gctgagaacg aaaccccatg ttgtggtctt cga                                33
```

```
<210> SEQ ID NO 22
<211> LENGTH: 33
<212> TYPE: DNA
<213> ORGANISM: Artificial
<220> FEATURE:
<223> OTHER INFORMATION: Synthetic construct

<400> SEQUENCE: 22
tcgaagacca caacatgggg tttcgttctc agc                                  33

<210> SEQ ID NO 23
<211> LENGTH: 35
<212> TYPE: DNA
<213> ORGANISM: Artificial
<220> FEATURE:
<223> OTHER INFORMATION: Synthetic construct

<400> SEQUENCE: 23
ctgagaacga aacccgaggt tgtggtcttc gatgg                                35

<210> SEQ ID NO 24
<211> LENGTH: 35
<212> TYPE: DNA
<213> ORGANISM: Artificial
<220> FEATURE:
<223> OTHER INFORMATION: Synthetic construct

<400> SEQUENCE: 24
ccatcgaaga ccacaacctc gggtttcgtt ctcag                                35

<210> SEQ ID NO 25
<211> LENGTH: 35
<212> TYPE: DNA
<213> ORGANISM: Artificial
<220> FEATURE:
<223> OTHER INFORMATION: Synthetic construct

<400> SEQUENCE: 25
agctgagaac gaaacccaat gttgtggtct tcgat                                35

<210> SEQ ID NO 26
<211> LENGTH: 35
<212> TYPE: DNA
<213> ORGANISM: Artificial
<220> FEATURE:
<223> OTHER INFORMATION: Synthetic construct

<400> SEQUENCE: 26
atcgaagacc acaacattgg gtttcgttct cagct                                35

<210> SEQ ID NO 27
<211> LENGTH: 37
<212> TYPE: DNA
<213> ORGANISM: Artificial
<220> FEATURE:
<223> OTHER INFORMATION: Synthetic construct

<400> SEQUENCE: 27
agctgagaac gaaaccccag gttgtggtct tcgatgg                              37

<210> SEQ ID NO 28
<211> LENGTH: 37
<212> TYPE: DNA
<213> ORGANISM: Artificial
<220> FEATURE:
<223> OTHER INFORMATION: Synthetic construct
```

<400> SEQUENCE: 28
ccatcgaaga ccacaacctg gggtttcgtt ctcagct                                   37

<210> SEQ ID NO 29
<211> LENGTH: 42
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (20)..(20)
<223> OTHER INFORMATION: n is inosine

<400> SEQUENCE: 29
ggatgtgctg caaggcgatn aagttgggta acgccagggt tt                             42

<210> SEQ ID NO 30
<211> LENGTH: 44
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (22)..(22)
<223> OTHER INFORMATION: n is inosine

<400> SEQUENCE: 30
actcattagg cacccaggc tntacacttt atgcttccgg ctcg                            44

<210> SEQ ID NO 31
<211> LENGTH: 42
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (20)..(20)
<223> OTHER INFORMATION: n is inosine

<400> SEQUENCE: 31
ggatgtgctg caaggcgatn aagttgggta acgccagggt tt                             42

<210> SEQ ID NO 32
<211> LENGTH: 44
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (22)..(22)
<223> OTHER INFORMATION: n is inosine

<400> SEQUENCE: 32
actcattagg cacccaggc tntacacttt atgcttccgg ctcg                            44

<210> SEQ ID NO 33
<211> LENGTH: 42
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (20)..(20)
<223> OTHER INFORMATION: n is inosine

```
<400> SEQUENCE: 33
ggatgtgctg caaggcgatn aagttgggta acgccagggt tt                         42

<210> SEQ ID NO 34
<211> LENGTH: 44
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (22)..(22)
<223> OTHER INFORMATION: n is inosine

<400> SEQUENCE: 34
actcattagg cacccaggc tntacacttt atgcttccgg ctcg                        44

<210> SEQ ID NO 35
<211> LENGTH: 42
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (20)..(20)
<223> OTHER INFORMATION: n is inosine

<400> SEQUENCE: 35
ggatgtgctg caaggcgatn aagttgggta acgccagggt tt                         42

<210> SEQ ID NO 36
<211> LENGTH: 44
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (22)..(22)
<223> OTHER INFORMATION: n is inosine

<400> SEQUENCE: 36
actcattagg cacccaggc tntacacttt atgcttccgg ctcg                        44

<210> SEQ ID NO 37
<211> LENGTH: 42
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (20)..(20)
<223> OTHER INFORMATION: n is inosine

<400> SEQUENCE: 37
ggatgtgctg caaggcgatn aagttgggta acgccagggt tt                         42

<210> SEQ ID NO 38
<211> LENGTH: 44
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (22)..(22)
<223> OTHER INFORMATION: n is inosine
```

```
<400> SEQUENCE: 38
actcattagg caccccaggc tntacacttt atgcttccgg ctcg                    44

<210> SEQ ID NO 39
<211> LENGTH: 42
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (20)..(20)
<223> OTHER INFORMATION: n is inosine

<400> SEQUENCE: 39
ggatgtgctg caaggcgatn aagttgggta acgccagggt tt                      42

<210> SEQ ID NO 40
<211> LENGTH: 44
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (22)..(22)
<223> OTHER INFORMATION: n is inosine

<400> SEQUENCE: 40
actcattagg caccccaggc tntacacttt atgcttccgg ctcg                    44
```